US012529066B2

(12) United States Patent
Aponte et al.

(10) Patent No.: US 12,529,066 B2
(45) **Date of Patent: *Jan. 20, 2026**

(54) PLANTS HAVING INCREASED TOLERANCE TO HERBICIDES

(71) Applicant: BASF AGRO B.V., Arnhem (NL)

(72) Inventors: Raphael Aponte, Mannheim (DE); Stefan Tresch, Ludwigshafen (DE); Matthias Witschel, Ludwigshafen (DE); Jens Lerchl, Limburgerhof (DE); Jill Marie Paulik, Durham, NC (US); Chad Brommer, Raleigh, NC (US)

(73) Assignee: BASF AGRO B.V., Arnhem (NL)

( * ) Notice: Subject to any disclaimer, the term of this patent is extended or adjusted under 35 U.S.C. 154(b) by 328 days.

This patent is subject to a terminal disclaimer.

(21) Appl. No.: 18/157,370

(22) Filed: Jan. 20, 2023

(65) Prior Publication Data

US 2024/0026371 A1 Jan. 25, 2024

Related U.S. Application Data

(63) Continuation of application No. 16/035,115, filed on Jul. 13, 2018, now Pat. No. 11,572,571, which is a continuation of application No. 13/918,212, filed on Jun. 14, 2013, now Pat. No. 10,041,087.

(60) Provisional application No. 61/661,364, filed on Jun. 19, 2012.

(51) Int. Cl.

| | |
|---|---|
| ***C12N 15/82*** | (2006.01) |
| ***A01N 43/84*** | (2006.01) |
| ***C12N 9/02*** | (2006.01) |
| ***G01N 33/50*** | (2006.01) |

(52) U.S. Cl.

CPC ......... *C12N 15/8274* (2013.01); *A01N 43/84* (2013.01); *C12N 9/0004* (2013.01); *C12N 9/0059* (2013.01); *C12Y 103/03004* (2013.01); *G01N 33/5097* (2013.01); *G01N 2333/90206* (2013.01)

(58) Field of Classification Search

None

See application file for complete search history.

(56) References Cited

U.S. PATENT DOCUMENTS

| | | | |
|---|---|---|---|
| 5,169,770 | A | 12/1992 | Chee et al. |
| 5,198,013 | A | 3/1993 | Hirai et al. |
| 5,322,783 | A | 6/1994 | Tomes et al. |
| 5,366,892 | A | 11/1994 | Foncerrada et al. |
| 5,376,543 | A | 12/1994 | Chee et al. |
| 5,380,831 | A | 1/1995 | Adang et al. |
| 5,436,391 | A | 7/1995 | Fujimoto et al. |
| 5,485,192 | A | 1/1996 | Nagahata et al. |
| 5,593,881 | A | 1/1997 | Thompson et al. |
| 5,723,756 | A | 3/1998 | Peferoen et al. |
| 5,737,514 | A | 4/1998 | Stiffler |
| 5,747,450 | A | 5/1998 | Ohba et al. |
| 5,767,373 | A | 6/1998 | Ward et al. |
| 5,773,702 | A | 6/1998 | Penner et al. |
| 5,859,348 | A | 1/1999 | Penner et al. |
| 5,939,360 | A | 8/1999 | Adachi et al. |
| 5,939,602 | A | 8/1999 | Volrath et al. |
| 5,948,917 | A | 9/1999 | Adachi et al. |
| 5,990,387 | A | 11/1999 | Tomes et al. |
| 6,018,105 | A | 1/2000 | Johnson et al. |
| 6,027,945 | A | 2/2000 | Smith et al. |
| 6,084,155 | A | 7/2000 | Volrath et al. |
| 6,160,206 | A | 12/2000 | Sato et al. |
| 6,368,800 | B1 | 4/2002 | Smith et al. |
| 6,653,529 | B2 | 11/2003 | Peng et al. |
| 6,905,852 | B1 | 6/2005 | Horikoshi et al. |
| 7,250,561 | B1 | 7/2007 | Pallett et al. |
| 7,671,254 | B2 | 3/2010 | Tranel et al. |
| 7,705,200 | B2 | 4/2010 | Dam et al. |
| 7,745,699 | B2 | 6/2010 | Nakajima et al. |
| 7,842,856 | B2 | 11/2010 | Tranel et al. |
| 8,097,774 | B2 | 1/2012 | Hawkes et al. |
| 8,129,589 | B2 | 3/2012 | Tanaka et al. |
| 8,338,337 | B2 | 12/2012 | Song et al. |
| 11,441,154 | B2 | 9/2022 | Lerchl et al. |
| 11,572,571 | B2 | 2/2023 | Aponte et al. |
| 2003/0236208 | A1 | 12/2003 | Kmiec et al. |
| 2004/0082770 | A1 | 4/2004 | Castle et al. |
| 2005/0084859 | A1 | 4/2005 | Nakajima et al. |
| 2007/0021515 | A1 | 1/2007 | Glenn et al. |

(Continued)

FOREIGN PATENT DOCUMENTS

| | | | |
|---|---|---|---|
| CA | 2382090 | A1 | 2/2001 |
| CA | 2807035 | A1 | 2/2012 |

(Continued)

OTHER PUBLICATIONS

Li et a, Pest Manag. Sci. (2005) 61:277-285.*
Arnould et al., The domain structure of protoporphyrinogen oxidase, the molecular target of diphenyl ether-type herbicides. Proc. Natl. Acad. Sci. USA, 95: 10553-8 (1998).
Che et al., Localization of target-site of the protoporphyrinogen oxidase-inhibiting herbicide, S-23142, in Spinacia oleracea L., Z. Naturforsch., 48c:350-355 (1993).
Che et al., Molecular characterization and subcellular localization of protoporphyrinogen oxidase in spinach chloroplasts. Plant Physiol. 124: 59-70 (2000).

(Continued)

*Primary Examiner* — Mykola V. Kovalenko
(74) *Attorney, Agent, or Firm* — MARSHALL, GERSTEIN & BORUN LLP

(57) ABSTRACT

The present invention refers to a seed or plant that comprises at least one nucleic acid comprising a nucleotide sequence encoding a wild-type or a mutated protoporphyrinogen oxidase (PPO) which is resistant or tolerant to a benzoxazinone-derivative herbicide. The invention further refers to seeds or plants comprising wild-type or mutated PPO enzymes, and methods of obtaining such seeds or plants.

20 Claims, 4 Drawing Sheets

Specification includes a Sequence Listing.

(56) References Cited

U.S. PATENT DOCUMENTS

| | | | |
|---|---|---|---|
| 2007/0050863 | A1 | 3/2007 | Tranel et al. |
| 2009/0049567 | A1 | 2/2009 | Olhoft et al. |
| 2010/0100988 | A1 | 4/2010 | Tranel et al. |
| 2011/0201501 | A1 | 8/2011 | Song et al. |
| 2012/0122223 | A1 | 5/2012 | Gocal et al. |
| 2013/0184155 | A1 | 7/2013 | Newton et al. |
| 2014/0123340 | A1 | 5/2014 | Aponte et al. |
| 2014/0189906 | A1 | 7/2014 | Gocal et al. |

FOREIGN PATENT DOCUMENTS

| | | | |
|---|---|---|---|
| CN | 1150820 | A | 5/1997 |
| CN | 1036571 | C | 12/1997 |
| CN | 1212724 | A | 3/1999 |
| CN | 1175107 | C | 11/2004 |
| CN | 1894408 | A | 1/2007 |
| CN | 101215289 | A | 7/2008 |
| CN | 101437844 | A | 5/2009 |
| CN | 101998988 | A | 3/2011 |
| DE | 19505995 | A1 | 8/1996 |
| EP | 0397687 | A1 | 11/1990 |
| EP | 0424047 | A1 | 4/1991 |
| EP | 0900795 | A1 | 3/1999 |
| WO | WO-93/07256 | A1 | 4/1993 |
| WO | WO-96/26202 | A1 | 8/1996 |
| WO | WO-1997/004088 | A1 | 2/1997 |
| WO | WO-1997/032011 | A1 | 9/1997 |
| WO | WO-97/41116 | A1 | 11/1997 |
| WO | WO-97/41117 | A1 | 11/1997 |
| WO | WO-97/41118 | A1 | 11/1997 |
| WO | WO-1998/029554 | A1 | 7/1998 |
| WO | WO-98/33927 | A1 | 8/1998 |
| WO | WO-2001/012815 | A1 | 2/2001 |
| WO | WO-2001/068826 | A2 | 9/2001 |
| WO | WO-01/083459 | A2 | 11/2001 |
| WO | WO-02/068607 | A2 | 9/2002 |
| WO | WO-2005/107437 | A2 | 11/2005 |
| WO | WO-2006/024820 | A1 | 3/2006 |
| WO | WO-2006/037945 | A1 | 4/2006 |
| WO | WO-2007/024739 | A2 | 3/2007 |
| WO | WO-2007/071900 | A1 | 6/2007 |
| WO | WO-2007/096576 | A1 | 8/2007 |
| WO | WO-2008/124495 | A2 | 10/2008 |
| WO | WO-2008/141154 | A2 | 11/2008 |
| WO | WO-2010/049269 | A1 | 5/2010 |
| WO | WO-2010/049270 | A1 | 5/2010 |
| WO | WO-2010/145992 | A1 | 12/2010 |
| WO | WO-2011018486 | A2 | 2/2011 |
| WO | WO-2012/018862 | A2 | 2/2012 |
| WO | WO-2012/041789 | A1 | 4/2012 |
| WO | WO-2012/080975 | A1 | 6/2012 |
| WO | WO-2013/189984 | A2 | 12/2013 |
| WO | WO-2015/022636 | A2 | 2/2015 |
| WO | WO-2015/022639 | A2 | 2/2015 |
| WO | WO-2015/092706 | A1 | 6/2015 |

OTHER PUBLICATIONS

Choi et al., Generation of resistance to the diphenyl ether herbicide, oxyfluorfen, via expression of the Bacillus subtilis protoporphyrinogen oxidase gene in transgenic tobacco plants. Biosci. Biotechnol. Biochem. 62(3): 558-60 (1998).

Cole-Strauss et al., Targeted gene repair directed by the chimeric RNA/DNA oligonucleotide in a mammalian cell-free extract, Nucleic Acids Research, 27(5):1323-1330 (1999).

Corradi et al., Crystal structure of protoporphyrinogen oxidase from Myxococcus Xanthus and it complex with the inhibitor acifluorfen. J Biol Chem. 281(50): 38625-33 (2006).

Dailey et al., Expression of a cloned protoporphyrinogen oxidase, J. Biol. Chem., 269:813-815 (1994).

Dayan et al., Biochemical and structural consequences of a glycine deletion, Biochimica et Biophysica Acta, 1804:1548-56 (2010).

Dayan et al., Phytotoxicity of Protoporphyrinogen Oxidase Inhibitors: Phenomenology, Mode of Action and Mechanisms of Resistance, Herbicide Activity: Toxicology, Biochemistry and Molecular Biology, eds. Roe et al., pp. 11-35 (1997).

Duke et al., Protoporphyrinogen oxidase-inhibiting herbicides, Weed Sci., 39:465-473 (1991).

Extended European Search Report, issued in co-assigned application No. 11848519.2, dated Apr. 23, 2014.

Ge-Fei et al., Protoporphyrinogen Oxidase Inhibitor: An Ideal Target for Herbicide Discovery, CHIMIA, 65(12): 961-969 (2011).

Geiser et al., The hypervariable region in the genes coding for entomopathogenic crystal proteins of Bacillus thuringiensis: nucleotide sequence of the kurhd1 gene of subsp. kurstaki HD1, Gene, 48:109-118 (1986).

GenBank Accession No. ACF78832, unknown [*Zea mays*], Jul. 30, 2008.

GenBank Accession No. AX084732, submitted on Mar. 9, 2001.

GenBank Accession No. DQ386114, submitted on Jan. 31, 2006.

GenBank Accession No. XM_004975973, Predicted: Setaria italica protoporphyrinogen oxidase, mitochondrial (LOC101781148), mRNA, Nov. 30, 2015.

GenBank Accession No. XP_004976030.1, Predicted: Protoporhyrinogen oxidase, mitochondrial [Setaria italica], Nov. 30, 2015.

Ha et al., The plastidic *Arabidopsis protoporphyrinogen* IX oxidase gene, with or without the transit sequence, confers resistance to the diphenyl ether herbicide in rice. Plant Cell Environ. 27:79-88 (2003).

Hanin et al., Gene targeting in Arabidopsis. Plant J. 28: 671-7 (2001).

Hao et al., Protoporphyrinogen Oxidase Inhibitor: An Ideal Target for Herbicide Discovery, CHIMIA, 65(12): 961-969 (2011).

Heinemann et al., Functional definition of the tobacco protoporphyrinogen IX oxidase substrate-binding site, Biochem. J., 402:575-580 (2007).

Holmberg, A fine line: New herbicide-tolerant crops blur the fine line between weed control and crop injury. Successful Farm. 98(5): 25-7 (2000).

Huang et al., Synthesis and herbicidal activity of isoindoline-1,3-dione substituted benzoxazinone derivatives containing a carboxylic ester group. J. Agric. Food Chem. 57: 9585-92 (2009).

International Preliminary Report on Patentability, International Application No. PCT/IB2014/063873, mailed Feb. 16, 2016.

International Preliminary Report on Patentability, International Application No. PCT/IB2014/063876, mailed Feb. 16, 2016.

International Preliminary Report on Patentability, International Application No. PCT/IB2014/063877, mailed Feb. 16, 2016.

International Preliminary Report on Patentability, issued in PCT/IB2011/055701, dated Jun. 27, 2013.

International Search Report and Written Opinion, International Application No. PCT/IB2014/063873, mailed Feb. 9, 2015.

International Search Report and Written Opinion, International Application No. PCT/IB2014/063876, mailed Jan. 28, 2015.

International Search Report and Written Opinion, International Application No. PCT/IB2014/063877, mailed Feb. 10, 2015.

International Search Report, corresponding International Application No. PCT/EP2013/062744, mailing date Dec. 10, 2014.

International Search Report, issued in PCT/IB2011/055701, dated May 3, 2012.

Jacobs et al., Assay for enzymatic protoporphyrinogen oxidation, Enzyme, 28:206-219 (1982).

Joyce et al., Field performance of transgenic sugarcane produced using Agrobacterium and biolistics methods, Plant Biotechnol. J., 12: 411-24 (2014).

Jung et al., Dual targeting of Myxococcus xanthus protoporphyrinogen oxidase into chloroplasts and mitochondria and high level oxyfluorfen resistance. Plant Cell Environ. 27: 1436-46 (2004).

Jung et al., Resistance mechanisms in protoporphyrinogen oxidase (Protox) inhibitor-resistant transgenic rice. J. Plant Biol. 50(3): 586-94 (2007).

Kataoka et al., Isolation and partial characterization of mutant Chlamydomonas reinhardtii Resistant to Herbicide S-23142, J. Pesticide Sci., 15:449-451 (1990).

(56) References Cited

OTHER PUBLICATIONS

Koch et al., Crystal structure of protoporphyrinogen IX oxidase: a key enzyme in haem and chlorophyll biosynthesis, The EMBO Journal, 23:1720-1728 (2004).
Kohli et al., Transgene integration, expression and stability in plants: Strategies for improvements Chapter 7 IN: Cole et al., (eds.), Transgenic Crop Plants, Berlin: Springer-Verlag, (2010).
Layer et al., Structure and function of enzymes in Heme biosynthesis. Protein Sci. 19: 1137-61 (2010).
Lee et al., Cellular localization of protoprophyrinogen-oxidizing activities of etiolated barley (*Hordeum vulgare* L.) leaves, Plant Physiol., 102:881-889 (1993).
Lee et al., Expression of human protoporphyrinogen oxidase in transgenic rice induces both a photodynamic response and oxyfluorfen resistance. Pesticide Biochem. Physiol. 80: 65-74 (2004).
Lee et al., Transgenic rice plants expressing a Bacillus subtilis protoporphyrinogen oxidase gene are resistant to diphenyl ether herbicide oxyfluorfen, Plant Cell Physiol., 41(6):743-9 (2000).
Lermontova et al., Overexpression of plastidic protoporphyrinogen IX oxidase leads to resistance to the diphenyl-ether herbicide acifluorfen, Plant Physiology, 122:75-83 (2000).
Lermontova et al., Cloning and characterization of a plastidal and a mitochondria' isoform of tobacco protoporphyrinogen IX oxidase. Proc. Natl. Acad. Sci. USA, 94: 8895-900 (1997).
Lewis et al., Interactions between redox partners in various cytochrome P450 systems: Functional and structural aspects. Biochim. Biophys. Acta, 1460(2-3): 353-74 (2000).
Li et al., Development of PPO inhibitor-resistant cultures and crops. Pest. Manag. Sci. 61: 277-85 (2005).
Li, Development of protoporphyrinogen oxidase as an efficient selection marker for Agrobacterium tumefaciens-mediated transformation of Maize, Plant Physiology, 133(2):736-747 (2003).
Lipkie et al., Bioaccessibility of carotenoids from transgenic provitamin a biofortified sorghum, J. Agric. Food Chem., 61: 5764-71 (2013).
Loppes, A new class of arginine-requiring mutants in Chlamydomonas reinhardi, Mol. Gen. Genet., 20(104):172-177 (1969).
Lyga et al., Structural replacements for the benzoxazinone protox inhibitors. Pesticide Sci. 55: 281-7 (1999).
Macias et al., Optimization of benzoxazinones as natural herbicide models by lipophilicity enhancement. J. Acric. Food Chem. 54: 9357-65 (2006).
Matringe et al., Protoporphyrinogen oxidase as a molecular target for diphenyl ether herbicides, Biochem., 260(1):231-235 (1989).
Matringe et al., Protoporphyrinogen oxidase inhibition by three peroxidizing herbicides: oxadiazon, LS 82-556 and M&B 39279, FEBS Lett., 245:35-38 (1989).
Mulwa et al., Biotechnology approaches to developing herbicide tolerance/selectivity in crops. Afr. J. Biotechnol. 5(5): 396-404 (2006).
Murray et al., Condon usage in plant genes, Nucleic Acids Res., 17:477-498 (1989).
Nandihalli et al., Quantitative structure-activity relationships of protoporphyrinogen oxidase-inhibiting diphenyl ether herbicides, Pesticide Biochem. Physiol., 43:193-211 (1992).
Oshio et al., Isolation and characterization of a Chlamydomonas reinhardtii mutant resistant to photobleaching herbicides, Z. Naturforsch., 48c:339-344 (1993).
Patzoldt et al., A condon deletion confers resistance to herbicides inhibiting protoporphyrinogen oxidase, PNAS, 103(33): 12329-12334 (2006).
Randolph-Anderson et al., Isolation and characterization of a mutant protoporphyrinogen oxidase gene from Chlamydomonas reinhardtii conferring resistance to porphyric herbicides. Plant Mol. Biol. 38(5): 839-59 (1998).
Roberts et al., Targeted transgene integration overcomes variability of position effects in zebrafish, Development, 141: 715-24 (2014).
Rousonelos et al., Characterization of a Common Ragweed (*Ambrosia artemisiifolia*) Population Resistant to ALS- and PPO-Inhibiting Herbicides, Weed Sci., 60(3):335-44 (Sep. 2012).
Rousonelos, S., Master's Thesis, University of Illinois, published Aug. 2010.
Saint Pierre et al., Phenotyping transgenic wheat for drought resistance, J. Exp. Botany, 63(5): 1799-1808 (2012).
Sasarman et al., Mapping a new hem gene in *Escherichia coli* K12, J. Gen Microbiol, 113:297-303 (1979).
Sasarmen et al., Nucleotide sequence of the hemG gene involved in the protoporphyrinogen oxidase activity of *Escherichia coli* K12, Can. J. Microbiol., 39:1155-1159 (1993).
Shibata et al., Isolation and characterization of a Chlamydomonas reinhardtii mutant resistant to an experimental herbicide S-23142, which inhibits chlorophyll synthesis, Research in Photosynthesis, 3:567-570 (1992).
Su et al., The development of protoporphyrinogen oxidase inhibiting herbicides, Agrochem. Res. Appl. 15(1): 1-5 (2011)—English abstract only.
Trifunović et al., Overexpression of *Arabidopsis cytokinin* oxidase/dehydrogenase genes AtCKX1 and AtCKX2 in transgenic Centaurium erythraea Rafn, Plant Cell Tiss. Organ Cult., 115: 139-50 (2013).
UniProt Accession No. Q7X7T4_ORYSJ, integrated into the database on Oct. 1, 2003.
Van Leeuwen et al., The effect of MAR elements on variation in spatial and temporal regulation of transgene expression, Plant Mol. Bio. 47: 543-54 (2001).
Watanabe et al., Molecular characterization of photomixotrophic tobacco cells resistant to protoporphyrinogen oxidase-inhibiting herbicides. Plant Physiol. 118: 751-8 (1998).
Yanase et al., Porphyrin Synthesis Involvement in Diphenyl Ether-like Mode of Action of TNPP- Ethyl, a Novel Phenylpyrazole Herbicide, Pesticide Biochem. Physiol., 35:70-80 (1989).

* cited by examiner

SEQUENCE LISTING

```
Sequence total quantity: 48
SEQ ID NO: 1            moltype = DNA  length = 1605
FEATURE                 Location/Qualifiers
source                  1..1605
                        mol_type = other DNA
                        organism = Amaranthus tuberculatus
SEQUENCE: 1
atggtaattc aatccattac ccacctttca ccaaaccttg cattgccatc gccattgtca  60
gtttcaacca agaactaccc agtagctgta atgggcaaca tttctgagcg ggaagaaccc  120
acttctgcta aaagggttgc tgttgttggt gctggagtta gtggacttgc tgctgcatat  180
aagctaaaat cccatggttt gagtgtgaca ttgtttgaag ctgattctag agctggaggc  240
aaacttaaaa ctgttaaaaa agatggtttt atttgggatg agggggcaaa tactatgaca  300
gaaagtgagg cagaggtctc gagtttgatc gatgatcttg ggcttcgtga gaagcaacag  360
ttgccaattt cacaaaataa aagatacata gctagagacg gtcttcctgt gctactacct  420
tcaaatcccg ctgcactact cacgagcaat atcctttcag caaaatcaaa gctgcaaatt  480
atgttggaac catttctctg gagaaaacac aatgctactg aactttctga tgagcatgtt  540
caggaaagcg ttggtgaatt ttttgagcga cattttggga aagagtttgt tgattatgtt  600
atcgaccctt ttgttgcggg tacatgtggt ggagatcctc aatcgctttc catgcaccat  660
acatttccag aagtatggaa tattgaaaaa aggtttggct ctgtgtttgc tggactaatt  720
caatcaacat tgttatctaa gaaggaaaag ggtggagaaa atgcttctat taagaagcct  780
cgtgtacgtg gttcattttc atttcaaggt ggaatgcaga cacttgttga cacaatgtgc  840
aaacagcttg gtgaagatga actcaaactc cagtgtgagg tgctgtcctt gtcatataac  900
cagaagggga tcccctcatt agggaattgg tcagtctctt ctatgtcaaa taataccagt  960
gaagatcaat cttatgatgc tgtggttgtc actgctccaa ttcgcaatgt caaagaaatg  1020
aagattatga aatttggaaa tccattttca cttgacttta ttccagaggt gacgtacgta  1080
ccccttttccg ttatgattac tgcattcaaa aaggataaag tgaagagacc tcttgagggc  1140
ttcggagttc ttatcccctc taaagagcaa cataatggac tgaagactct tggtacttta  1200
ttttcctcca tgatgtttcc tgatcgtgct ccatctgaca tgtgtctctt tactacattt  1260
gtcggaggaa gcagaaatag aaaacttgca aacgcttcaa cggatgaatt gaagcaaata  1320
gtttcttctg accttcagca gctgttgggc actgaggacg aaccttcatt tgtcaatcat  1380
ctcttttgga gcaacgcatt cccattgtat ggacacaatt acgattctgt tttgagagcc  1440
atagacaaga tggaaaagga tcttcctgga ttttttttatg caggtaacca taagggtgga  1500
ctttcagtgg gaaaagcgat ggcctccgga tgcaaggctg cggaacttgt aatatcctat  1560
ctggactctc atatatacgt gaagatggat gagaagaccg cgtaa                 1605

SEQ ID NO: 2            moltype = AA  length = 534
FEATURE                 Location/Qualifiers
source                  1..534
                        mol_type = protein
                        organism = Amaranthus tuberculatus
SEQUENCE: 2
MVIQSITHLS PNLALPSPLS VSTKNYPVAV MGNISEREEP TSAKRVAVVG AGVSGLAAAY  60
KLKSHGLSVT LFEADSRAGG KLKTVKKDGF IWDEGANTMT ESEAEVSSLI DDLGLREKQQ  120
LPISQNKRYI ARDGLPVLLP SNPAALLTSN ILSAKSKLQI MLEPFLWRKH NATELSDEHV  180
QESVGEFFER HFGKEFVDYV IDPFVAGTCG GDPQSLSMHH TFPEVWNIEK RFGSVFAGLI  240
QSTLLSKKEK GGENASIKKP RVRGSFSFQG GMQTLVDTMC KQLGEDELKL QCEVLSLSYN  300
QKGIPSLGNW SVSSMSNNTS EDQSYDAVVV TAPIRNVKEM KIMKFGNPFS LDFIPEVTYV  360
PLSVMITAFK KDKVKRPLEG FGVLIPSKEQ HNGLKTLGTL FSSMMFPDRA PSDMCLFTTF  420
VGGSRNRKLA NASTDELKQI VSSDLQQLLG TEDEPSFVNH LFWSNAFPLY GHNYDSVLRA  480
IDKMEKDLPG FFYAGNHKGG LSVGKAMASG CKAAELVISY LDSHIYVKMD EKTA        534

SEQ ID NO: 3            moltype = DNA  length = 1605
FEATURE                 Location/Qualifiers
source                  1..1605
                        mol_type = other DNA
                        organism = Amaranthus tuberculatus
SEQUENCE: 3
atggtaattc aatccattac ccacctttca ccaaaccttg cattgccatc gccattgtca  60
gtttcaacca agaactaccc agtagctgta atgggcaaca tttctgagcg ggaagaaccc  120
acttctgcta aaagggttgc tgttgttggt gctggagtta gtggacttgc tgctgcatat  180
aagctaaaat cccatggttt gagtgtgaca ttgtttgaag ctgattctag agctggaggc  240
aaacttaaaa ctgttaaaaa agatggtttt atttgggatg agggggcaaa tactatgaca  300
gaaagtgagg cagaggtctc gagtttgatc gatgatcttg ggcttcgtga gaagcaacag  360
ttgccaattt cacaaaataa aagatacata gctagagccg gtcttcctgt gctactacct  420
tcaaatcccg ctgcactact cacgagcaat atcctttcag caaaatcaaa gctgcaaatt  480
atgttggaac catttctctg gagaaaacac aatgctactg aactttctga tgagcatgtt  540
caggaaagcg ttggtgaatt ttttgagcga cattttggga aagagtttgt tgattatgtt  600
attgaccctt ttgttgcggg tacatgtggt ggagatcctc aatcgctttc catgcaccat  660
acatttccag aagtatggaa tattgaaaaa aggtttggct ctgtgtttgc cggactaatt  720
caatcaacat tgttatctaa gaaggaaaag ggtggagaaa atgcttctat taagaagcct  780
cgtgtacgtg gttcattttc atttcaaggt ggaatgcaga cacttgttga cacaatgtgc  840
aaacagcttg gtgaagatga actcaaactc cagtgtgagg tgctgtcctt gtcatataac  900
cagaagggga tcccctcact agggaattgg tcagtctctt ctatgtcaaa taataccagt  960
gaagatcaat cttatgatgc tgtggttgtc actgctccaa ttcgcaatgt caaagaaatg  1020
aagattatga aatttggaaa tccattttca cttgacttta ttccagaggt gacgtacgta  1080
ccccttttccg ttatgattac tgcattcaaa aaggataaag tgaagagacc tcttgagggc  1140
ttcggagttc ttatcccctc taaagagcaa cataatggac tgaagactct tggtacttta  1200
ttttcctcca tgatgtttcc tgatcgtgct ccatctgaca tgtgtctctt tactacattt  1260
```

-continued

```
gtcggaggaa gcagaaatag aaaacttgca aacgcttcaa cggatgaatt gaagcaaata  1320
gtttcttctg accttcagca gctgttgggc actgaggacg aaccttcatt tgtcaatcat  1380
ctcttttgga gcaacgcatt cccattgtat ggacacaatt acgattctgt tttgagagcc  1440
atagacaaga tggaaaagga tcttcctgga ttttttatg caggtaacca taagggtgga  1500
ctttcagtgg gaaaagcgat ggcctccgga tgcaaggctg cggaacttgt aatatcctat  1560
ctggactctc atatatacgt gaagatggat gagaagaccg cgtaa                  1605

SEQ ID NO: 4           moltype = AA  length = 534
FEATURE                Location/Qualifiers
source                 1..534
                       mol_type = protein
                       organism = Amaranthus tuberculatus
SEQUENCE: 4
MVIQSITHLS PNLALPSPLS VSTKNYPVAV MGNISEREEP TSAKRVAVVG AGVSGLAAAY  60
KLKSHGLSVT LFEADSRAGG KLKTVKKDGF IWDEGANTMT ESEAEVSSLI DDLGLREKQQ  120
LPISQNKRYI ARAGLPVLLP SNPAALLTSN ILSAKSKLQI MLEPFLWRKH NATELSDEHV  180
QESVGEFFER HFGKEFVDYV IDPFVAGTCG GDPQSLSMHH TFPEVWNIEK RFGSVFAGLI  240
QSTLLSKKEK GGENASIKKP RVRGSFSFQG GMQTLVDTMC KQLGEDELKL QCEVLSLSYN  300
QKGIPSLGNW SVSSMSNNTS EDQSYDAVVV TAPIRNVKEM KIMKFGNPFS LDFIPEVTYV  360
PLSVMITAFK KDKVKRPLEG FGVLIPSKEQ HNGLKTLGTL FSSMMFPDRA PSDMCLFTTF  420
VGGSRNRKLA NASTDELKQI VSSDLQQLLG TEDEPSFVNH LFWSNAFPLY GHNYDSVLRA  480
IDKMEKDLPG FFYAGNHKGG LSVGKAMASG CKAAELVISY LDSHIYVKMD EKTA        534

SEQ ID NO: 5           moltype = DNA  length = 1602
FEATURE                Location/Qualifiers
source                 1..1602
                       mol_type = other DNA
                       organism = Amaranthus tuberculatus
SEQUENCE: 5
atggtaattc aatccattac ccacctttca ccaaaccttg cattgccatc gccattgtca  60
gtttccacca agaactaccc agtagctgta atgggcaaca tttctgagcg agaagaaccc  120
acttctgcta aaagggttgc tgttgttggt gctggagtta gtggacttgc tgctgcatat  180
aagctaaaat cccatggttt gagtgtgaca ttgtttgaag ctgattctag agctggaggc  240
aaacttaaaa ctgttaaaaa agatggtttt atttgggatg agggggcaaa tactatgaca  300
gaaagtgagg cagaggtctc gagtttgatc gatgatcttg ggcttcgtga gaagcaacag  360
ttgccaattt cacaaaataa aagatacata gctagagacg gtcttcctgt gctactacct  420
tcaaatcccg ctgcactact cacgagcaat atcctttcag caaaatcaaa gctgcaaatt  480
atgttggaac catttctctg gagaaaacac aatgctactg aactttctga tgagcatgtt  540
caggaaagcg ttggtgaatt ttttgagcga cattttggga aagagtttgt tgattatgtt  600
attgacccctt ttgttgcggg tacatgtgga gatcctcaat cgctttccat gcaccataca  660
tttccagaag tatggaatat tgaaaaaagg tttggctctg tgtttgctgg actaattcaa  720
tcaacattgt tatctaagaa ggaaaagggt ggagaaaatg cttctattaa gaagcctcgt  780
gtacgtggtt cattttcatt tcaaggtgga atgcagacac ttgttgacac aatgtgcaaa  840
cagcttggtg aagatgaact caaactccag tgtgaggtgc tgtccttgtc atataaccag  900
aaggggatcc cctcattagg gaattggtca gtctcttcta tgtcaaataa taccagtgaa  960
gatcaatctt atgatgctgt ggttgtcact gctccaattc gcaatgtcaa agaaatgaag  1020
attatgaaat ttggaaatcc attttcactt gactttattc cagaggtgac gtacgtaccc  1080
ctttccgtta tgattactgc attcaaaaag gataaagtga agagacctct tgagggcttc  1140
ggagttctta tcccctctaa agagcaacat aatggactga agactcttgg tactttattt  1200
tcctccatga tgtttcctga tcgtgctcca tctgacatgt gtctctttac tacatttgtc  1260
ggaggaagca gaaatagaaa acttgcaaac gcttcaacgg atgaattgaa gcaaatagtt  1320
tcttctgacc ttcagcagct gttgggcact gaggacgaac cttcatttgt caatcatctc  1380
ttttggagca acgcattccc attgtatgga cacaattacg attgtgtttt gagagccata  1440
gacaagatgg aaaaggatct tcctggattt ttttatgcag gtaaccataa gggtggactt  1500
tcagtgggaa aagcgatggc ctccggatgc aaggctgcgg aacttgtaat atcctatctg  1560
gactctcata tatacgtgaa gatggatgag aagaccgcgt aa                     1602

SEQ ID NO: 6           moltype = AA  length = 533
FEATURE                Location/Qualifiers
source                 1..533
                       mol_type = protein
                       organism = Amaranthus tuberculatus
SEQUENCE: 6
MVIQSITHLS PNLALPSPLS VSTKNYPVAV MGNISEREEP TSAKRVAVVG AGVSGLAAAY  60
KLKSHGLSVT LFEADSRAGG KLKTVKKDGF IWDEGANTMT ESEAEVSSLI DDLGLREKQQ  120
LPISQNKRYI ARDGLPVLLP SNPAALLTSN ILSAKSKLQI MLEPFLWRKH NATELSDEHV  180
QESVGEFFER HFGKEFVDYV IDPFVAGTCG DPQSLSMHHT FPEVWNIEKR FGSVFAGLIQ  240
STLLSKKEKG GENASIKKPR VRGSFSFQGG MQTLVDTMCK QLGEDELKLQ CEVLSLSYNQ  300
KGIPSLGNWS VSSMSNNTSE DQSYDAVVVT APIRNVKEMK IMKFGNPFSL DFIPEVTYVP  360
LSVMITAFKK DKVKRPLEGF GVLIPSKEQH NGLKTLGTLF SSMMFPDRAP SDMCLFTTFV  420
GGSRNRKLAN ASTDELKQIV SSDLQQLLGT EDEPSFVNHL FWSNAFPLYG HNYDCVLRAI  480
DKMEKDLPGF FYAGNHKGGL SVGKAMASGC KAAELVISYL DSHIYVKMDE KTA         533

SEQ ID NO: 7           moltype = DNA  length = 1602
FEATURE                Location/Qualifiers
source                 1..1602
                       mol_type = other DNA
                       organism = Amaranthus tuberculatus
SEQUENCE: 7
```

-continued

```
atggtaattc aatccattac ccacctttca ccaaaccttg cattgccatc gccattgtca  60
gtttccacca agaactaccc agtagctgta atgggcaaca tttctgagcg ggaagaaccc  120
acttctgcta aaagggttgc tgttgttggt gctggagtta gtggacttgc tgctgcatat  180
aagctaaaat cccatggttt gagtgtgaca ttgtttgaag ctaattctag agctggaggc  240
aaacttaaaa ctgttaaaaa agatggtttt atttgggatg agggggcaaa tactatgaca  300
gaaagtgagg cagaggtctc gagtttgatc gatgatcttg ggcttcgtga gaagcaacag  360
ttgccaattt cacaaaataa aagatacata gctagagacg gtcttcctgt gctactacct  420
tcaaatcccg ctgcactact cacgagcaat atcctttcag caaaatcaaa gctgcaaatt  480
atgttggaac catttctctg gagaaaacac aatgctactg aactttctga tgagcatgtt  540
caggaaagcg ttggtgaatt ttttgagcga cattttggga aagagtttgt tgattatgtt  600
attgaccctt ttgttgcggg tacatgtgga gatcctcaat cgctttccat gtaccataca  660
tttccagaag tatggaatat tgaaaaaagg tttggctctg tgtttgctgg actaattcaa  720
tcaacattgt tatctaagaa ggaaaagggt ggagaaaatg cttctattaa gaagcctcgt  780
gtacgtggtt cattttcatt tcaaggtgga atgcagacac ttgttgacac aatgtgcaaa  840
cagcttggtg aagatgaact caaactccag tgtgaggtgc tgtccttgtc atataaccag  900
aaggggatcc cctcattagg gaattggtca gtctcttcta tgtcaaataa taccagtgaa  960
gatcaatctt atgatgctgt ggttgtcact gctccaattc gcaatgtcaa agaaatgaag  1020
attatgaaat ttggaaatcc attttcactt gactttattc cagaggtgac gtacgtaccc  1080
ctttccgtta tgattactgc attcaaaaag gataaagtga agagacctct tgagggcttc  1140
ggagttctta tcccctctaa agagcaacat aatggactga agactcttgg tactttattt  1200
tcctccatga tgtttcctga tcgtgctcca tctgacatgt gtctctttac tacatttgtc  1260
ggaggaagca gaaatagaaa acttgcaaac gcttcaacgg atgaattgaa gcaaatagtt  1320
tcttctgacc ttcagcagct gttgggcact gaggacgaac cttcatttgt caatcatctc  1380
ttttggagca acgcattccc attgtatgga cacaattacg attctgtttt gagagccata  1440
gacaagatgg aaaaggatct tcctggattt ttttatgcag gtaaccataa gggtggactt  1500
tcagtgggaa aagcgatggc ctccggatgc aaggctgcgg aacttgtaat atcctatctg  1560
gactctcata tatacgtgaa gatggatgag aagaccgcgt aa                    1602

SEQ ID NO: 8           moltype = AA  length = 533
FEATURE                Location/Qualifiers
source                 1..533
                       mol_type = protein
                       organism = Amaranthus tuberculatus
SEQUENCE: 8
MVIQSITHLS PNLALPSPLS VSTKNYPVAV MGNISEREEP TSAKRVAVVG AGVSGLAAAY  60
KLKSHGLSVT LFEANSRAGG KLKTVKKDGF IWDEGANTMT ESEAEVSSLI DDLGLREKQQ  120
LPISQNKRYI ARDGLPVLLP SNPAALLTSN ILSAKSKLQI MLEPFLWRKH NATELSDEHV  180
QESVGEFFER HFGKEFVDYV IDPFVAGTCG DPQSLSMYHT FPEVWNIEKR FGSVFAGLIQ  240
STLLSKKEKG GENASIKKPR VRGSFSFQGG MQTLVDTMCK QLGEDELKLQ CEVLSLSYNQ  300
KGIPSLGNWS VSSMSNNTSE DQSYDAVVVT APIRNVKEMK IMKFGNPFSL DFIPEVTYVP  360
LSVMITAFKK DKVKRPLEGF GVLIPSKEQH NGLKTLGTLF SSMMFPDRAP SDMCLFTTFV  420
GGSRNRKLAN ASTDELKQIV SSDLQQLLGT EDEPSFVNHL FWSNAFPLYG HNYDSVLRAI  480
DKMEKDLPGF FYAGNHKGGL SVGKAMASGC KAAELVISYL DSHIYVKMDE KTA         533

SEQ ID NO: 9           moltype = DNA  length = 1644
FEATURE                Location/Qualifiers
source                 1..1644
                       mol_type = other DNA
                       organism = Arabidopsis thaliana
SEQUENCE: 9
atgggcctga ttaaaaacgg taccctttat tgtcgttttg ggataagctg gaattttgcc  60
gctgtgtttt tttctactta tttccgtcac tgctttcgac tggtcagaga ttttgactct  120
gaattgttgc agatagcaat ggcgtctgga gcagtagcag atcatcaaat tgaagcggtt  180
tcaggaaaaa gagtcgcagt cgtaggtgca ggtgtaagtg gacttgcggc ggcttacaag  240
ttgaaatcga ggggtttgaa tgtgactgtg tttgaagctg atggaagagt aggtgggaag  300
ttgagaagtg ttatgcaaaa tggtttgatt tgggatgaag gagcaaacac catgactgag  360
gctgagccag aagttgggag tttacttgat gatcttgggc ttcgtgagaa acaacaattt  420
ccaatttcac agaaaaagcg gtatattgtg cggaatggtg tacctgtgat gctacctacc  480
aatcccatag agctggtcac aagtagtgtg ctctctaccc aatctaagtt tcaaatcttg  540
ttggaaccat ttttatggaa gaaaaagtcc tcaaaagtct cagatgcatc tgctgaagaa  600
agtgtaagcg agttctttca acgccatttt ggacaagagg ttgttgacta tctcatcgac  660
ccttttgttg gtggaacaag tgctgcggac cctgattccc tttcaatgaa gcattctttc  720
ccagatctct ggaatagttt tggctctatt atagtcggtg caatcagaac aaagtttgct  780
gctaaaggtg gtaaaagtag agacacaaag agttctcctg gcacaaaaaa gggttcgcgt  840
gggtcattct cttttaaggg gggaatgcag attcttcctg atacgttgtg caaaagtctc  900
tcacatgatg agatcaattt agactccaag gtactctctt tgtcttacaa ttctggatca  960
agacaggaga actggtcatt atcttgtgtt tcgcataatg aaacgcagag acaaaacccc  1020
cattatgatg ctgctcctct gtgcaatgtg aaggagatga aggttatgaa aggaggacaa  1080
ccctttcagc taaactttct ccccgagatt aattacatgc ccctctcggt tttaatcacc  1140
acattcacaa aggagaaagt aaagagacct cttgaaggct ttggggtact cattccatct  1200
aaggagcaaa agcatggttt caaaactcta ggtacacttt tttcatcaat gatgtttcca  1260
gatcgttccc ctagtgacgt tcatctatat acaactttta ttggtgggag taggaaccag  1320
gaactagcca aagcttccac tgacgaatta aaacaagttg tgacttctga ccttcagcga  1380
ctgttggggg ttgaaggtga acccgtgtct gtcaaccatt actattggag gaaagcattc  1440
ccgttgtatg acagcagcta tgactcagtc atggaagcaa ttgacaagat ggagaatgat  1500
ctacctgggt tcttctatgc aggtaatcat cgagggggc tctctgttgg gaaatcaata  1560
gcatcaggtt gcaaagcagc tgaccttgtg atctcatacc tggagtcttg ctcaaatgac  1620
aagaaaccaa atgacagctt ataa                                        1644
```

-continued

```
SEQ ID NO: 10          moltype = AA  length = 547
FEATURE                Location/Qualifiers
source                 1..547
                       mol_type = protein
                       organism = Arabidopsis thaliana
SEQUENCE: 10
MGLIKNGTLY CRFGISWNFA AVFFSTYFRH CFRLVRDFDS ELLQIAMASG AVADHQIEAV  60
SGKRVAVVGA GVSGLAAAYK LKSRGLNVTV FEADGRVGGK LRSVMQNGLI WDEGANTMTE  120
AEPEVGSLLD DLGLREKQQF PISQKKRYIV RNGVPVMLPT NPIELVTSSV LSTQSKFQIL  180
LEPFLWKKKS SKVSDASAEE SVSEFFQRHF GQEVVDYLID PFVGGTSAAD PDSLSMKHSF  240
PDLWNSFGSI IVGAIRTKFA AKGGKSRDTK SSPGTKKGSR GSFSFKGGMQ ILPDTLCKSL  300
SHDEINLDSK VLSLSYNSGS RQENWSLSCV SHNETQRQNP HYDAAPLCNV KEMKVMKGGQ  360
PFQLNFLPEI NYMPLSVLIT TFTKEKVKRP LEGFGVLIPS KEQKHGFKTL GTLFSSMMFP  420
DRSPSDVHLY TTFIGGSRNQ ELAKASTDEL KQVVTSDLQR LLGVEGEPVS VNHYYWRKAF  480
PLYDSSYDSV MEAIDKMEND LPGFFYAGNH RGGLSVGKSI ASGCKAADLV ISYLESCSND  540
KKPNDSL                                                            547

SEQ ID NO: 11          moltype = DNA  length = 1647
FEATURE                Location/Qualifiers
source                 1..1647
                       mol_type = other DNA
                       organism = Nicotiana tabacum
SEQUENCE: 11
atgacaacaa ctcccatcgc caatcatcct aatattttca ctcaccagtc gtcgtcatcg  60
ccattggcat tcttaaaccg tacgagtttc atccctttct cttcaatctc caagcgcaat  120
agtgtcaatt gcaatggctg gagaacacga tgctccgttg ccaaagatta cacagttcct  180
tcctcagcgg tcgacggcgg acccgccgcg gagctggact gtgttatagt tggagcagga  240
attagtggcc tctgcattgc gcaggtgatg tccgctaatt accccaattt gatggtaacc  300
gaggcgagag atcgtgccgg tggcaacata acgactgtgg aaagagacgg ctatttgtgg  360
gaagaaggtc ccaacagttt ccagccgtcc gatcctatgt tgactatggc agtagattgt  420
ggattgaagg atgatttggt gttgggagat cctaatgcgc cccgtttcgt tttgtggaag  480
ggtaaattaa ggcccgtccc ctcaaaactc actgatcttc ccttttttga tttgatgagc  540
attcctggca agttgagagc tggttttggt gccattggcc tccgcccttc acctccaggt  600
catgaggaat cagttgagca gttcgtgcgt cgtaatcttg gtggcgaagt ctttgaacgc  660
ttgatagaac cattttgttc tggtgtttat gctggtgatc cctcaaaact gagtatgaaa  720
gcagcatttg ggaaagtttg gaagttggaa gaaactggtg gtagcattat tggaggaacc  780
tttaaagcaa taaaggagag atccagtaca cctaaagcgc cccgcgatcc gcgtttacct  840
aaaccaaaag gacagacagt tggatcattc aggaagggtc tcagaatgct gccggatgca  900
atcagtgcaa gattgggaag caaattaaaa ctatcatgga agctttctag cattactaag  960
tcagaaaaag gaggatatca cttgacatac gagacaccag aaggagtagt ttctcttcaa  1020
agtcgaagca ttgtcatgac tgtgccatcc tatgtagcaa gcaacatatt acgtcctctt  1080
tcggttgccg cagcagatgc actttcaaat ttctactatc ccccagttgg agcagtcaca  1140
atttcatatc ctcaagaagc tattcgtgat gagcgtctgg ttgatggtga actaaaggga  1200
tttgggcagt tgcatccacg tacacaggga gtggaaacac taggaacgat atatagttca  1260
tcactcttcc ctaaccgtgc cccaaaaggt cgggtgctac tcttgaacta cattggagga  1320
gcaaaaaatc ctgaaatttt gtctaagacg gagagccaac ttgtggaagt agttgatcgt  1380
gacctcagaa aaatgcttat aaaacccaaa gctcaagatc ctcttgttgt gggtgtgcga  1440
gtatggccac aagctatccc acagtttttg gttggtcatc tggatacgct aagtactgca  1500
aaagctgcta tgaatgataa tgggcttgaa gggctgtttc ttgggggtaa ttatgtgtca  1560
ggtgtagcat tggggaggtg tgttgaaggt gcttatgaag ttgcatccga ggtaacagga  1620
tttctgtctc ggtatgcata caaatga                                      1647

SEQ ID NO: 12          moltype = AA  length = 548
FEATURE                Location/Qualifiers
source                 1..548
                       mol_type = protein
                       organism = Nicotiana tabacum
SEQUENCE: 12
MTTTPIANHP NIFTHQSSSS PLAFLNRTSF IPFSSISKRN SVNCNGWRTR CSVAKDYTVP  60
SSAVDGGPAA ELDCVIVGAG ISGLCIAQVM SANYPNLMVT EARDRAGGNI TTVERDGYLW  120
EEGPNSFQPS DPMLTMAVDC GLKDDLVLGD PNAPRFVLWK GKLRPVPSKL TDLPFFDLMS  180
IPGKLRAGFG AIGLRPSPPG HEESVEQFVR RNLGGEVFER LIEPFCSGVY AGDPSKLSMK  240
AAFGKVWKLE ETGGSIIGGT FKAIKERSST PKAPRDPRLP KPKGQTVGSF RKGLRMLPDA  300
ISARLGSKLK LSWKLSSITK SEKGGYHLTY ETPEGVVSLQ SRSIVMTVPS YVASNILRPL  360
SVAAADALSN FYYPPVGAVT ISYPQEAIRD ERLVDGELKG FGQLHPRTQG VETLGTIYSS  420
SLFPNRAPKG RVLLLNYIGG AKNPEILSKT ESQLVEVVDR DLRKMLIKPK AQDPLVVGVR  480
VWPQAIPQFL VGHLDTLSTA KAAMNDNGLE GLFLGGNYVS GVALGRCVEG AYEVASEVTG  540
FLSRYAYK                                                           548

SEQ ID NO: 13          moltype = DNA  length = 1668
FEATURE                Location/Qualifiers
source                 1..1668
                       mol_type = other DNA
                       organism = Cichorium intybus
SEQUENCE: 13
atgacatctc tcacagacgt ttgttccctc aactgttgcc gtagctggtc ttcccttccg  60
ccaccggttt ctggtgggtc gttgacgtca aagaatccta ggtacctaat cacgtatagt  120
ccggcgcatc gcaaatgcaa taggtggagg ttccgctgct ctatagccaa ggattcccca  180
attactcctc ccatttcaaa tgagttcaac tctcagccat tgttggactg tgtcattgtg  240
```

-continued

```
ggcgccggca ttagcggcct ttgcattgcg caggccctag cgactaaaca cgcctccgtc  300
tctccggatg tgatcgtcac cgaggcacga gacagagtcg gggtaatat atcaacggtt  360
gaaagggatg gctatctctg ggaagaaggt cctaacagct tccagccatc tgatgccatg  420
ctcaccatgg tggtggatag tgggttgaag gatgatttgg tgttaggtga cccaacagca  480
ccccgctttg tattatgggg aggtgatttg aaaccggttc cttccaaacc ggctgacctc  540
cctttctttg acctcatgag ctttcctgga aaactcagag ccggttttgg tgctcttgga  600
ttccgtcctt cacctccaga tcgcgaagaa tcggttgagg agtttgttag acgtaatctt  660
ggagatgaag ttttcgaacg cttgatagaa ccttttgct caggtgttta tgctggtgat  720
ccatcaaaac ttagtatgaa agcagcattt gggaaggtct ggaatctgga gcaaaatggt  780
ggtagcattg ttggtggagc cttcaaggct attcaggaca gaaagaatag tcaaaagcct  840
ccacgggacc cgaggttacc gaaaccaaag ggccaaactg ttggatcttt taggaaagga  900
caagcgatgt tgcctaatgc aatctcaacg aggttaggta gcagagtgaa attgtgttgg  960
aagctcacga gtatttcaaa attggagaat agaggttata atttgacata tgaaacacca  1020
caaggatttg aaagtctgca gactaaaact atcgtgatga ctgttccatc ctacgtggcg  1080
agtgacttgt tgcgtccgct ttcgttgggt gcagcagatg cattgtcaaa attttattat  1140
cctccggttg cagctgtatc aatttcatat ccaaaagacg caattcgtgc tgaccggctg  1200
attgatggtc aactcaaagg ttttgggcaa ttgcatccac gaagtcaagg ggtggaaact  1260
ttaggtacga tctacagttc atctcttttc cctaaccgag cgccacctgg aagggttctg  1320
ctcttgaact acatcggagg ggctacaaat cctgaaattc tatcaaagac ggagggcgaa  1380
attgtggatg cggtggaccg ggacctacgg acgatgctga taaggcgtga tgcggaagat  1440
ccattgacgt tgggggtgcg ggtgtggcct cgagcaatcc cgcagtttct gatcggtcat  1500
tatgacattc tagattctgc aaaagctgct ctgagtagcg gtggattcca aggtatgttt  1560
cttggtggca actatgtgtc tggtgtggct ttaggtaaat gtgtcgaggc tgcttatgat  1620
gttgccgctg aggtaatgaa ctttttgtcg caaggggtgt acaagtga               1668

SEQ ID NO: 14          moltype = AA  length = 555
FEATURE                Location/Qualifiers
source                 1..555
                       mol_type = protein
                       organism = Cichorium sp.
SEQUENCE: 14
MTSLTDVCSL NCCRSWSSLP PPVSGGSLTS KNPRYLITYS PAHRKCNRWR FRCSIAKDSP  60
ITPPISNEFN SQPLLDCVIV GAGISGLCIA QALATKHASV SPDVIVTEAR DRVGGNISTV  120
ERDGYLWEEG PNSFQPSDAM LTMVVDSGLK DDLVLGDPTA PRFVLWGGDL KPVPSKPADL  180
PFFDLMSFPG KLRAGFGALG FRPSPPDREE SVEEFVRRNL GDEVFERLIE PFCSGVYAGD  240
PSKLSMKAAF GKVWNLEQNG GSIVGGAFKA IQDRKNSQKP PRDPRLPKPK GQTVGSFRKG  300
QAMLPNAIST RLGSRVKLCW KLTSISKLEN RGYNLTYETP QGFESLQTKT IVMTVPSYVA  360
SDLLRPLSLG AADALSKFYY PPVAAVSISY PKDAIRADRL IDGQLKGFGQ LHPRSQGVET  420
LGTIYSSSLF PNRAPPGRVL LLNYIGGATN PEILSKTEGE IVDAVDRDLR TMLIRRDAED  480
PLTLGVRVWP RAIPQFLIGH YDILDSAKAA LSSGGFQGMF LGGNYVSGVA LGKCVEAAYD  540
VAAEVMNFLS QGVYK                                                  555

SEQ ID NO: 15          moltype = DNA  length = 1689
FEATURE                Location/Qualifiers
source                 1..1689
                       mol_type = other DNA
                       organism = Spinacia oleracea
SEQUENCE: 15
atgagcgcta tggcgttatc gagtacaatg gccctttcgt tgccgcaatc ttctatgtca  60
ttatcccatt gtaggcacaa ccgtatcacc attttgattc catcttcgtc gcttcgaaga  120
cgaggaggaa gctctatccg ctgctctaca atctcaacct ctaattccgc ggctgcagcc  180
aattaccaga acaaaaacat aggcacaaac ggagttgacg gcggcggagg cggaggaggt  240
gtgttagact gtgtgattgt aggaggtgga atcagtggac tttgcattgc acaggctcta  300
tctactaaat actccaacct ctccacgaat ttcattgtca ccgaggctaa ggatcgagtt  360
ggcgggaaca tcactaccat ggaagctgat gggtatttat gggaagaggg tcctaatagc  420
tttcagccat ctgatgcagt gctcaccatg gctgttgaca gtggtttgaa agaggaattg  480
gtgctgggag atcccaattc gcctcgcttt gtgctgtgga atggcaaatt aaggcctgta  540
ccttccaagc tcactgacct ccctttcttt gatctcatga gcttccctgg aaagattagg  600
gctggtcttg gtgctcttgg cttacgacca tctcctccgg ctcatgagga atccgttgaa  660
caatttgtcc gtcgtaatct tggtgatgag gtctttgaac gcttgatcga accttttgt  720
tcaggtgtgt atgctggtga tccttccaag ttgagtatga aagctgcttt tggcagggtt  780
tgggtcttgg agcaaaaggg tggtagtatc attggtggca ccctcaaaac aatccaggaa  840
agaaaggata atcctaagcc acctcgagac ccgcgcctcc ccaaaccaaa gggccagaca  900
gttggatcct tcaggaaagg actgagtatg ttgccaaccg ccatttctga aaggcttggc  960
aacaaagtga aagtatcatg gaccctttct ggtattgcta agtcgtcgaa cggagagtat  1020
aatctgactt atgaaacacc agatggactg gtttccgtta ggaccaaaag tgttgtgatg  1080
actgtcccgt catatgttgc aagtagcctc cttcgtccac tttcagatgt cgccgcagaa  1140
tctctttcaa aatttcatta tccaccagtt gcagctgtgt cactttccta tcctaaagaa  1200
gcaattagat cagagtgctt gattgacggt gaacttaaag gattcgggca attacattcc  1260
cgcagtcaag gtgtggaaac cttgggaaca atttatagtt catctctttt ccctgggcga  1320
gcaccacctg gtaggacctt gattttgaac tacattggag gtgatactaa ccctggcata  1380
ttagacaaga cgaaagatga actagctgaa gcagttgaca gggatttgag aagaattctc  1440
ataaacccta atgcaaaagc tccccgggtt ttgggtgtga gagtatggcc acaagcaatt  1500
ccccaatttt taattggcca ctttgatctg ctcgatgcag caaaagctgc tttgactgat  1560
ggtggacaca aaggattgtt tcttggtgga aactatgtat caggtgttgc tttgggccga  1620
tgtatagagg gtgcttatga atctgcagcc gaggttgtag atttctgtc acagtactcg  1680
gataaatag                                                         1689

SEQ ID NO: 16          moltype = AA  length = 562
```

```
FEATURE                 Location/Qualifiers
source                  1..562
                        mol_type = protein
                        organism = Spinacia sp.
SEQUENCE: 16
MSAMALSSTM ALSLPQSSMS LSHCRHNRIT ILIPSSSLRR RGGSSIRCST ISTSNSAAAA  60
NYQNKNIGTN GVDGGGGGGG VLDCVIVGGG ISGLCIAQAL STKYSNLSTN FIVTEAKDRV  120
GGNITTMEAD GYLWEEGPNS FQPSDAVLTM AVDSGLKEEL VLGDPNSPRF VLWNGKLRPV  180
PSKLTDLPFF DLMSFPGKIR AGLGALGLRP SPPAHEESVE QFVRRNLGDE VFERLIEPFC  240
SGVYAGDPSK LSMKAAFGRV WVLEQKGGSI IGGTLKTIQE RKDNPKPPRD PRLPKPKGQT  300
VGSFRKGLSM LPTAISERLG NKVKVSWTLS GIAKSSNGEY NLTYETPDGL VSVRTKSVVM  360
TVPSYVASSL LRPLSDVAAE SLSKFHYPPV AAVSLSYPKE AIRSECLIDG ELKGFGQLHS  420
RSQGVETLGT IYSSSLFPGR APPGRTLILN YIGGDTNPGI LDKTKDELAE AVDRDLRRIL  480
INPNAKAPRV LGVRVWPQAI PQFLIGHFDL LDAAKAALTD GGHKGLFLGG NYVSGVALGR  540
CIEGAYESAA EVVDFLSQYS DK                                         562

SEQ ID NO: 17           moltype = DNA  length = 1596
FEATURE                 Location/Qualifiers
source                  1..1596
                        mol_type = other DNA
                        organism = Spinacia oleracea
SEQUENCE: 17
atggtaatac taccggtttc ccagctatca actaatctgg gtttatcgct ggtttcaccc  60
accaagaaca acccagttat gggcaacgtt tctgagcgaa atcaagtcaa tcaacccatt  120
tctgctaaaa gggttgctgt tgttggtgct ggtgttagtg gacttgctgc ggcgtataag  180
ctaaaatcga atggcttgaa tgtgacattg tttgaagctg atagtagagc tggtgggaaa  240
ctcaaaactg ttgtaaagga tggtttgatt tgggatgaag ggcaaatac catgacagag  300
agcgatgagg aggtcacgag tttgtttgat gatctcggga ttcgtgagaa gctacagcta  360
ccaatttcac aaaacaaaag atacattgcc agagatggtc ttcctgtgct gttaccttca  420
aatccagttg cgctcctgaa gagcaatatc ctttcagcaa aatctaagct acaaattatg  480
ttggaacctt ttctttggaa aaaacacaat ggtgctaagg tttctgacga gaatgcccaa  540
gaaagtgtgg ctgagttttt tgagcggcat tttgggaaag agtttgttga ttatttaatt  600
gatccttttg tcgcgggtac aagtggtgga gatcctcaat ctctttctat gcgtcatgca  660
tttccagaat tatggaatat tgagaacagg tttggttcag tgatttctgg attcattcag  720
tctaaactgt catccaagaa ggaaaagggt ggagaaaagc aatcttctaa taagaagcca  780
cgtgtacgtg gttcgtttc ttttcagggt ggaatgcaga cactagttga cactatatgc  840
aaagagtttg gtgaagatga actcaaactc cagtctgagg ttctttcatt gtcatacagc  900
cataatggaa gccttacatc agagaattgg tcagtgtctt ctatgtcaaa cagcaccatc  960
caagatcaac catatgatgc tgtcgttgtg accgccccaa tcaataatgt caaagaactg  1020
aagattatga aagtggaaaa cccattttct cttgacttca ttccagaggt gagctgtcta  1080
cccctctctg ttattattac tacattcaag aagaccaatg tgaagagacc tcttgagggt  1140
tttggtgttc ttgtaccctc taatgagcaa cataatgggc tgaagactct tggtactttg  1200
ttttcctcaa tgatgtttcc tgatcgtgct ccctctgatg tgtatctata cactaccttt  1260
gttggaggta gcagaaatag agaacttgca aaagcttcaa cggatgaact gaagcaaata  1320
gtttcttctg acctccagca gctgttgggc accgagggcg aacctacttt tgtgaatcat  1380
ttttactgga gcaaagcatt ccctctttat ggacgcaatt acgactcagt tcttagagca  1440
atagagaaga tggaaaggga ccttcctgga ctttttacg caggtaacca taagggtgga  1500
ctgtctgtgg gaaagtcaat agcctctgga tacaaagctg ccgagcttgc gatatcctat  1560
ctcgagtcta acaagatgac cgaggagact atataa                           1596

SEQ ID NO: 18           moltype = AA  length = 531
FEATURE                 Location/Qualifiers
source                  1..531
                        mol_type = protein
                        organism = Spinacia sp.
SEQUENCE: 18
MVILPVSQLS TNLGLSLVSP TKNNPVMGNV SERNQVNQPI SAKRVAVVGA GVSGLAAAYK  60
LKSNGLNVTL FEADSRAGGK LKTVVKDGLI WDEGANTMTE SDEEVTSLFD DLGIREKLQL  120
PISQNKRYIA RDGLPVLLPS NPVALLKSNI LSAKSKLQIM LEPFLWKKHN GAKVSDENAQ  180
ESVAEFFERH FGKEFVDYLI DPFVAGTSGG DPQSLSMRHA FPELWNIENR FGSVISGFIQ  240
SKLSSKKEKG GEKQSSNKKP RVRGSFSFQG GMQTLVDTIC KEFGEDELKL QSEVLSLSYS  300
HNGSLTSENW SVSSMSNSTI QDQPYDAVVV TAPINNVKEL KIMKVENPFS LDFIPEVSCL  360
PLSVIITTFK KTNVKRPLEG FGVLVPSNEQ HNGLKTLGTL FSSMMFPDRA PSDVYLYTTF  420
VGGSRNRELA KASTDELKQI VSSDLQQLLG TEGEPTFVNH FYWSKAFPLY GRNYDSVLRA  480
IEKMERDLPG LFYAGNHKGG LSVGKSIASG YKAAELAISY LESNKMTEET I          531

SEQ ID NO: 19           moltype = DNA  length = 1674
FEATURE                 Location/Qualifiers
source                  1..1674
                        mol_type = other DNA
                        organism = Solanum tuberosum
SEQUENCE: 19
atgacaacaa cggccgtcgc caaccatcct agcattttca ctcaccggtc gccgctgccg  60
tcgccgtcgt cctcctcctc atcgccgtca tttttatttt taaaccgtac gaatttcatt  120
ccttactttt ccacctccaa gcgcaatagt gtcaattgca atggctggag aacacgatgt  180
tccgttgcca aggattatac agttcctccc tcggaagtcg acggtaatca gttcccggag  240
ctggattgtg tggtagttgg agcaggaatt agtggactct gcattgctaa ggtgatttcg  300
gctaattatc ccaatttgat ggtgacggag gcgagggatc gtgccggtgg aaacataacg  360
acggtggaaa gagatggata cttatgggaa gaaggtccta acagtttcca gccttcggat  420
```

-continued

```
cctatgttga caatggctgt agattgtgga ttgaaggatg atttggtgtt gggagatcct  480
gatgcgcctc gctttgtctt gtggaaggat aaactaaggc ctgttcccgg caagctcact  540
gatcttccct tctttgattt gatgagtatc cctggcaagc tcagagctgg ttttggtgcc  600
attggccttc gcccttcacc tccaggttat gaggaatcag ttgagcagtt cgtgcgtcgt  660
aatcttggtg cagaagtctt tgaacgtttg attgaaccat tttgttctgg tgtttacgcc  720
ggtgacccct caaaattgat tatgaaagca gcatttggga aagtgtggaa gctagaacaa  780
actggtggta gcattattgg gggaaccttt aaagcaatta aggagagatc cagtaaccct  840
aaaccgcctc gtgatccgcg tttaccaaca ccaaaaggac aaactgttgg atcatttagg  900
aagggtctga gaatgctgcc ggatgcaatt tgtgaaagac tgggaagcaa agtaaaacta  960
tcatggaagc tttctagcat tacaaagtca gaaaaaggag gatatctctt gacatacgag  1020
acaccagaag gagtagtttc tctgcgaagt cgaagcattg tcatgactgt tccatcctat  1080
gtagcaagca acatattacg ccctctttcg gtcgctgcag cagatgcact ttcaagtttc  1140
tactatcccc cagtagcagc agtgacaatt tcatatcctc aagaggctat tcgtgatgag  1200
cgtctggttg atggtgaact aaagggattt gggcagttgc atccacgttc acagggagtg  1260
gaaacactag gaacaatata tagttcatca ctctttccta accgtgctcc aaatggccgg  1320
gtgctactct tgaactacat tggaggagca acaaatactg aaattgtgtc taagacggag  1380
agccaacttg tggaagcagt tgaccgtgac ctcagaaaaa tgcttataaa acccaaagca  1440
caagatccct ttgttacggg tgtgcgagta tggccacaag ctatcccaca gtttttggtc  1500
ggacatctgg atacactagg tactgcaaaa actgctctaa gtgataatgg gcttgacggg  1560
ctattccttg ggggtaatta tgtgtctggt gtagcattgg gaaggtgtgt tgaaggtgct  1620
tatgaaatag catctgaggt aactggattt ctgtctcagt atgcatacaa atga        1674

SEQ ID NO: 20          moltype = AA  length = 557
FEATURE                Location/Qualifiers
source                 1..557
                       mol_type = protein
                       organism = Solanum tuberosum
SEQUENCE: 20
MTTTAVANHP SIFTHRSPLP SPSSSSSSPS FLFLNRTNFI PYFSTSKRNS VNCNGWRTRC  60
SVAKDYTVPP SEVDGNQFPE LDCVVVGAGI SGLCIAKVIS ANYPNLMVTE ARDRAGGNIT  120
TVERDGYLWE EGPNSFQPSD PMLTMAVDCG LKDDLVLGDP DAPRFVLWKD KLRPVPGKLT  180
DLPFFDLMSI PGKLRAGFGA IGLRPSPPGY EESVEQFVRR NLGAEVFERL IEPFCSGVYA  240
GDPSKLIMKA AFGKVWKLEQ TGGSIIGGTF KAIKERSSNP KPPRDPRLPT PKGQTVGSFR  300
KGLRMLPDAI CERLGSKVKL SWKLSSITKS EKGGYLLTYE TPEGVVSLRS RSIVMTVPSY  360
VASNILRPLS VAAADALSSF YYPPVAAVTI SYPQEAIRDE RLVDGELKGF GQLHPRSQGV  420
ETLGTIYSSS LFPNRAPNGR VLLLNYIGGA TNTEIVSKTE SQLVEAVDRD LRKMLIKPKA  480
QDPFVTGVRV WPQAIPQFLV GHLDTLGTAK TALSDNGLDG LFLGGNYVSG VALGRCVEGA  540
YEIASEVTGF LSQYAYK                                                 557

SEQ ID NO: 21          moltype = DNA  length = 1608
FEATURE                Location/Qualifiers
source                 1..1608
                       mol_type = other DNA
                       organism = Zea mays
SEQUENCE: 21
atggtcgccg ccacagccac cgccatggcc accgctgcat cgccgctact caacgggacc  60
cgaatacctg cgcggctccg ccatcgagga ctcagcgtgc gctgcgctgc tgtggcgggc  120
ggcgcggccg aggcaccggc atccaccggc gcgcggctgt ccgcggactg cgtcgtggtg  180
ggcggaggca tcagtggcct ctgcaccgcg caggcgctgg ccacgcggca cggcgtcggg  240
gacgtgcttg tcacggaggc ccgcgcccgc cccggcggca acattaccac cgtcgagcgc  300
cccgaggaag ggtacctctg ggaggagggt cccaacagct tccagccctc cgaccccgtt  360
ctcaccatgg ccgtggacag cggactgaag gatgacttgg tttttgggga cccaaacgcg  420
ccgcgtttcg tgctgtggga ggggaagctg aggcccgtgc catccaagcc cgccgacctc  480
ccgttcttcg atctcatgag catcccaggg aagctcaggg ccggtctagg cgcgcttggc  540
atccgcccgc ctcctccagg ccgcgaagag tcagtggagg agttcgtgcg ccgcaacctc  600
ggtgctgagg tctttgagcg cctcattgag cctttctgct caggtgtcta tgctggtgat  660
ccttctaagc tcagcatgaa ggctgcattt gggaaggttt ggcggttgga agaaactgga  720
ggtagtatta ttggtggaac catcaagaca attcaggaga ggagcaagaa tccaaaacca  780
ccgagggatg cccgccttcc gaagccaaaa gggcagacag ttgcatcttt caggaagggt  840
cttgccatgc ttccaaatgc cattacatcc agcttgggta gtaaagtcaa actatcatgg  900
aaactcacga gcattacaaa atcagatgac aagggatatg ttttggagta tgaaacgcca  960
gaaggggttg tttcggtgca ggctaaaagt gttatcatga ctattccatc atatgttgct  1020
agcaacattt tgcgtccact ttcaagcgat gctgcagatg ctctatcaag attctattat  1080
ccaccggttg ctgctgtaac tgtttcgtat ccaaaggaag caattagaaa agaatgctta  1140
attgatgggg aactccaggg ctttggccag ttgcatccac gtagtcaagg agttgagaca  1200
ttaggaacaa tatacagttc ctcactcttt ccaaatcgtg ctcctgacgg tagggtgtta  1260
cttctaaact acataggagg tgctacaaac acaggaattg tttccaagac tgaaagtgag  1320
ctggtcgaag cagttgaccg tgacctccga aaaatgctta taaattctac agcagtggac  1380
cctttagtcc ttggtgttcg agtttggcca caagccatac ctcagttcct ggtaggacat  1440
cttgatcttc tggaagccgc aaaagctgcc ctggaccgag gtggctacga tgggctgttc  1500
ctaggaggga actatgttgc aggagttgcc ctgggcagat gcgttgaggg cgcgtatgaa  1560
agtgcctcgc aaatatctga cttcttgacc aagtatgcct acaagtga              1608

SEQ ID NO: 22          moltype = AA  length = 535
FEATURE                Location/Qualifiers
source                 1..535
                       mol_type = protein
                       organism = Zea mays
SEQUENCE: 22
```

-continued

```
MVAATATAMA TAASPLLNGT RIPARLRHRG LSVRCAAVAG GAAEAPASTG ARLSADCVVV  60
GGGISGLCTA QALATRHGVG DVLVTEARAR PGGNITTVER PEEGYLWEEG PNSFQPSDPV  120
LTMAVDSGLK DDLVFGDPNA PRFVLWEGKL RPVPSKPADL PFFDLMSIPG KLRAGLGALG  180
IRPPPPGREE SVEEFVRRNL GAEVFERLIE PFCSGVYAGD PSKLSMKAAF GKVWRLEETG  240
GSIIGGTIKT IQERSKNPKP PRDARLPKPK GQTVASFRKG LAMLPNAITS SLGSKVKLSW  300
KLTSITKSDD KGYVLEYETP EGVVSVQAKS VIMTIPSYVA SNILRPLSSD AADALSRFYY  360
PPVAAVTVSY PKEAIRKECL IDGELQGFGQ LHPRSQGVET LGTIYSSSLF PNRAPDGRVL  420
LLNYIGGATN TGIVSKTESE LVEAVDRDLR KMLINSTAVD PLVLGVRVWP QAIPQFLVGH  480
LDLLEAAKAA LDRGGYDGLF LGGNYVAGVA LGRCVEGAYE SASQISDFLT KYAYK       535

SEQ ID NO: 23           moltype = DNA  length = 1635
FEATURE                 Location/Qualifiers
source                  1..1635
                        mol_type = other DNA
                        organism = Zea mays
SEQUENCE: 23
atgctcgctt tgactgcctc agcctcatcc gcttcgtccc atccttatcg ccacgcctcc  60
gcgcacactc gtcgcccccg cctacgtgcg gtcctcgcga tggcgggctc cgacgacccc  120
cgtgcagcgc ccgccagatc ggtcgccgtc gtcggcgccg gggtcagcgg gctcgcggcg  180
gcgtacaggc tcagacagag cggcgtgaac gtaacggtgt tcgaagcggc cgacagggcg  240
ggaggaaaga tacggaccaa ttccgagggc gggtttgtct gggatgaagg agctaacacc  300
atgacagaag gtgaatggga ggccagtaga ctgattgatg atcttggtct acaagacaaa  360
cagcagtatc ctaactccca acacaagcgt tacattgtca aagatggagc accagcactg  420
attccttcgg atcccatttc gctaatgaaa agcagtgttc tttcgacaaa atcaaagatt  480
gcgttatttt ttgaaccatt tctctacaag aaagctaaca caagaaactc tggaaaagtg  540
tctgaggagc acttgagtga gagtgttggg agcttctgtg aacgccactt tggaagagaa  600
gttgttgact attttgttga tccatttgta gctggaacaa gtgcaggaga tccagagtca  660
ctatctattc gtcatgcatt cccagcattg tggaatttgg aaagaaagta tggttcagtt  720
attgttggtg ccatcttgtc taagctagca gctaaaggtg atccagtaaa gacaagacat  780
gattcatcag ggaaaagaag gaatagacga gtgtcgtttt catttcatgg tggaatgcag  840
tcactaataa atgcacttca caatgaagtt ggagatgata atgtgaagct tggtacagaa  900
gtgttgtcat tggcatgtac atttgatgga gttcctgcac taggcaggtg gtcaatttct  960
gttgattcga aggatagcgg tgacaaggac cttgctagta accaaacctt tgatgctgtt  1020
ataatgacag ctccattgtc aaatgtccgg aggatgaagt tcaccaaagg tggagctccg  1080
gttgttcttg actttcttcc taagatggat tatctaccac tatctctcat ggtgactgct  1140
tttaagaagg atgatgtcaa gaaacctctg gaaggatttg gggtcttaat accttacaag  1200
gaacagcaaa aacatggtct gaaaaccctt gggactctct tttcctcaat gatgttccca  1260
gatcgagctc ctgatgacca atatttatat acaacatttg ttgggggtag ccacaataga  1320
gatcttgctg gagctccaac gtctattctg aaacaacttg tgacctctga ccttaaaaaa  1380
ctcttgggcg tagaggggca accaactttt gtcaagcatg tatactgggg aaatgctttt  1440
cctttgtatg gccatgatta tagttctgta ttggaagcta tagaaaagat ggagaaaaac  1500
cttccagggt tcttctacgc aggaaatagc aaggatgggc ttgctgttgg aagtgttata  1560
gcttcaggaa gcaaggctgc tgaccttgca atctcatatc ttgaatctca caccaagcat  1620
aataattcac attga                                                    1635

SEQ ID NO: 24           moltype = AA  length = 544
FEATURE                 Location/Qualifiers
source                  1..544
                        mol_type = protein
                        organism = Zea mays
SEQUENCE: 24
MLALTASASS ASSHPYRHAS AHTRRPRLRA VLAMAGSDDP RAAPARSVAV VGAGVSGLAA  60
AYRLRQSGVN VTVFEAADRA GGKIRTNSEG GFVWDEGANT MTEGEWEASR LIDDLGLQDK  120
QQYPNSQHKR YIVKDGAPAL IPSDPISLMK SSVLSTKSKI ALFFEPFLYK KANTRNSGKV  180
SEEHLSESVG SFCERHFGRE VVDYFVDPFV AGTSAGDPES LSIRHAFPAL WNLERKYGSV  240
IVGAILSKLA AKGDPVKTRH DSSGKRRNRR VSFSFHGGMQ SLINALHNEV GDDNVKLGTE  300
VLSLACTFDG VPALGRWSIS VDSKDSGDKD LASNQTFDAV IMTAPLSNVR RMKFTKGGAP  360
VVLDFLPKMD YLPLSLMVTA FKKDDVKKPL EGFGVLIPYK EQQKHGLKTL GTLFSSMMFP  420
DRAPDDQYLY TTFVGGSHNR DLAGAPTSIL KQLVTSDLKK LLGVEGQPTF VKHVYWGNAF  480
PLYGHDYSSV LEAIEKMEKN LPGFFYAGNS KDGLAVGSVI ASGSKAADLA ISYLESHTKH  540
NNSH                                                                544

SEQ ID NO: 25           moltype = DNA  length = 1692
FEATURE                 Location/Qualifiers
source                  1..1692
                        mol_type = other DNA
                        organism = Chlamydomonas reinhardtii
SEQUENCE: 25
atgatgttga cccagactcc tgggaccgcc acggcttcta gccggcggtc gcagatccgc  60
tcggctgcgc acgtctccgc caaggtcgcg cctcggccca cgccattctc ggtcgcgagc  120
cccgcgaccg ctgcgagccc cgcgaccgcg gcggcccgcc gcacactcca ccgcactgct  180
gcggcggcca ctggtgctcc cacggcgtcc ggagccggcg tcgccaagac gctcgacaat  240
gtgtatgacg tgatcgtggt cggtggaggt ctctcgggcc tggtgaccgg ccaggccctg  300
gcggctcagc acaaaattca gaacttcctt gttacggagg ctcgcgagcg cgtcggcggc  360
aacattacgt ccatgtcggg cgatggctac gtgtgggagg agggcccgaa cagcttccag  420
cccaacgata gcatgctgca gattgcggtg gactctggct gcgagaagga ccttgtgttc  480
ggtgacccca cggctccccg cttcgtgtgg tgggagggca agctgcgccc cgtgccctcg  540
ggcctggacg ccttcacctt cgacctcatg tccatccccg gcaagatccg cgccgggctg  600
ggcgccatcg gcctcatcaa cggagccatg ccctccttcg aggagagtgt ggagcagttc  660
```

-continued

```
atccgccgca acctgggcga tgaggtgttc ttccgcctga tcgagccctt ctgctccggc  720
gtgtacgcgg gcgacccctc caagctgtcc atgaaggcgg ccttcaacag gatctggatt  780
ctggagaaga acggcggcag cctggtggga ggtgccatca agctgttcca ggaacgccag  840
tccaacccgg ccccgccgcg ggacccgcgc ctgccgccca agcccaaggg ccagacggtg  900
ggctcgttcc gcaagggcct gaagatgctg ccggacgcca ttgagcgcaa catccccgac  960
aagatccgcg tgaactggaa gctggtgtct ctgggccgcg aggcggacgg gcggtacggg  1020
ctggtgtacg acacgcccga gggccgtgtc aaggtgtttg cccgcgccgt ggctctgacc  1080
gcgcccagct acgtggtggc ggacctggtc aaggagcagg cgcccgccgc cgccgaggcc  1140
ctgggctcct tcgactaccc gccggtgggc gccgtgacgc tgtcgtaccc gctgagcgcc  1200
gtgcgggagg agcgcaaggc ctcggacggg tccgtgccgg gcttcggtca gctgcacccg  1260
cgcacgcagg gcatcaccac tctgggcacc atctacagct ccagcctgtt ccccggccgc  1320
gcgcccgagg gccacatgct gctgctcaac tacatcggcg gcaccaccaa ccgcggcatc  1380
gtcaaccaga ccaccgagca gctggtggag caggtggaca aggacctgcg caacatggtc  1440
atcaagcccg acgcgcccaa gccccgtgtg gtgggcgtgc gcgtgtggcc gcgcgccatc  1500
ccgcagttca acctgggcca cctggagcag ctggacaagg cgcgcaaggc gctggacgcg  1560
gcggggctgc agggcgtgca cctgggggc aactacgtca gcggtgtggc cctgggcaag  1620
gtggtggagc acggctacga gtccgcagcc aacctggcca agagcgtgtc caaggccgca  1680
gtcaaggcct aa                                                      1692

SEQ ID NO: 26          moltype = AA  length = 563
FEATURE                Location/Qualifiers
source                 1..563
                       mol_type = protein
                       organism = Chlamydomonas sp.
SEQUENCE: 26
MMLTQTPGTA TASSRRSQIR SAAHVSAKVA PRPTPFSVAS PATAASPATA AARRTLHRTA  60
AAATGAPTAS GAGVAKTLDN VYDVIVVGGG LSGLVTGQAL AAQHKIQNFL VTEARERVGG  120
NITSMSGDGY VWEEGPNSFQ PNDSMLQIAV DSGCEKDLVF GDPTAPRFVW WEGKLRPVPS  180
GLDAFTFDLM SIPGKIRAGL GAIGLINGAM PSFEESVEQF IRRNLGDEVF FRLIEPFCSG  240
VYAGDPSKLS MKAAFNRIWI LEKNGGSLVG GAIKLFQERQ SNPAPPRDPR LPPKPKGQTV  300
GSFRKGLKML PDAIERNIPD KIRVNWKLVS LGREADGRYG LVYDTPEGRV KVFARAVALT  360
APSYVVADLV KEQAPAAAEA LGSFDYPPVG AVTLSYPLSA VREERKASDG SVPGFGQLHP  420
RTQGITTLGT IYSSSLFPGR APEGHMLLLN YIGGTTNRGI VNQTTEQLVE QVDKDLRNMV  480
IKPDAPKPRV VGVRVWPRAI PQFNLGHLEQ LDKARKALDA AGLQGVHLGG NYVSGVALGK  540
VVEHGYESAA NLAKSVSKAA VKA                                          563

SEQ ID NO: 27          moltype = DNA  length = 1734
FEATURE                Location/Qualifiers
source                 1..1734
                       mol_type = other DNA
                       organism = Polytomella sp.
SEQUENCE: 27
atgtcgagtt ccgcactaag gctattatgc gggcgaacaa gtttctttaa tttatgccaa  60
aaatatcctc cttcctttct gtcacaattg tcgaccttaa atttctcaac ccattcgcct  120
ttcgatagca cttatgatgt cgtcgtcgtt ggtgccggaa tctctgggtt gtctactgcc  180
caagcactta gcattcaaca taagatcgat aatgttctgg ttactgaagc tgatcatcgt  240
gtaggcggta aaattacgac gaaaaggaat aaagatttcc tgtgggagga gggtccaaat  300
agttgcctaa tgaacgacgc tttatatcgc gctgcccgag atgccggcgt ggaatccaaa  360
attctatcgg cggatccaaa attaccacgt tggattctgt ggggtcgtcg tttgcgtgtg  420
gcccccattg gaagctacgc tttaaaatcc gaccttttat ctacccaagg cctactccgt  480
gccatccgag gagtcacagg ttttggtgtg tcaccggctc cacctaaggg tcaggaggag  540
agcgtggagg gctttgttcg acggacctta ggagacgaga tttttgagcg actcgttgag  600
ccctttttgct ccggggttta tgcgggggat cctagcaaat tgtccatgcg tgctgctttc  660
ggaaaacttg tggaattcga agagacgggt gatggtagct tacttcgcgg cgtctttcgt  720
tacgtaatga acaaacgacg cgaaagaagg acgggcgggg cgaaagacgg ggacacggtc  780
cctttgaacg agacggccaa ggcacccaaa tcatcctctg gcccaacagt atcgtctttc  840
gaggggggaa tcgagatcct gcccaaggcc attgcgcaaa agctgggtga tcgagttcgt  900
cttggcctac gactcgtgcg catcgatccc acgcagctcg cggatggtac gacagcgtac  960
cgtctgtcgt accgtcggat gagtcatcaa ggcgatgacg actcgagtcg tacggcaggt  1020
gctgtaccgc gtacggcgga gggggatgtc gcggcggggg acgaggacgc cgtggtggag  1080
gtggtggcga agaaggtcgt gctgacgacg ccggcattcg acgccgcgga catcttgtcg  1140
cgttccggct tggtggcggc ggcgaacccg ttgaaggagg tggattaccc gccagtagcg  1200
ttggtcgttc tttcgtacga cgtcgactcg atttccgcca tacaccgcgt gagtcacgtg  1260
gctcatggcc tcagcggctt tggccaactc caccctcgcc cagagggtct ccgtacatta  1320
ggaaccattt acggcagtac attatttccc aaccgttccc ccgtagctcg tacgacgctt  1380
ttaaatttcg ttggtggatc caccgaccgt gcagtggggt ccgcggatcc aatggctttg  1440
gcgatggagg tggatctgga tctgaaaaag agcgggttga tccgagaggg agctgcgaag  1500
ccagaagtcc tcggggtgaa agtatatcca aaggctattc ctcagtttga tattggtcat  1560
ttggatcgag tggaaaaggc caaaatgatg ttaaagaacg aaagggggggg tgcagattgg  1620
agtggggtca aattggcggg aaattatgtg tgcggcgtcg cagtgggcag atgcatagaa  1680
tttggattcg aaattgcgga gaacttggcg caggaattgg cgagaaaaaa atag        1734

SEQ ID NO: 28          moltype = AA  length = 577
FEATURE                Location/Qualifiers
source                 1..577
                       mol_type = protein
                       organism = Polytomella sp.
SEQUENCE: 28
MSSSALRLLC GRTSFFNLCQ KYPPSFLSQL STLNFSTHSP FDSTYDVVVV GAGISGLSTA  60
```

-continued

```
QALSIQHKID NVLVTEADHR VGGKITTKRN KDFLWEEGPN SCLMNDALYR AARDAGVESK  120
ILSADPKLPR WILWGRRLRV APIGSYALKS DLLSTQGLLR AIRGVTGFGV SPAPPKGQEE  180
SVEGFVRRTL GDEIFERLVE PFCSGVYAGD PSKLSMRAAF GKLVEFEETG DGSLLRGVFR  240
YVMNKRRERR TGGAKDGDTV PLNETAKAPK SSSGPTVSSF EGGIEILPKA IAQKLGDRVR  300
LGLRLVRIDP TQLADGTTAY RLSYRRMSHQ GDDDSSRTAG AVPRTAEGDV AAGDEDAVVE  360
VVAKKVVLTT PAFDAADILS RSGLVAAANP LKEVDYPPVA LVVLSYDVDS ISAIHRVSHV  420
AHGLSGFGQL HPRPEGLRTL GTIYGSTLFP NRSPVARTTL LNFVGGSTDR AVGSADPMAL  480
AMEVDLDLKK SGLIREGAAK PEVLGVKVYP KAIPQFDIGH LDRVEKAKMM LKNERGGADW  540
SGVKLAGNYV CGVAVGRCIE FGFEIAENLA QELARKK                          577

SEQ ID NO: 29           moltype = DNA  length = 1635
FEATURE                 Location/Qualifiers
source                  1..1635
                        mol_type = other DNA
                        organism = Sorghum bicolor
SEQUENCE: 29
atgctcgctc ggactgccac ggtctcctcc acttcgtccc actcccatcc ttatcgcccc  60
acctccgctc gcagtctccg cctacgtccg gtcctcgcga tggcgggctc cgacgactcc  120
cgcgcagctc ccgccaggtc ggtcgccgtc gtcggcgccg gggtcagcgg gctcgtggcg  180
gcgtacaggc tcaggaagag cggcgtgaat gtgacggtgt tcgaggcggc cgacagggcg  240
ggaggaaaga tacggaccaa ttccgagggc gggtttctct gggatgaagg agcgaacacc  300
atgacagaag gtgaattgga ggccagtaga ctgatagatg atctcggtct acaagacaaa  360
cagcagtatc ctaactccca acacaagcgt tacattgtca aagatggagc accagcactg  420
attccttcgg atcccatttc gctgatgaaa agcagtgttc tttctacaaa atcaaagatt  480
gcgttatttt ttgaaccatt tctctacaag aaagctaaca caagaaaccc tggaaaagta  540
tctgatgagc atttgagtga gagtgttggg agcttcttgg aacgccactt cggaagagaa  600
gttgttgact atcttattga tccatttgta gctggaacaa gtgcaggaga tccagagtca  660
ctatctattt gtcatgcatt cccagcactg tggaatttgg aaagaaaata tggttcagtt  720
gttgttggtg ccatcttgtc taagctaaca gctaaaggtg atccagtaaa gacaagacgt  780
gattcatcag cgaaaagaag gaatagacgc gtgtcgtttt catttcatgg tggaatgcag  840
tcactaataa atgcacttca caatgaagtt ggagatgata atgtgaagct tggtacagaa  900
gtgttgtcat tggcgtgtac attagatgga gcccctgcac caggcgggtg gtcaatttct  960
gatgattcga aggatgctag tggcaaggac cttgctaaaa accaaacctt tgatgctgtt  1020
ataatgacag ctccattgtc aaatgtccag aggatgaagt tcacaaaagg tggagctcct  1080
tttgttctag actttcttcc taaggtggat tatctaccac tatctctcat ggtgactgct  1140
tttaagaagg aagatgtcaa gaaacctctg gaaggatttg gcgtcttaat accctacaag  1200
gaacagcaaa aacatggtct aaaaaccctt gggactctct tctcctcaat gatgttccca  1260
gatcgagctc ctgacgacca atatttatat acaacatttg ttgggggtag ccacaataga  1320
gatcttgctg gagctccaac gtctattctg aaacaacttg tgacctctga ccttaaaaaa  1380
ctcttaggcg tacaggggca accaactttt gtcaagcata tatactgggg aaatgctttt  1440
cctttgtatg gtcatgatta caattctgta ttggaagcta tagaaaagat ggagaaaaat  1500
cttccagggt tcttctacgc aggaaataac aaggatgggc ttgctgttgg gagtgttata  1560
gcttcaggaa gcaaggctgc tgaccttgca atctcgtatc ttgaatctca caccaagcat  1620
aataatttac attga                                                  1635

SEQ ID NO: 30           moltype = AA  length = 544
FEATURE                 Location/Qualifiers
source                  1..544
                        mol_type = protein
                        organism = Sorghum sp.
SEQUENCE: 30
MLARTATVSS TSSHSHPYRP TSARSLRLRP VLAMAGSDDS RAAPARSVAV VGAGVSGLVA  60
AYRLRKSGVN VTVFEAADRA GGKIRTNSEG GFLWDEGANT MTEGELEASR LIDDLGLQDK  120
QQYPNSQHKR YIVKDGAPAL IPSDPISLMK SSVLSTKSKI ALFFEPFLYK KANTRNPGKV  180
SDEHLSESVG SFFERHFGRE VVDYLIDPFV AGTSAGDPES LSICHAFPAL WNLERKYGSV  240
VVGAILSKLT AKGDPVKTRR DSSAKRRNRR VSFSFHGGMQ SLINALHNEV GDDNVKLGTE  300
VLSLACTLDG APAPGGWSIS DDSKDASGKD LAKNQTFDAV IMTAPLSNVQ RMKFTKGGAP  360
FVLDFLPKVD YLPLSLMVTA FKKEDVKKPL EGFGVLIPYK EQQKHGLKTL GTLFSSMMFP  420
DRAPDDQYLY TTFVGGSHNR DLAGAPTSIL KQLVTSDLKK LLGVQGQPTF VKHIYWGNAF  480
PLYGHDYNSV LEAIEKMEKN LPGFFYAGNN KDGLAVGSVI ASGSKAADLA ISYLESHTKH  540
NNLH                                                              544

SEQ ID NO: 31           moltype = DNA  length = 1017
FEATURE                 Location/Qualifiers
source                  1..1017
                        mol_type = other DNA
                        organism = Chlorella sp.
SEQUENCE: 31
atggcctcca cagcaacact gcacggcgcg ccctgctgct cggcgcggcc cgtgggccgc  60
cggcatattg cagcaccgag catccagcac aatgggccgc gcctggcggc cagggtgcag  120
cagcggaagg gggcagggga gcggcgctcg gcactgcgtg tgcaggccgt ccaggcccct  180
cccgagaagg cgggggcgag cacagggagc gcagcagacg acagcggcgt ttacgacgtt  240
gtggtcgtgg gcgccggcat ctccggcctc accaccgccc aggcgctgac cacgcagcac  300
agcggcgtgg cgcggcgggt gctggtgacc gagggccgcg accgcgtggg cggcaacatc  360
acctccgtgt ccaacaagga ggaggggctg ctgtgggagg aggggcccaa ctccttccag  420
ccaaacgact ccatcctgca ggccgcggtg gacgccggcg tggcggacca gctggtactg  480
ggcgacccca cggcgccgcg ttttgtgtac tgggacaaga agctgcgccc cacgccctcc  540
ggccccgacg cgctcacgtt cgacctgatg agcatcgtgg gcaagatccg ggcggggctg  600
ggcgcgctgg gcttcaaggc gcccatgcca gactatgagg agagcgtgga gcagtatgtg  660
```

-continued

```
cggcgcaacc tgggggccga ggtgtttgag cgcctgatcg agcccttctg cagcggcgtg  720
tacgccggcg accccaagaa gctgtccatg aaggcggcct ttggcaaggt gtacgacctg  780
gagaagaagg gcggcagcat cgtgggcggc gtgatcaagc tgattcagga gcggcgcgcc  840
aacccgccgc cgccgcgcag cccagcgctg ccgcccaagc ccgcgggcca gacggtgggc  900
tccttccgct ccggcctgcg cacgctgccg gatgccatgg cggcgcggct gggagacgcg  960
gtgcgcacca gctggcagct caaggagctc agcaaggaag ggagaggccta caagtga     1017
```

```
SEQ ID NO: 32          moltype = AA  length = 338
FEATURE                Location/Qualifiers
source                 1..338
                       mol_type = protein
                       organism = Chlorella sp.
SEQUENCE: 32
MASTATLHGA PCCSARPVGR RHIAAPSIQH NGPRLAARVQ QRKGAGERRS ALRVQAVQAP  60
PEKAGASTGS AADDSGVYDV VVVGAGISGL TTAQALTTQH SGVARRVLVT EGRDRVGGNI  120
TSVSNKEEGL LWEEGPNSFQ PNDSILQAAV DAGVADQLVL GDPTAPRFVY WDKKLRPTPS  180
GPDALTFDLM SIVGKIRAGL GALGFKAPMP DYEESVEQYV RRNLGAEVFE RLIEPFCSGV  240
YAGDPKKLSM KAAFGKVYDL EKKGGSIVGG VIKLIQERRA NPPPPRSPAL PPKPAGQTVG  300
SFRSGLRTLP DAMAARLGDA VRTSWQLKEL SKEGEAYK                          338
```

```
SEQ ID NO: 33          moltype = DNA  length = 1611
FEATURE                Location/Qualifiers
source                 1..1611
                       mol_type = other DNA
                       organism = Oryza sativa
SEQUENCE: 33
atggccgccg ccgccgcagc catggccacc gccacctccg ccacggcagc gccgccgctc  60
cgcattcgcg acgccgcgag gaggacccgc cgacgcggcc acgttcgctg cgccgtcgcc  120
agcggcgcgg ccgaggcgcc cgcggcgccc ggggcgcggg tgtcggcgga ctgcgtcgtg  180
gtgggcggcg gcatcagcgg gctctgcacc gcgcaggcgc tggccacaaa gcacggcgtc  240
ggcgacgtgc tcgtcacgga ggcccgcgcc cgccccggcg gcaacatcac caccgccgag  300
cgcgccggcg agggctacct ctgggaggag gggcccaaca gcttccagcc ttccgacccc  360
gtcctcacca tggccgtgga cagcgggctc aaggacgatc tcgtgttcgg ggaccccaac  420
gcgccgcggt tcgtgctgtg ggaggggaag ctaaggccgg tgccgtccaa gcccggcgac  480
ctgccgttct tcgacctcat gagcatcccc ggcaagctca gggccggcct tggcgcgctc  540
ggcgttcgag cgccacctcc agggcgtgag gagtcggtgg aggacttcgt gcggcgcaac  600
ctcggcgcgg aggtctttga gcgcctcatt gagccttttct gctcaggtgt gtatgctggt  660
gatccttcaa agctcagtat gaaggctgca tttgggaagg tgtggaggct ggaggatact  720
ggaggtagca ttattggtgg aaccatcaaa acaatccagg agaggggggaa aaaccccaaa  780
ccgccgaggg atccccgcct tccaacgcca aaggggcaga cagttgcatc tttcaggaag  840
ggtctgacta tgctcccgga tgctattaca tctaggttgg gtagcaaagt caaactttca  900
tggaagttga caagcattac aaagtcagac aacaaaggat atgcattagt gtatgaaaca  960
ccagaagggg tggtctcggt gcaagctaaa actgttgtca tgaccatccc atcatatgtt  1020
gctagtgata tcttgcggcc actttcaagt gatgcagcag atgctctgtc aatattctat  1080
tatccaccag ttgctgctgt aactgtttca tatccaaaag aagcaattag aaaagaatgc  1140
ttaattgacg gagagctcca gggtttcggc cagctgcatc cgcgtagtca gggagttgag  1200
actttaggaa caatatatag ctcatcactc tttccaaatc gtgctccagc tggaagggtg  1260
ttacttctga actacatagg aggttctaca aatacaggga ttgtttccaa gactgaaagt  1320
gagctggtag aagcagttga ccgtgacctc aggaagatgc tgataaatcc taaagcagtg  1380
gacccctttgg tccttggcgt ccgggtatgg ccacaagcca taccacagtt cctcattggc  1440
catcttgatc atcttgaggc tgcaaaatct gccctgggca aaggtggtta tgatggattg  1500
ttcctcggag ggaactatgt tgcaggagtt gccctgggcc gatgcgttga aggtgcatat  1560
gagagtgcct cacaaatatc tgactacttg accaagtacg cctacaagtg a            1611
```

```
SEQ ID NO: 34          moltype = AA  length = 536
FEATURE                Location/Qualifiers
source                 1..536
                       mol_type = protein
                       organism = Oryza sativa
SEQUENCE: 34
MAAAAAAMAT ATSATAAPPL RIRDAARRTR RRGHVRCAVA SGAAEAPAAP GARVSADCVV  60
VGGGISGLCT AQALATKHGV GDVLVTEARA RPGGNITTAE RAGEGYLWEE GPNSFQPSDP  120
VLTMAVDSGL KDDLVFGDPN APRFVLWEGK LRPVPSKPGD LPFFDLMSIP GKLRAGLGAL  180
GVRAPPPGRE ESVEDFVRRN LGAEVFERLI EPFCSGVYAG DPSKLSMKAA FGKVWRLEDT  240
GGSIIGGTIK TIQERGKNPK PPRDPRLPTP KGQTVASFRK GLTMLPDAIT SRLGSKVKLS  300
WKLTSITKSD NKGYALVYET PEGVVSVQAK TVVMTIPSYV ASDILRPLSS DAADALSIFY  360
YPPVAAVTVS YPKEAIRKEC LIDGELQGFG QLHPRSQGVE TLGTIYSSSL FPNRAPAGRV  420
LLLNYIGGST NTGIVSKTES ELVEAVDRDL RKMLINPKAV DPLVLGVRVW PQAIPQFLIG  480
HLDHLEAAKS ALGKGGYDGL FLGGNYVAGV ALGRCVEGAY ESASQISDYL TKYAYK        536
```

```
SEQ ID NO: 35          moltype = DNA  length = 1518
FEATURE                Location/Qualifiers
source                 1..1518
                       mol_type = other DNA
                       organism = Amaranthus tuberculatus
SEQUENCE: 35
atgggcaaca tttctgagcg ggatgaaccc acttctgcta aaagggttgc tgttgttggt  60
gctggagtta gtggacttgc tgctgcatat aagctaaaat cccatggttt gaatgtgaca  120
ttgtttgaag ctgattctag agctggaggc aaacttaaaa ctgttaaaaa agatggtttt  180
```

-continued

```
atttgggatg agggggcaaa tactatgaca gaaagtgagg cagaagtctc gagtttgatc  240
gatgatcttg ggcttcgtga gaagcaacag ttgccaattt cacaaaataa aagatacata  300
gctagagatg gtcttcctgt gctactacct tcaaatcccg ctgcactgct cacgagcaat  360
atcctttcag caaaatcaaa gctgcaaatt atgttggaac cattttttctg gagaaaacac  420
aatgctactg agctttctga tgagcatgtt caggaaagcg ttggtgaatt ttttgagcga  480
cattttggga aagagtttgt tgattatgtt attgaccctt ttgttgcggg tacatgtggt  540
ggagatcctc aatcgctttc tatgcaccat acatttccag aagtatggaa tattgaaaaa  600
aggtttggct ctgtgtttgc tggactaatt caatcaacat tgttatctaa gaaggaaaag  660
ggtggaggag gaaatgcttc tatcaagaag cctcgtgtac gtggttcatt ttcattccat  720
ggtggaatgc agacacttgt tgacacaata tgcaaacagc ttggtgaaga tgaactcaaa  780
ctccagtgtg aggtgctgtc cttgtcatac aaccagaagg ggatcccttc attagggaat  840
tggtcagtct cttctatgtc aaataatacc agtgaagatc aatcttatga tgctgtggtt  900
gtcactgctc caattcgcaa tgtcaaagaa atgaagatta tgaaattcgg aaatccattt  960
tcacttgact ttattccaga ggtgagttac gtacccctct ctgttatgat tactgcattc  1020
aagaaggata aagtgaagag accactcgag ggctttggag ttcttatccc ctctaaagag  1080
caacataatg gactgaagac tcttggtact ttattttcct ccatgatgtt tcccgatcgt  1140
gctccatctg acatgtgtct ctttactaca tttgtcggag gaagcagaaa tagaaaactt  1200
gcaaacgctt caacggatga attgaagcaa atagtttctt ctgaccttca gcagctgttg  1260
ggcactgagg acgaaccttc atttgtcaat catctctttt ggagcaacgc attcccgttg  1320
tatggacaca attacgattc tgttttgaga gccatagaca agatggaaaa ggatcttcct  1380
ggattttttt atgcaggtaa ccataagggt ggactttcag tgggaaaagc gatggcctcc  1440
ggatgcaagg ctgcggaact tgtaatatcc tatctggact ctcatatata tgtgaagatg  1500
gatgagaaga ccgcgtaa                                                 1518

SEQ ID NO: 36          moltype = AA  length = 505
FEATURE                Location/Qualifiers
source                 1..505
                       mol_type = protein
                       organism = Amaranthus sp.
SEQUENCE: 36
MGNISERDEP TSAKRVAVVG AGVSGLAAAY KLKSHGLNVT LFEADSRAGG KLKTVKKDGF  60
IWDEGANTMT ESEAEVSSLI DDLGLREKQQ LPISQNKRYI ARDGLPVLLP SNPAALLTSN  120
ILSAKSKLQI MLEPFFWRKH NATELSDEHV QESVGEFFER HFGKEFVDYV IDPFVAGTCG  180
GDPQSLSMHH TFPEVWNIEK RFGSVFAGLI QSTLLSKKEK GGGGNASIKK PRVRGSFSFH  240
GGMQTLVDTI CKQLGEDELK LQCEVLSLSY NQKGIPSLGN WSVSSMSNNT SEDQSYDAVV  300
VTAPIRNVKE MKIMKFGNPF SLDFIPEVSY VPLSVMITAF KKDKVKRPLE GFGVLIPSKE  360
QHNGLKTLGT LFSSMMFPDR APSDMCLFTT FVGGSRNRKL ANASTDELKQ IVSSDLQQLL  420
GTEDEPSFVN HLFWSNAFPL YGHNYDSVLR AIDKMEKDLP GFFYAGNHKG GLSVGKAMAS  480
GCKAAELVIS YLDSHIYVKM DEKTA                                         505

SEQ ID NO: 37          moltype = DNA  length = 1521
FEATURE                Location/Qualifiers
source                 1..1521
                       mol_type = other DNA
                       organism = Arabidopsis thaliana
SEQUENCE: 37
atggagttat ctcttctccg tccgacgact caatcgcttc ttccgtcgtt ttcgaagccc  60
aatctccgat taaatgttta taagcctctt agactccgtt gttcagtggc cggtggacca  120
accgtcggat cttcaaaaat cgaaggcgga ggaggcacca ccatcacgac ggattgtgtg  180
attgtcggcg gaggtattag tggtctttgc atcgctcagg cgcttgctac taagcatcct  240
gatgctgctc cgaatttaat tgtgaccgag gctaaggatc gtgttggagg caacattatc  300
actcgtgaag agaatggttt tctctgggaa gaaggtccca atagttttca accgtctgat  360
cctatgctca ctatggtggt agatagtggt ttgaaggatg atttggtgtt gggagatcct  420
actgcgccaa ggtttgtgtt gtggaatggg aaattgaggc cggttccatc gaagctaaca  480
gacttaccgt tctttgattt gatgagtatt ggtgggaaga ttagagctgg ttttggtgca  540
cttggcattc gaccgtcacc tccaggtcgt gaagaatctg tggaggagtt tgtacggcgt  600
aacctcggtg atgaggtttt tgagcgcctg attgaaccgt tttgttcagg tgtttatgct  660
ggtgatcctt caaaactgag catgaaagca gcgtttggga aggtttggaa actagagcaa  720
aatggtggaa gcataatagg tggtactttt aaggcaattc aggagaggaa aaacgctccc  780
aaggcagaac gagacccgcg cctgccaaaa ccacagggcc aaacagttgg ttctttcagg  840
aagggacttc gaatgttgcc agaagcaata tctgcaagat taggtagcaa agttaagttg  900
tcttggaagc tctcaggtat cactaagctg gagagcggag gatacaactt aacatatgag  960
actccagatg gtttagtttc cgtgcagagc aaaagtgttg taatgacggt gccatctcat  1020
gttgcaagtg gtctcttgcg ccctctttct gaatctgctg caaatgcact ctcaaaacta  1080
tattacccac cagttgcagc agtatctatc tcgtacccga aagaagcaat ccgaacagaa  1140
tgtttgatag atggtgaact aaagggtttt gggcaattgc atccacgcac gcaaggagtt  1200
gaaacattag gaactatcta cagctcctca ctctttccaa atcgcgcacc gcccggaaga  1260
attttgctgt tgaactacat tggcgggtct acaaacaccg gaattctgtc caagtctgaa  1320
ggtgagttag tggaagcatt tctagttggt cactttgata tccttgacac ggctaaatca  1380
tctctaacgt cttcgggcta cgaagggcta tttttgggtg gcaattacgt cgctggtgta  1440
gccttaggcc ggtgtgtaga aggcgcatat gaaaccgcga ttgaggtcaa caacttcatg  1500
tcacggtacg cttacaagta a                                             1521

SEQ ID NO: 38          moltype = AA  length = 506
FEATURE                Location/Qualifiers
source                 1..506
                       mol_type = protein
                       organism = Arabidopsis sp.
SEQUENCE: 38
```

-continued

```
MELSLLRPTT QSLLPSFSKP NLRLNVYKPL RLRCSVAGGP TVGSSKIEGG GGTTITTDCV  60
IVGGGISGLC IAQALATKHP DAAPNLIVTE AKDRVGGNII TREENGFLWE EGPNSFQPSD  120
PMLTMVVDSG LKDDLVLGDP TAPRFVLWNG KLRPVPSKLT DLPFFDLMSI GGKIRAGFGA  180
LGIRPSPPGR EESVEEFVRR NLGDEVFERL IEPFCSGVYA GDPSKLSMKA AFGKVWKLEQ  240
NGGSIIGGTF KAIQERKNAP KAERDPRLPK PQGQTVGSFR KGLRMLPEAI SARLGSKVKL  300
SWKLSGITKL ESGGYNLTYE TPDGLVSVQS KSVVMTVPSH VASGLLRPLS ESAANALSKL  360
YYPPVAAVSI SYPKEAIRTE CLIDGELKGF GQLHPRTQGV ETLGTIYSSS LFPNRAPPGR  420
ILLLNYIGGS TNTGILSKSE GELVEAFLVG HFDILDTAKS SLTSSGYEGL FLGGNYVAGV  480
ALGRCVEGAY ETAIEVNNFM SRYAYK                                      506

SEQ ID NO: 39          moltype = DNA  length = 1515
FEATURE                Location/Qualifiers
source                 1..1515
                       mol_type = other DNA
                       organism = Nicotiana tabacum
SEQUENCE: 39
atggctcctt ctgccggaga agataaacac agttctgcga agagagtcgc agtcattggt  60
gcaggcgtca gtgggcttgc tgcagcatac aagttgaaaa tccatggctt gaatgtgaca  120
gtatttgaag cagaagggaa agctggaggg aagttacgta gcgtgagcca agatggcctg  180
atatgggatg aaggggcaaa tactatgact gaaagtgaag gtgatgttac atttttgatt  240
gattctcttg gactccgaga aaagcaacaa tttccacttt cacaaaacaa gcgctacatt  300
gccagaaatg gtactcctgt actgttacct tcaaatccaa ttgatctgat caaaagcaat  360
tttctttcca ctggatcaaa gcttcagatg cttctggaac caatattatg gaagaataaa  420
aagctctccc aggtgtctga ctcacatgaa agtgtcagtg gattcttcca gcgtcatttt  480
ggaaaggagg ttgttgacta tctaattgac ccttttgttg ctggaacgtg tggtggtgat  540
cctgactcgc tttcaatgca ccattcattt ccagagttgt ggaatttaga gaaaaggttt  600
ggctcagtca tacttggagc tattcgatct aagttatccc ctaaaaatga aaagaagcaa  660
gggccaccca aaacttcagc aaataagaag cgccagcggg gatctttttc ctttttgggc  720
ggaatgcaaa cacttactga tgcaatatgc aaagatctca gagaagatga acttagacta  780
aactctagag ttctggaatt atcttgtagc tgtactgagg actctgcgat agatagctgg  840
tcaattattt ctgcctctcc acacaaaagg caatcagaag aagaatcatt tgatgctgta  900
attatgacgg ccccactctg tgatgttaag agtatgaaga ttgctaagag aggaaatcca  960
tttctactca actttattcc tgaggttgat tatgtaccgc tatctgttgt tataaccaca  1020
tttaagaggg aaaacgtaaa gtatcccctt gagggttttg ggttcttgt accttccaag  1080
gagcaacaac atggtctcaa gacactaggc accctcttct cttctatgat gtttccagat  1140
cgggcaccaa acaatgttta tctctatact acttttgttg gtggaagccg aaatagagaa  1200
cttgcaaaag cctcaaggac tgagctgaaa gagatagtaa cttctgacct taagcagctg  1260
ttgggtgctg agggagagcc aacatatgtg aatcatctat actggagtaa agcatttcca  1320
ttgtacgggc ataactatga ttcagtccta gatgcaattg acaaaatgga gaaaaatctt  1380
cctggattat tctatgcagg taaccacagg gggggattgt cagttggcaa agcattatct  1440
tctggatgca atgcagctga tcttgttata tcatatcttg aatccgtctc aactgactcc  1500
aaaagacatt gctga                                                  1515

SEQ ID NO: 40          moltype = AA  length = 504
FEATURE                Location/Qualifiers
source                 1..504
                       mol_type = protein
                       organism = Nicotiana sp.
SEQUENCE: 40
MAPSAGEDKH SSAKRVAVIG AGVSGLAAAY KLKIHGLNVT VFEAEGKAGG KLRSVSQDGL  60
IWDEGANTMT ESEGDVTFLI DSLGLREKQQ FPLSQNKRYI ARNGTPVLLP SNPIDLIKSN  120
FLSTGSKLQM LLEPILWKNK KLSQVSDSHE SVSGFFQRHF GKEVVDYLID PFVAGTCGGD  180
PDSLSMHHSF PELWNLEKRF GSVILGAIRS KLSPKNEKKQ GPPKTSANKK RQRGSFSFLG  240
GMQTLTDAIC KDLREDELRL NSRVLELSCS CTEDSAIDSW SIISASPHKR QSEEESFDAV  300
IMTAPLCDVK SMKIAKRGNP FLLNFIPEVD YVPLSVVITT FKRENVKYPL EGFGVLVPSK  360
EQQHGLKTLG TLFSSMMFPD RAPNNVYLYT TFVGGSRNRE LAKASRTELK EIVTSDLKQL  420
LGAEGEPTYV NHLYWSKAFP LYGHNYDSVL DAIDKMEKNL PGLFYAGNHR GGLSVGKALS  480
SGCNAADLVI SYLESVSTDS KRHC                                        504

SEQ ID NO: 41          moltype = DNA  length = 1509
FEATURE                Location/Qualifiers
source                 1..1509
                       mol_type = other DNA
                       organism = Glycine max
SEQUENCE: 41
atggcttcct ctgcaacaga cgataaccca agatctgtaa aaagagtagc tgttgttggt  60
gctggggtaa gtgggcttgc tgcggcttac aaattgaaat cacatggtct ggatgtcact  120
gtatttgaag ctgagggaag agctggaggg aggttgagaa gtgtttctca ggatggtcta  180
atttgggatg agggagctaa tacaatgact gaaagtgaaa ttgaggttaa aggtttgatt  240
gatgctcttg gacttcaaga aaagcagcag tttccaatat cacagcataa gcgctatatt  300
gtgaaaaatg gggcaccact tctggtaccc acaaatcctg ctgcactact gaagagtaaa  360
ctgctttctg cacaatcaaa gatccatctc atttttgaac catttatgtg gaaaagaagt  420
gacccctcta atgtgtgtga tgaaaattct gtggaaagtg taggcaggtt ctttgaacgt  480
cattttggaa aagaggttgt ggactatctg attgatcctt ttgttggggg cactagtgca  540
gcagatcctg aatctctctc tatgcgccat tctttcccag agctatggaa tttggagaaa  600
aggtttggct ccattatagc cggggcattg caatctaagt tattcgccaa aagggaaaaa  660
actggagaaa ataggactgc actaagaaaa aacaaacaca agcgtggttc gttttctttc  720
cagggtggga tgcagacact gacagataca ttgtgcaaag agcttggcaa agacgacctt  780
aaattaaatg aaaaggtttt gacattagct tatggtcatg atggaagttc ctcttcacaa  840
```

```
aactggtcta ttactagtgc ttctaaccaa agtacacaag atgttgatgc agtaatcatg  900
acggctcctc tatataatgt caaggacatc aagatcacaa aaaggggaac tccctttcca  960
cttaattttc ttcccgaggt aagctacgtg ccaatctcag tcatgattac taccttcaaa  1020
aaggagaatg taaagagacc tttggaggga tttggagttc ttgttccttc taaagagcaa  1080
aaaaatggtt taaaaaccct tggtacactt ttttcctcta tgatgttccc agatcgtgca  1140
cctagtgatt tatatctcta taccaccttc attggcggaa ctcaaaacag ggaacttgct  1200
caagcttcaa ctgacgagct taggaaaatt gttacttctg acctgagaaa gttgttggga  1260
gcagaggggg aaccaacatt tgttaaccat ttctattgga gtaaaggctt tcctttgtat  1320
ggacgtaact atgggtcagt tcttcaagca attgataaga tagaaaaaga tcttcccgga  1380
tttttctttg caggtaacta caaaggtgga ctctcagttg gcaaagcaat agcctcaggc  1440
tgcaaagcag ctgatcttgt gatatcctac ctcaactctg cttcagacaa cacagtgcct  1500
gataaatga                                                         1509

SEQ ID NO: 42          moltype = AA  length = 502
FEATURE                Location/Qualifiers
source                 1..502
                       mol_type = protein
                       organism = Glycine sp.
SEQUENCE: 42
MASSATDDNP RSVKRVAVVG AGVSGLAAAY KLKSHGLDVT VFEAEGRAGG RLRSVSQDGL  60
IWDEGANTMT ESEIEVKGLI DALGLQEKQQ FPISQHKRYI VKNGAPLLVP TNPAALLKSK  120
LLSAQSKIHL IFEPFMWKRS DPSNVCDENS VESVGRFFER HFGKEVVDYL IDPFVGGTSA  180
ADPESLSMRH SFPELWNLEK RFGSIIAGAL QSKLFAKREK TGENRTALRK NKHKRGSFSF  240
QGGMQTLTDT LCKELGKDDL KLNEKVLTLA YGHDGSSSSQ NWSITSASNQ STQDVDAVIM  300
TAPLYNVKDI KITKRGTPFP LNFLPEVSYV PISVMITTFK KENVKRPLEG FGVLVPSKEQ  360
KNGLKTLGTL FSSMMFPDRA PSDLYLYTTF IGGTQNRELA QASTDELRKI VTSDLRKLLG  420
AEGEPTFVNH FYWSKGFPLY GRNYGSVLQA IDKIEKDLPG FFFAGNYKGG LSVGKAIASG  480
CKAADLVISY LNSASDNTVP DK                                          502

SEQ ID NO: 43          moltype = DNA  length = 1205
FEATURE                Location/Qualifiers
source                 1..1205
                       mol_type = other DNA
                       organism = Cucumis sativus
SEQUENCE: 43
agcttccaac cttccgatcc tattctcacc atggtggtgg atagtggctt aaaagatgat  60
ttagttctgg gagacccaga tgcacctcga tttgtattgt ggaatggaaa gctcagacca  120
gtgcctgcga aacctaatga tctacctttc tttgacctga tgagcattgg tggaaaaatc  180
agagcaggct ttggtgccct gggcattcgc cctcctcctc caggtcgaga ggaatcagtt  240
gaagaatttg tccgtcggaa ccttggcaat gaagtttttg aacgtttgat agagccattt  300
tgttctggtg tatacgctgg tgacccttca aagctaagca tgaaagcagc ttttggtaag  360
gtttggaggc tagagcaaaa tggtggtagt attattggtg ggactttcaa agcacttcaa  420
gaaaggaata aaactaccaa accaccaaga gatccgcgtc taccaaagcc taagggccaa  480
actgttggat cttttcggaa aggacttacc atgttgccaa atgctatttc tacttgtttg  540
gggagtaaag taaaagtatc ttggaagcta tctagtatca gtaaagtgga tgacggaggt  600
tatagtttga catacgaaac accagaagga ctagtctcca tactaagcag aagtgtcatc  660
atgacggttc cttcttatat tgctggcact ctgttgcgtc caatctcggg gaaagctgca  720
gatgcacttt caaaatttta ttatccacca gttgcatcag tgaccatatc atatccaaaa  780
ggagcaatta ggaaagaatg cttgattgat ggtgaactaa aggggtttgg tcaattgcac  840
cctcgtagcc agggggtgac tactttggga actatataca gctcatcact tttcctaat  900
cgagcgccag atggaagggt attgctcttg aactacattg gaggggctac taatactgga  960
attctttctc agacagagag cgagctcata gaagtagttg atcgggattt aagaaaaatc  1020
ctcataaacc caaacgcaga ggatcctcta ccattgagcg tgagggtgtg gccacaagcc  1080
attccacagt tcttgattgg ccatctcgat gttctagaca ccgccaaggc cggactgaga  1140
gaggctggaa tggaggggct atttttaggt ggaaactatg tatgcggtgt ggccttgggg  1200
agatg                                                             1205

SEQ ID NO: 44          moltype = AA  length = 401
FEATURE                Location/Qualifiers
source                 1..401
                       mol_type = protein
                       organism = Cucumis sp.
SEQUENCE: 44
SFQPSDPILT MVVDSGLKDD LVLGDPDAPR FVLWNGKLRP VPAKPNDLPF FDLMSIGGKI  60
RAGFGALGIR PPPPGREESV EEFVRRNLGN EVFERLIEPF CSGVYAGDPS KLSMKAAFGK  120
VWRLEQNGGS IIGGTFKALQ ERNKTTKPPR DPRLPKPKGQ TVGSFRKGLT MLPNAISTCL  180
GSKVKVSWKL SSISKVDDGG YSLTYETPEG LVSILSRSVI MTVPSYIAGT LLRPISGKAA  240
DALSKFYYPP VASVTISYPK GAIRKECLID GELKGFGQLH PRSQGVTTLG TIYSSSLFPN  300
RAPDGRVLLL NYIGGATNTG ILSQTESELI EVVDRDLRKI LINPNAEDPL PLSVRVWPQA  360
IPQFLIGHLD VLDTAKAGLR EAGMEGLFLG GNYVCGVALG R                     401

SEQ ID NO: 45          moltype = DNA  length = 1521
FEATURE                Location/Qualifiers
source                 1..1521
                       mol_type = other DNA
                       organism = Oryza sativa
SEQUENCE: 45
atggccgcct ccgacgaccc ccgcggcggg aggtccgtcg ccgtcgtcgg cgccggcgtc  60
agtgggctcg cggcggcgta caggctgagg aagcgcggcg tgcaggtgac ggtgttcgag  120
```

-continued

```
gcggccgaca gggcgggtgg gaagatacgg accaactccg agggcgggtt catctgggac  180
gaaggggcca acaccatgac agagagtgaa ttggaggcaa gcaggcttat tgacgatctt  240
ggcctacaag gcaaacagca gtatcctaac tcacaacaca agcgttacat tgtcaaagat  300
ggagcaccaa cactgattcc ctcagatccc attgcgctca tgaaaagcac tgttctttct  360
acaaaatcaa agctcaagct atttctggaa ccatttctct atgagaaatc tagcagaagg  420
acctcgggaa aagtgtctga tgaacattta agtgagagtg tgatttttct gtgtatatgt  480
agagataatc aggttgttga ttatcttatt gatccatttg tggctggaac aagcggagga  540
gatcctgagt cattatcaat tcgtcatgca tttccagcat tatggaattt ggagaataag  600
tatggctctg tcattgctgg tgccatcttg tccaaactat ccactaaggg tgattcagtg  660
aagacaggag gtgcttcgcc agggaaagga aggaataaac gtgtgtcatt ttcatttcat  720
ggtggaatgc agtcactaat agatgcactt cacaatgaag ttggagatgg taacgtgaag  780
cttggtacag aagtgttgtc attggcatgt tgctgtgatg gagtctcttc ttctggtggt  840
tggtcaattt ctgttgattc aaaagatgct aaagggaaag atctcagaaa gaaccaatct  900
ttcgatgctg ttataatgac tgctccattg tctaatgtcc agaggatgaa gtttacaaaa  960
ggtggagttc cctttgtgct agactttctt cctaaggtcg attatctacc actatctctc  1020
atggtaacag cttttaagaa ggaagatgtc aaaaaaccat tggaaggatt tggtgccttg  1080
ataccctata aggaacagca aaagcatggt ctcaaaaccc ttgggaccct cttctcctcg  1140
atgatgtttc cagatcgagc tcctaatgat caatatctat atacatcttt cattgggggg  1200
agccataata gagacctcgc tggggctcca acggctattc tgaaacaact tgtgacctct  1260
gacctaagaa agctcttggg tgttgaggga caacctactt ttgtgaagca tgtacattgg  1320
agaaatgctt ttcctttata tggccagaat tatgatctgg tactggaagc tatagcaaaa  1380
atggagaaca atcttccagg gttcttttac gcaggaaata acaaggatgg gttggctgtt  1440
ggaaatgtta tagcttcagg aagcaaggct gctgaccttg tgatctctta tcttgaatct  1500
tgcacagatc aggacaatta g                                            1521

SEQ ID NO: 46          moltype = AA  length = 506
FEATURE                Location/Qualifiers
source                 1..506
                       mol_type = protein
                       organism = Oryza sativa
SEQUENCE: 46
MAASDDPRGG RSVAVVGAGV SGLAAAYRLR KRGVQVTVFE AADRAGGKIR TNSEGGFIWD  60
EGANTMTESE LEASRLIDDL GLQGKQQYPN SQHKRYIVKD GAPTLIPSDP IALMKSTVLS  120
TKSKLKLFLE PFLYEKSSRR TSGKVSDEHL SESVIFLCIC RDNQVVDYLI DPFVAGTSGG  180
DPESLSIRHA FPALWNLENK YGSVIAGAIL SKLSTKGDSV KTGGASPGKG RNKRVSFSFH  240
GGMQSLIDAL HNEVGDGNVK LGTEVLSLAC CCDGVSSSGG WSISVDSKDA KGKDLRKNQS  300
FDAVIMTAPL SNVQRMKFTK GGVPFVLDFL PKVDYLPLSL MVTAFKKEDV KKPLEGFGAL  360
IPYKEQQKHG LKTLGTLFSS MMFPDRAPND QYLYTSFIGG SHNRDLAGAP TAILKQLVTS  420
DLRKLLGVEG QPTFVKHVHW RNAFPLYGQN YDLVLEAIAK MENNLPGFFY AGNNKDGLAV  480
GNVIASGSKA ADLVISYLES CTDQDN                                      506

SEQ ID NO: 47          moltype = DNA  length = 26
FEATURE                Location/Qualifiers
misc_feature           1..26
                       note = Forward primer; Cr_PPO1_Fw
source                 1..26
                       mol_type = other DNA
                       organism = synthetic construct
SEQUENCE: 47
atgatgttga cccagactcc tgggac                                       26

SEQ ID NO: 48          moltype = DNA  length = 25
FEATURE                Location/Qualifiers
misc_feature           1..25
                       note = Reverse primer; Cr_PPO1_Rv
source                 1..25
                       mol_type = other DNA
                       organism = synthetic construct
SEQUENCE: 48
ttaggccttg actgcggcct tggac                                        25
```

PLANTS HAVING INCREASED TOLERANCE TO HERBICIDES

CROSS-REFERENCE TO RELATED APPLICATIONS

This application is a continuation of U.S. patent application Ser. No. 16/035,115, filed Jul. 13, 2018, which is a continuation of U.S. patent application Ser. No. 13/918,212, filed Jun. 14, 2013, which claims the benefit of U.S. Provisional Application No. 61/661,364, filed Jun. 19, 2012. The entire contents of the aforementioned applications are incorporated herein by reference.

REFERENCE TO SEQUENCE LISTING SUBMITTED ELECTRONICALLY

This application was filed electronically via Patent Center and includes an electronically submitted sequence listing in .xml format. The .xml file contains a sequence listing entitled "73943CON1A_Seqlisting.XML" created on Nov. 30, 2022, and is 90,885 bytes in size. The sequence listing contained in this .xml file is part of the specification and is hereby incorporated by reference herein in its entirety.

FIELD OF THE INVENTION

The present invention relates in general to methods for conferring on plants agricultural level tolerance to a herbicide. Particularly, the invention refers to plants having an increased tolerance to "benzoxazinone-derivative" herbicides. More specifically, the present invention relates to methods and plants obtained by mutagenesis and cross-breeding and transformation that have an increased tolerance to "benzoxazinone-derivative" herbicides.

BACKGROUND OF THE INVENTION

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis which is the oxidation of protoporphyrinogen IX to protoporphyrin IX. (Matringe et al. 1989. Biochem. 1. 260: 231). PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (+−)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobenzoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs.

Many of these compounds competitively inhibit the normal reaction catalyzed by the enzyme, apparently acting as substrate analogs.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39: 1155; Dailey et al. 1994. J. Biol. Chem. 269: 813) are resistant to these herbicidal inhibitors. Mutants of the unicellular alga *Chlamydomonas reinhardtii* resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer:Netherlands. pp. 567-70). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPOs.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to PPO inhibitors (see e.g. U.S. Pat. No. 5,767,373 or U.S. Pat. No. 5,939,602, and patent family members thereof). In addition, US 2010/0100988 and WO 2007/024739 discloses nucleotide sequences encoding amino acid sequences having enzymatic activity such that the amino acid sequences are resistant to PPO inhibitor herbicidal chemicals, in particular 3-phenyluracil inhibitor specific PPO mutants.

To date, the prior art has not described benzoxazinone-derivative herbicide tolerant plants containing at least one wild-type or mutated PPO nucleic acid. Nor has the prior art described benzoxazinone-derivative herbicide tolerant crop plants containing mutations on genomes other than the genome from which the PPO gene is derived. Therefore, what is needed in the art is the identification of benzoxazinone-derivative herbicide tolerance genes from additional genomes and species. What are also needed in the art are crop plants and crop plants having increased tolerance to herbicides such as benzoxazinone-derivative herbicide and containing at least one wildtype and/or mutated PPO nucleic acid. Also needed are methods for controlling weed growth in the vicinity of such crop plants or crop plants. These compositions and methods would allow for the use of spray over techniques when applying herbicides to areas containing crop plants or crop plants.

SUMMARY OF THE INVENTION

The problem is solved by the present invention which refers to a method for controlling undesired vegetation at a plant cultivation site, the method comprising the steps of:

a) providing, at said site, a plant that comprises at least one nucleic acid comprising a nucleotide sequence encoding a wild type protoporphyrinogen oxidase (PPO) or a mutated protoporphyrinogen oxidase (mut-PPO) which is resistant or tolerant to a benzoxazinone-derivative herbicide, b) applying to said site an effective amount of said herbicide.

In addition, the present invention refers to a method for identifying a benzoxazinone-derivative herbicide by using a wild-type or mut-PPO encoded by a nucleic acid which comprises the nucleotide sequence of SEQ ID NO: 1, 3, 5, 7, 9, 11, 13, 15, 17, 19, 21, 23, 25, 27, 29, 31, 33, 35, 37, 39, 41, 43, or 45, or a variant thereof.

Said method comprises the steps of:

a) generating a transgenic cell or plant comprising a nucleic acid encoding a mut-PPO, wherein the mut-PPO is expressed;

b) applying a benzoxazinone-derivative herbicide to the transgenic cell or plant of a) and to a control cell or plant of the same variety;

c) determining the growth or the viability of the transgenic cell or plant and the control cell or plant after application of said test compound, and d) selecting test compounds which confer reduced growth to the control cell or plant as compared to the growth of the transgenic cell or plant.

Another object refers to a method of identifying a nucleotide sequence encoding a mut-PPO which is resistant or tolerant to a benzoxazinone-derivative herbicide, the method comprising:

a) generating a library of mut-PPO-encoding nucleic acids, b) screening a population of the resulting mut-PPO-encoding nucleic acids by expressing each of said nucleic acids in a cell or plant and treating said cell or plant with a benzoxazinone-derivative herbicide, c) comparing the benzoxazinone-derivative herbicide-tolerance levels provided by said population of mut-PPO encoding nucleic acids with the benzoxazinone-derivative herbicide-tolerance level provided by a control PPO-encoding nucleic acid, d) selecting at least one mut-PPO-encoding nucleic acid that provides a significantly increased level of tolerance to a benzoxazinone-derivative herbicide as compared to that provided by the control PPO-encoding nucleic acid.

In a preferred embodiment, the mut-PPO-encoding nucleic acid selected in step d) provides at least 2-fold as much tolerance to a benzoxazinone-derivative herbicide as compared to that provided by the control PPO-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mut-PPO which is resistant or tolerant to a benzoxazinone-derivative herbicide, the method comprising:

a) identifying an effective amount of a benzoxazinone-derivative herbicide in a culture of plant cells or green algae.

b) treating said plant cells or green algae with a mutagenizing agent, c) contacting said mutagenized cells population with an effective amount of benzoxazinone-derivative herbicide, identified in a), d) selecting at least one cell surviving these test conditions, e) PCR-amplification and sequencing of PPO genes from cells selected in d) and comparing such sequences to wild-type PPO gene sequences, respectively.

In a preferred embodiment, the mutagenizing agent is ethylmethanesulfonate.

Another object refers to an isolated nucleic acid encoding a mut-PPO, the nucleic acid comprising the sequence of SEQ ID NO: 1, 3, 5, 7, 9, 11, 13, 15, 17, 19, 21, 23, 25, 27, 29, 31, 33, 35, 37, 39, 41, 43, or 45, or a variant thereof, as defined hereinafter.

Another object refers to an isolated mut-PPO polypeptide, the polypeptide comprising the sequence set forth in SEQ ID NO: 2, 4, 6, 8, 10, 12, 14, 16, 18, 20, 22, 24, 26, 28, 30, 32, 34, 36, 38, 40, 42, 44, or 46, a variant, derivative, orthologue, paralogue or homologue thereof, as defined hereinafter.

In a preferred embodiment, the nucleic acid being identifiable by a method as defined above.

In another embodiment, the invention refers to a plant cell transformed by a wild-type or a mut-PPO nucleic acid or a plant which has been mutated to obtain a plant expressing, preferably over-expressing a wild-type or a mut-PPO nucleic acid, wherein expression of the nucleic acid in the plant cell results in increased resistance or tolerance to a benzoxazinone-derivative herbicide as compared to a wild type variety of the plant cell.

In another embodiment, the invention refers to a plant comprising a plant cell according to the present invention, wherein expression of the nucleic acid in the plant results in the plant's increased resistance to benzoxazinone-derivative herbicide as compared to a wild type variety of the plant.

The plants of the present invention can be transgenic or non-transgenic.

Preferably, the expression of the nucleic acid of the invention in the plant results in the plant's increased resistance to benzoxazinone-derivative herbicide as compared to a wild type variety of the plant.

In another embodiment, the invention refers to a seed produced by a transgenic plant comprising a plant cell of the present invention, wherein the seed is true breeding for an increased resistance to a benzoxazinone-derivative herbicide as compared to a wild type variety of the seed.

In another embodiment, the invention refers to a method of producing a transgenic plant cell with an increased resistance to a benzoxazinone-derivative herbicide as compared to a wild type variety of the plant cell comprising, transforming the plant cell with an expression cassette comprising a wild-type or a mut-PPO nucleic acid.

In another embodiment, the invention refers to a method of producing a transgenic plant comprising, (a) transforming a plant cell with an expression cassette comprising a wildtype or a mut-PPO nucleic acid, and (b) generating a plant with an increased resistance to benzoxazinone-derivative herbicide from the plant cell.

Preferably, the expression cassette further comprises a transcription initiation regulatory region and a translation initiation regulatory region that are functional in the plant.

In another embodiment, the invention relates to using the mut-PPO of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mut-PPO polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one benzoxazinone-derivative inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mut-PPO proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

BRIEF DESCRIPTION OF THE DRAWINGS

FIG. 2A Mutagenized cells plated on solid medium without a selecting agent. FIG. 2B Mutagenized cells plated on solid medium containing $1\times10^{-7}$ M benzoxazinone-derivative I.a.35. Cells which are resistant to the benzoxazinone-derivative herbicide form colonies (circled and numbered 31 and 32), while susceptible cells do not grow. The higher number of colonies on plate A (FIG. 2A) as compared to B (FIG. 2B), indicate that the colonies on plate B are resistant to benzoxazinone-derivative I.a.35.

FIG. 3A Dose-response curve of Wild-type cells treated with benzoxazinone-derivative I.a.35 with respective $IC_{50}$. FIG. 3B Dose-response curve of mutagenized cells (strain 17) treated with benzoxazinone-derivative I.a.35 with respective $IC_{50}$. Strain 17 (FIG. 3B), resistant to the benzoxazinone-derivative 1.a.35 herbicide, shows much lower $IC_{50}$, compared to Wild-type cells.

KEY TO SEQUENCE LISTING

TABLE 1

Figure 1:
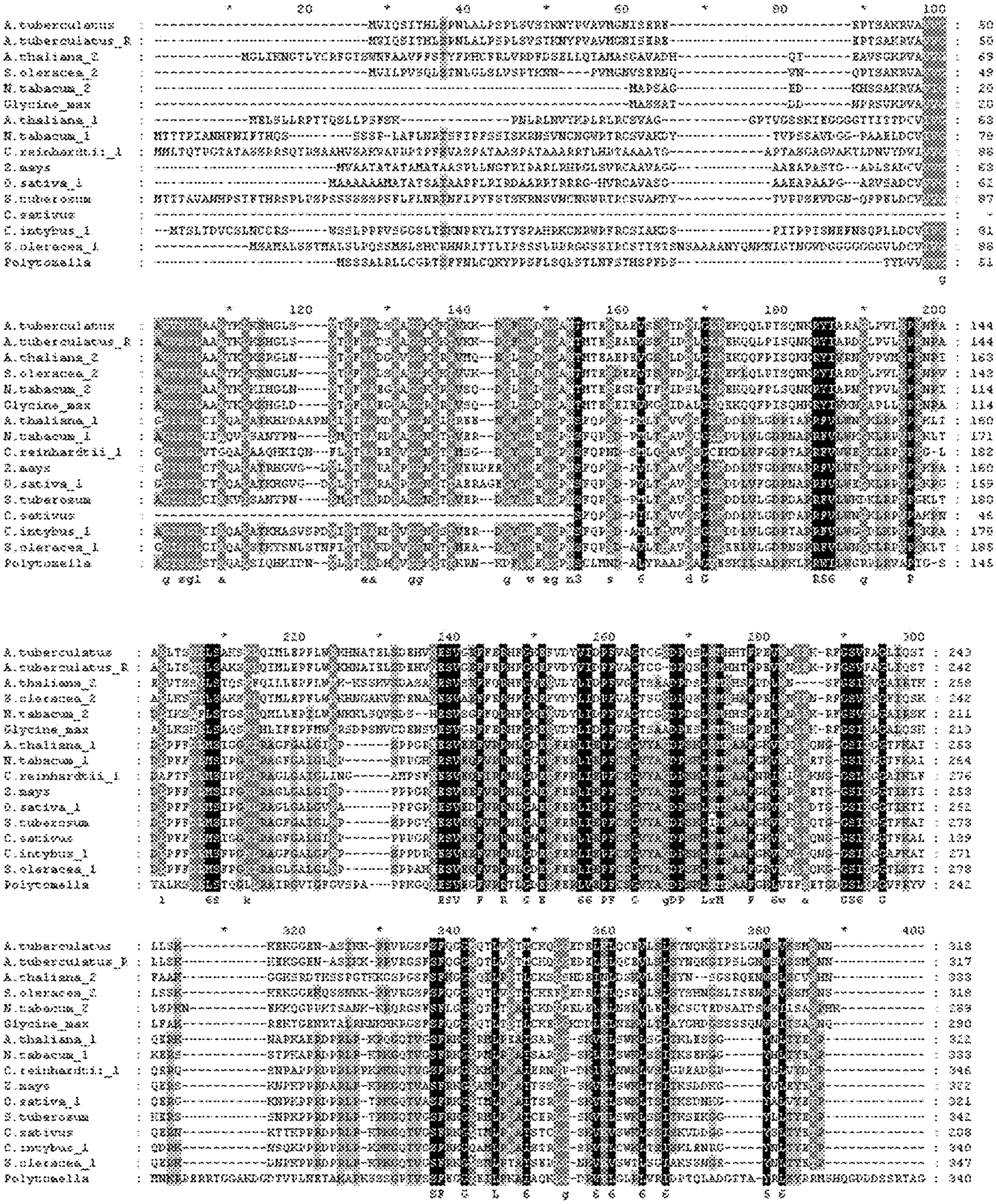
FIG. 1 shows an amino acid sequence alignment of *Amaranthus tuberculatus* (*A. tuberculatus*), *Amaranthus tuberculatus* resistant (*A. tuberculatus*_R), *Arabidopsis thaliana* long (*A. thaliana*_2), *Spinacia oleracea* short (*S. oleracea*_2), *Nicotiana tabacum* short (*N. tabacum*_2), *Glycine max* (*Glycine_max*), *Arabidopsis thaliana* short (*A. thaliana*_1), *Nicotiana tabacum* long (*N. tabacum*_1), *Chlamydomonas reinhardtii* long (*C. reinhardtii*_1), *Zea mays* (*Z. mays*), *Oryza sativa* (*O. sativa*_1), *Solanum tuberosum* (*S. tuberosum*), *Cucumis sativus* (*C. sativus*), *Cichorium intybus* (*C. intybus*_1), *Spinacia oleracea* long (*S. oleracea*_1), *Polytomella* sp. *Pringsheim* 198.80 (*Polytomella*) PPO sequences. Conserved regions are indicated in light grey, grey and black.
Figure 1:
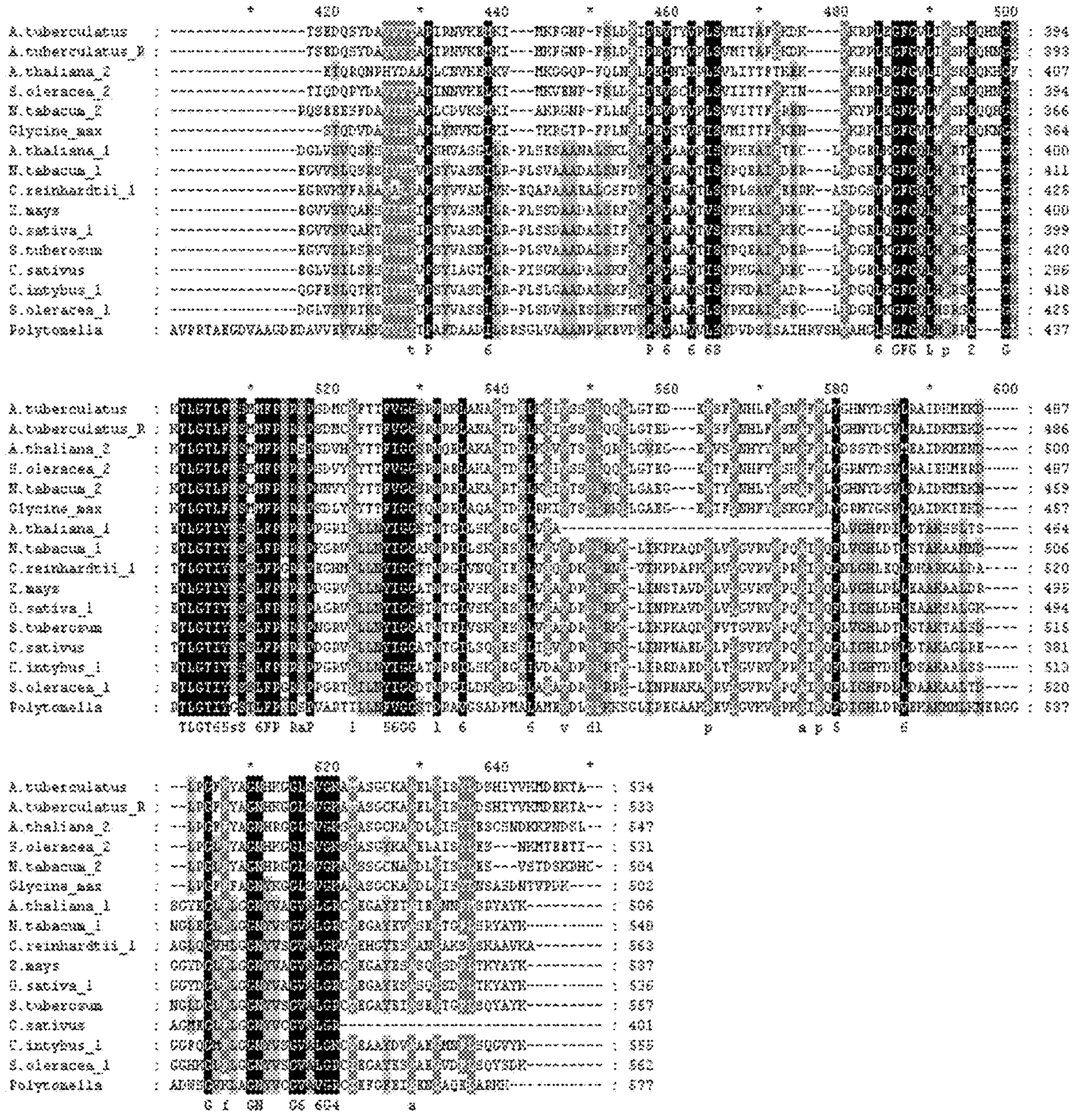
Figure 2A:
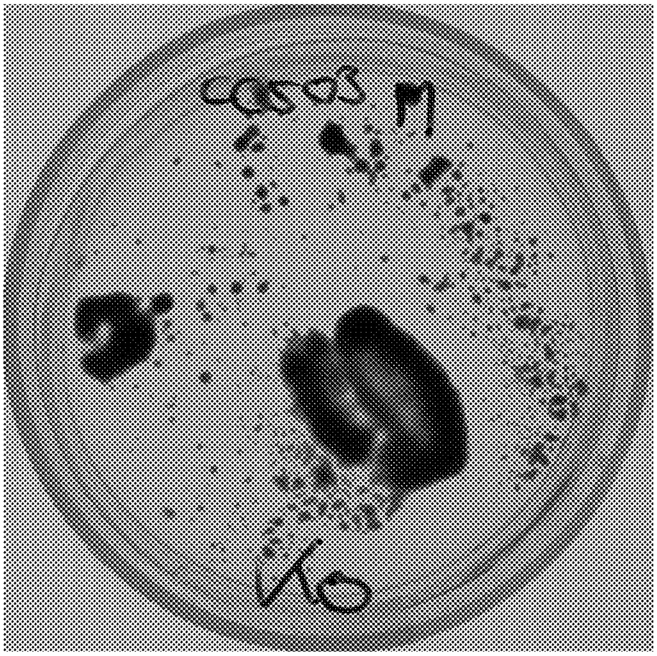
FIG. 2A and FIG. 2B show the selection of *Chlamydomonas reinhardtii* strains resistant to benzoxazinone-derivative 1.a.35 herbicide.
Figure 2B:
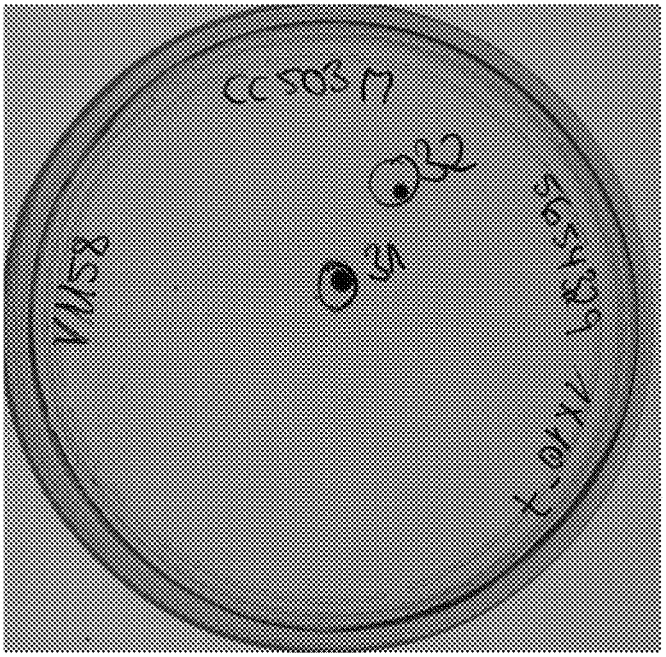
Figure 3A:
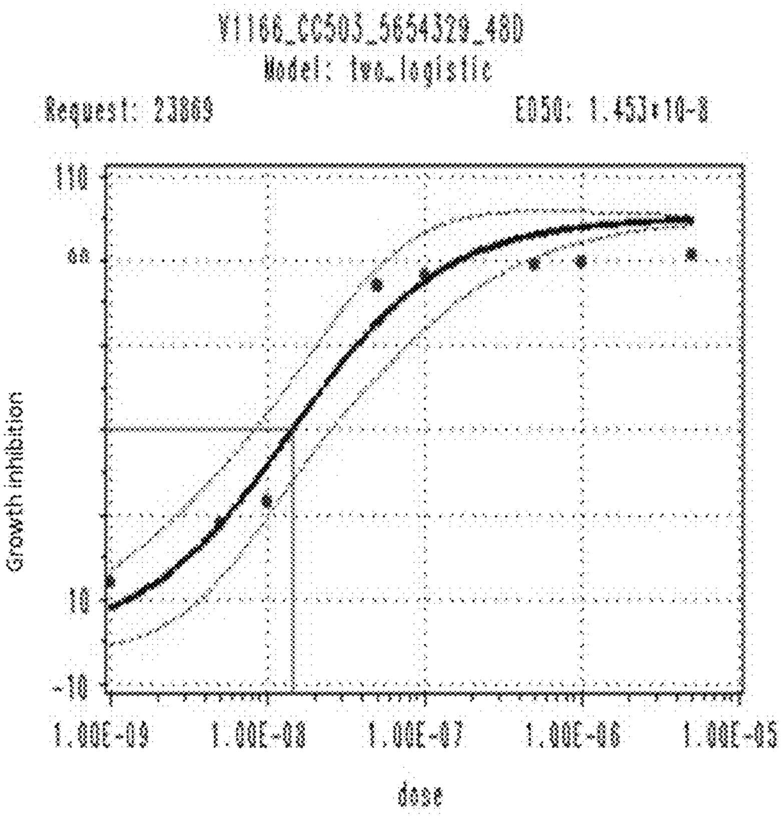
FIG. 3A and FIG. 3B show growth-characteristics of selected *Chlamydomonas reinhardtii* strains as seen in FIG. 2A and FIG. 2B, resistant to benzoxazinone-derivative 1.a.35 herbicide.
Figure 3B:
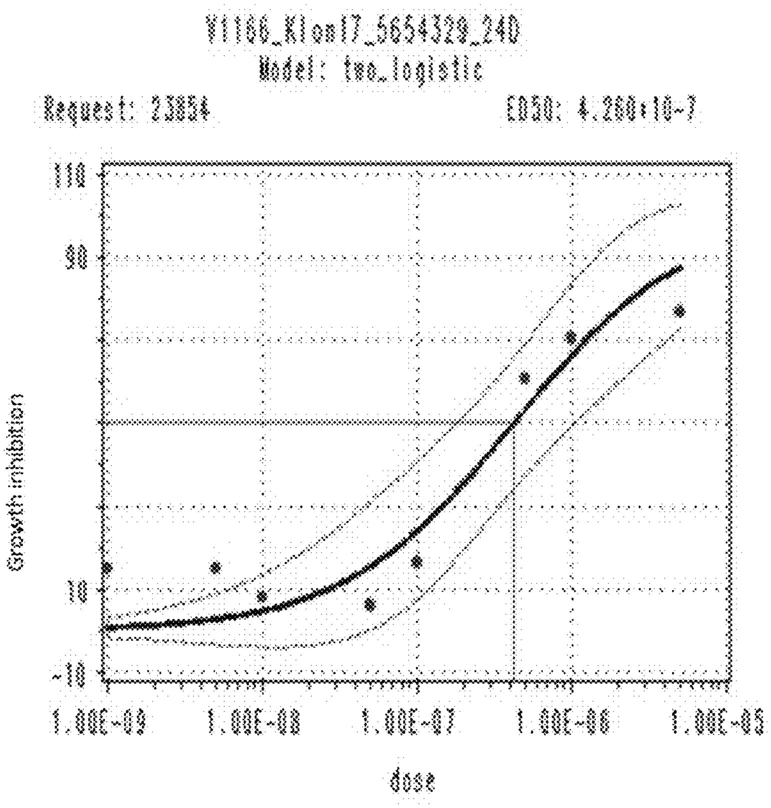

| SEQ. ID NO: | Description | Organism | Gene | Accession No: |
|---|---|---|---|---|
| 1 | PPO nucleic acid | *Amaranthus* | PPX2L_WC | DQ386114 |
| 2 | PPO amino acid | *Amaranthus* | ABD52326 | |
| 3 | PPO nucleic acid | *Amaranthus* | PPX2L_AC | DQ386117 |
| 4 | PPO amino acid | *Amaranthus* | ABD52329 | |
| 5 | PPO nucleic acid | *Amaranthus* | PPX2L_CC_R | DQ386118 |
| 6 | PPO amino acid | *Amaranthus* | ABD52330 | |
| 7 | PPO nucleic acid | *Amaranthus* | PPX2L_AC_R | DQ386116 |
| 8 | PPO amino acid | *Amaranthus* | ABD52328 | |
| 9 | PPO nucleic acid | *Arabidopsis* | PPX | AB007650 |
| 10 | PPO amino acid | *Arabidopsis* | BAB08301 | |
| 11 | PPO nucleic acid | *Nicotiana* | ppxl | AF044128 |
| 12 | PPO amino acid | *Nicotiana* | AAD02290 | |
| 13 | PPO nucleic acid | *Cichorium* | PPX1 | AF160961 |
| 14 | PPO amino acid | *Cichorium* | AF160961_1 | |
| 15 | PPO nucleic acid | *Spinacia* | SO-POX1 | AB029492 |
| 16 | PPO amino acid | *Spinacia* | BAA96808 | |
| 17 | PPO nucleic acid | *Spinacia* | SO-POX2 | AB046993 |
| 18 | PPO amino acid | *Spinacia* | BAB60710 | |
| 19 | PPO nucleic acid | *Solanum* | PPOX | AJ225107 |
| 20 | PPO amino acid | *Solanum* | CAA12400 | |
| 21 | PPO nucleic acid | *Zea* | ZM_BFc0091B03 | BT063659 |
| 22 | PPO amino acid | *Zea* | ACN28356 | |
| 23 | PPO nucleic acid | *Zea* | prpo2 | NM_001111534 |
| 24 | PPO amino acid | *Zea* | NP_001105004 | |
| 25 | PPO nucleic acid | *Chlamydomonas* | Ppx1 | AF068635 |
| 26 | PPO amino acid | *Chlamydomonas* | AAC79685 | |
| 27 | PPO nucleic acid | *Polytomella* | PPO | AF332964 |
| 28 | PPO amino acid | *Polytomella* | AF332964_1 | |
| 29 | PPO nucleic acid | *Sorghum* | Hyp. Protein | XM_002446665 |
| 30 | PPO amino acid | *Sorghum* | XP_002446710 | |

TABLE 1-continued

| SEQ. ID NO: | Description | Organism | Gene | Accession No: |
|---|---|---|---|---|
| 31 | PPO nucleic acid | *Chlorella* | | |
| 32 | PPO amino acid | *Chlorella* | | 51538 |
| 33 | PPO nucleic acid | *Oryza* | PPOX1 | AB057771 |
| 34 | PPO amino acid | *Oryza* | BAB39760 | |
| 35 | PPO nucleic acid | *Amaranthus* | PPX2 | DQ386113 |
| 36 | PPO amino acid | *Amaranthus* | ABD52325 | |
| 37 | PPO nucleic acid | *Arabidopsis* | PPOX | NM_178952 |
| 38 | PPO amino acid | *Arabidopsis* | NP_849283 | |
| 39 | PPO nucleic acid | *Nicotiana* | ppxll | AF044129 |
| 40 | PPO amino acid | *Nicotiana* | AAD02291 | |
| 41 | PPO nucleic acid | *Glycine* | hemG | AB025102 |
| 42 | PPO amino acid | *Glycine* | BAA76348 | |
| 43 | PPO nucleic acid | *Cucumis* | CsPPO | AB512426 |
| 44 | PPO amino acid | *Cucumis* | BAH84864.1 | |
| 45 | PPO nucleic acid | *Oryza* | Hyp. Protein | AL606613 |
| 46 | PPO amino acid | *Oryza* | CAE01661 | |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The present invention refers to a method for controlling undesired vegetation at a plant cultivation site, the method comprising the steps of:

a) providing, at said site, a plant that comprises at least one nucleic acid comprising a nucleotide sequence encoding a wild-type protoporphyrinogen oxidase or a mutated protoporphyrinogen oxidase (mut-PPO) which is resistant or tolerant to a benzoxazinone-derivative herbicide, b) applying to said site an effective amount of said herbicide.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising Acer spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba*

*pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

In a preferred embodiment, the plant has been previously produced by a process comprising recombinantly preparing a plant by introducing and over-expressing a wild-type or mut-PPO transgene, as described in greater detail hereinafter.

In another preferred embodiment, the plant has been previously produced by a process comprising in situ mutagenizing plant cells, to obtain plant cells which express a mut-PPO.

As disclosed herein, the nucleic acids of the invention find use in enhancing the herbicide tolerance of plants that comprise in their genomes a gene encoding a herbicide-tolerant wild-type or mut-PPO protein. Such a gene may be an endogenous gene or a transgene, as described hereinafter. Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109). The combinations generated can also include multiple copies of any one of the polynucleotides of interest.

In a particularly preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyltransferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD) and dicamba degrading enzymes as disclosed in WO 02/068607, or phenoxyaceticacid- and phenoxypropionicacid-derivative degrading enzymes as disclosed in WO 2008141154 or WO 2005107437.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by benzoxazinone-derivative herbicide of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the benzoxazinone-derivative herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant mut-PPO protein" or "herbicide-resistant mut-PPO protein", it is intended that such a mut-PPO protein displays higher PPO activity, relative to the PPO activity of a wild-type mut-PPO protein, when in the presence of at least one herbicide that is known to interfere with PPO activity and at a concentration or level of the herbicide that is known to inhibit the PPO activity of the wild-type mut-PPO protein. Furthermore, the PPO activity of such a herbicide-tolerant or herbicide-resistant mut-PPO protein may be referred to herein as "herbicide-tolerant" or "herbicide-resistant" PPO activity.

The "benzoxazinone-derivative herbicide" that are useful to carry out the present invention encompasses the benzoxazinones of formula I as depicted in the following:

I

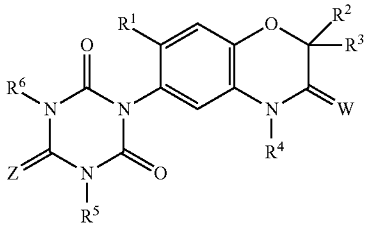

wherein $R^1$ is hydrogen or halogen;

$R^2$ is halogen;

$R^3$ is hydrogen or halogen;

$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$R^5$ is hydrogen, $NH_2$, $C_1$-$C_6$-alkyl or $C_3$-$C_6$-alkynyl;

$R^6$ is hydrogen or $C_1$-$C_6$-alkyl; and

W is O or S;

Z is O or S.

In another preferred embodiment, the "benzoxazinone-derivative herbicide" that are useful to carry out the present invention encompasses the benzoxazinones of formula I as depicted in the following:

A) at least one benzoxazinone of the formula I

I

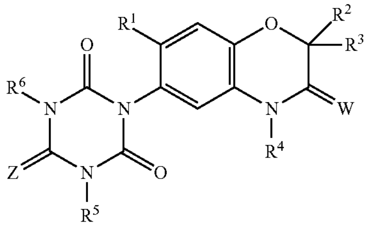

wherein $R^1$ is hydrogen or halogen;

$R^2$ is halogen;

$R^3$ is hydrogen or halogen;

$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$R^5$ is hydrogen, $NH_2$, $C_1$-$C_6$-alkyl or $C_3$-$C_6$-alkynyl;

$R^6$ is hydrogen or $C_1$-$C_6$-alkyl; and

X is O or S;

Y is O or S;

and at least one further active compound selected from

B) herbicides of class b1) to b15):

b1) lipid biosynthesis inhibitors;

b2) acetolactate synthase inhibitors (ALS inhibitors);

b3) photosynthesis inhibitors;

b4) protoporphyrinogen-IX oxidase inhibitors, b5) bleacher herbicides;

b6) enolpyruvyl shikimate 3-phosphate synthase inhibitors (EPSP inhibitors);

b7) glutamine synthetase inhibitors;

b8) 7,8-dihydropteroate synthase inhibitors (DHP inhibitors);

b9) mitose inhibitors;

b10) inhibitors of the synthesis of very long chain fatty acids (VLCFA inhibitors);

b11) cellulose biosynthesis inhibitors;

b12) decoupler herbicides;

b13) auxin herbicides;

b14) auxin transport inhibitors; and b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

and

C) safeners.

The benzoxazinone-derivative herbicide that are useful for the present invention can also be compositions in the form of herbicidally active crop protection compositions comprising a herbicidally effective amount of an active compound combination comprising at least one benzoxazinone of formula I and at least one further compound selected from the herbicides B and the safeners C, as defined above, and also at least one liquid and/or solid carrier and/or one or more surfactants and, if desired, one or more further auxiliaries customary for crop protection compositions.

Further, benzoxazinone-derivative herbicide that are useful for the present invention can also be compositions in the form of a crop protection composition formulated as a 1-component composition comprising an active compound combination comprising at least one benzoxazinone of formula I and at least one further active compound selected from the herbicides B and the safeners C, and at least one solid or liquid carrier and/or one or more surfactants and, if desired, one or more further auxiliaries customary for crop protection compositions.

Further, benzoxazinone-derivative herbicide that are useful for the present invention can also be compositions in the form of a crop protection composition formulated as a 2-component composition comprising a first component comprising at least one benzoxazinone of formula I, a solid or liquid carrier and/or one or more surfactants, and a second component comprising at least one further active compound selected from the herbicides B and safeners C, a solid or liquid carrier and/or one or more surfactants, where additionally both components may also comprise further auxiliaries customary for crop protection compositions.

If the benzoxazinones of formula I as described herein are capable of forming geometrical isomers, for example E/Z isomers, it is possible to use both, the pure isomers and mixtures thereof, in the compositions according to the invention.

If the benzoxazinones of formula I as described herein have one or more centers of chirality and, as a consequence, are present as enantiomers or diastereomers, it is possible to use both, the pure enantiomers and diastereomers and their mixtures, in the compositions according to the invention.

The organic moieties mentioned in the definition of the variables $R^1$ to $R^6$, are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $CO_n$—$C_m$ denoting in each case the possible number of carbon atoms in the group.

Examples of such meanings are:

$C_1$-$C_4$-alkyl and also the $C_1$-$C_4$-alkyl moieties of $C_3$-$C_6$-cycloalkyl-$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of hydroxycarbonyl-$C_1$-$C_4$-alkoxy, $C_1$-$C_6$-alkoxycarbonyl-$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxycarbonyl-$C_1$-$C_4$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

According to a preferred embodiment of the invention preference is also given to those benzoxazinone-derivative of formula I, wherein the variables, either independently of one another or in combination with one another, have the following meanings:

$R^1$ is hydrogen;
- is also preferably halogen, particularly preferred F or Cl, especially preferred F;

$R^2$ is F;

$R^3$ is hydrogen or F, preferably hydrogen;
- is also preferably F;

$R^4$ is $C_3$-$C_6$-alkynyl or $C_3$-$C_6$-halolkynyl, preferably $C_3$-alkynyl or $C_3$-halolkynyl, particularly preferred $CH_2C≡CH$, $CH_2C≡CCl$ or $CH_2C≡CBr$;
- is also preferably $C_3$-$C_6$-alkynyl or $C_3$-$C_6$-cycloalkyl-$C_1$-$C_6$-alkyl, particularly preferred propargyl or cyclopropylmethyl;
- is also preferably $C_3$-$C_6$-alkynyl, preferably $C_3$-alkynyl; particularly preferred $CH_2C≡CH$;
- is also preferably $C_3$-$C_6$-halolkynyl, preferably $C_3$-halolkynyl, particularly preferred $CH_2C≡CCl$ or $CH_2C≡CBr$;

$R^5$ is $NH_2$, $C_1$-$C_6$-Alkyl or $C_3$-$C_6$-alkynyl; preferably $C_1$-$C_6$-alkyl; more preferably $C_1$-$C_4$-alkyl; most preferably $CH_3$;

$R^6$ is $C_1$-$C_6$-alkyl; preferably $C_1$-$C_4$-alkyl; most preferably $CH_3$;

W is O,
- is also preferably S;

Z is O,
- is also preferably S.

Particular preference is given to benzoxazinones of the formula I.a (corresponds to formula I wherein $R^2$ is F, $R^5$ and $R^6$ are $CH_3$, W is O and Z is S), I.a

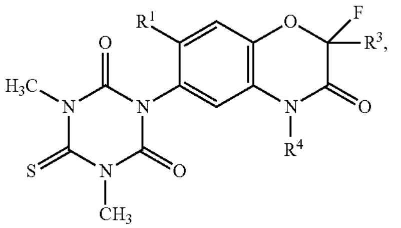

wherein the variables $R^1$, $R^3$, and $R^4$ have the meanings, in particular the preferred meanings, as defined above.

Most preference to the benzoxazinone-derivatives of the formulae I.a.1 to I.a.48 of Table A listed below, in which the variables $R^1$, $R^3$ and $R^4$ together have the meanings given in one row of Table A (benzoxazinones I.a.1 to I.a.54); and where the definitions of the variables $R^1$, $R^2$, $R^3$ and $R^4$ are of particular importance for the compounds according to the invention not only in combination with one another but in each case also on their own.

TABLE A

| No. | $R^1$ | $R^3$ | $R^4$ |
|---|---|---|---|
| I.a.1. | H | H | H |
| I.a.2. | H | H | $CH_3$ |
| I.a.3. | H | H | $C_2H_5$ |
| I.a.4. | H | H | $CH_2—C_2H_5$ |
| I.a.5. | H | H | $CH(CH_3)_2$ |
| I.a.6. | H | H | $CH_2—CH_2—(CH_3)_2$ |
| I.a.7. | H | H | $CH_2—CH═CH_2$ |
| I.a.8. | H | H | $CH_2CCH$ |
| I.a.9. | H | H | $CH_2CC—Br$ |
| I.a.10. | H | F | H |
| I.a.11. | H | F | $CH_3$ |
| I.a.12. | H | F | $C_2H_5$ |
| I.a.13. | H | F | $CH_2—C_2H_5$ |
| I.a.14. | H | F | $CH(CH_3)_2$ |
| I.a.15. | H | F | $CH_2—CH_2—(CH_3)_2$ |
| I.a.16. | H | F | $CH_2—CH═CH_2$ |
| I.a.17. | H | F | $CH_2CCH$ |
| I.a.18. | H | F | $CH_2CC—Br$ |
| I.a.19. | F | H | H |
| I.a.20. | F | H | $CH_3$ |
| I.a.21. | F | H | $C_2H_5$ |
| I.a.22. | F | H | $CH_2—C_2H_5$ |
| I.a.23. | F | H | $CH(CH_3)_2$ |
| I.a.24. | F | H | $CH_2—CH_2—(CH_3)_2$ |
| I.a.25. | F | H | $CH_2—CH═CH_2$ |
| I.a.26. | F | H | $CH_2CCH$ |
| I.a.27. | F | H | $CH_2CC—Br$ |
| I.a.28. | F | F | H |
| I.a.29. | F | F | $CH_3$ |
| I.a.30. | F | F | $C_2H_5$ |
| I.a.31. | F | F | $CH_2—C_2H_5$ |
| I.a.32. | F | F | $CH(CH_3)_2$ |
| I.a.33. | F | F | $CH_2—CH_2—(CH_3)_2$ |
| I.a.34. | F | F | $CH_2—CH═CH_2$ |
| I.a.35. | F | F | $CH_2CCH$ |
| I.a.36. | F | F | $CH_2CC—Br$ |
| I.a.37. | Cl | H | H |
| I.a.38. | Cl | H | $CH_3$ |
| I.a.39. | Cl | H | $C_2H_5$ |
| I.a.40. | Cl | H | $CH_2—C_2H_5$ |
| I.a.41. | Cl | H | $CH(CH_3)_2$ |
| I.a.42. | Cl | H | $CH_2—CH_2—(CH_3)_2$ |
| I.a.43. | Cl | H | $CH_2—CH═CH_2$ |
| I.a.44. | Cl | H | $CH_2CCH$ |
| I.a.45. | Cl | H | $CH_2CC—Br$ |
| I.a.46. | Cl | F | H |
| I.a.47. | Cl | F | $CH_3$ |
| I.a.48. | Cl | F | $C_2H_5$ |
| I.a.49. | Cl | F | $CH_2—C_2H_5$ |
| I.a.50. | Cl | F | $CH(CH_3)_2$ |
| I.a.51. | Cl | F | $CH_2—CH_2—(CH_3)_2$ |
| I.a.52. | Cl | F | $CH_2—CH═CH_2$ |
| I.a.53. | Cl | F | $CH_2CCH$ |
| I.a.54. | Cl | F | $CH_2CC—Br$ |

An especially preferred benzoxazinone of the formula I which, as component A, is part of the composition according to the invention, is the benzoxazinone of formula I.a.35 as defined above According to a particular preferred embodiment of the invention the composition useful for the method of the present invention contains as component A the benzoxazinone of formula I.a.35.

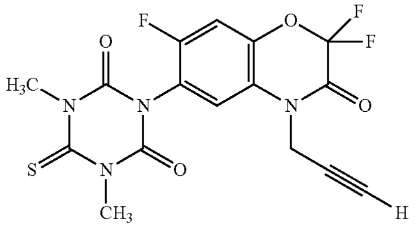

I.a.35

The above described benzoxazinone-derivatives and compositions are disclosed in detail in the European patent application 09163242.2, in particular the disclosures on pages 1 to 7 referring to the bezoxazinone-derivatives and their possible substitutents are entirely incorporated by reference.

The benzoxazinone-derivatives that are useful to carry out the present invention are often best applied in conjunction with one or more other herbicides to obtain control of a wider variety of undesirable vegetation. When used in conjunction with other targeting herbicides, the presently claimed compounds can be formulated with the other herbicide or herbicides, tank mixed with the other herbicide or herbicides, or applied sequentially with the other herbicide or herbicides.

The herbicidal compounds that are useful to carry out the present invention may further be used in conjunction with additional herbicides to which the crop plant is naturally tolerant, or to which it is resistant via expression of one or more additional transgenes as mentioned supra. Some of the herbicides that can be employed in conjunction with the compounds of the present invention include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, imazethapyr, imzapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, aminopyralid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil, metribuzin and mesotrione.

For example, the benzoxazinone-derivative herbicides that are useful to carry out the present invention can be used in conjunction with glyphosate and glufosinate on glyphosate-tolerant or glufosinate-tolerant crops.

Unless already included in the disclosure above, the benzoxazinone-derivative herbicides that are useful to carry out the present invention can, further, be used in conjunction with compounds:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8) and sulfonylaminocarbonyl-triazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn,hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridatre, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione;

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole, clomazone and flumeturon;

b6) from the group of the EPSP synthase inhibitors:

glyphosate, glyphosate-isopropylammonium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitose inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and isoxazoline compounds of the formula II,

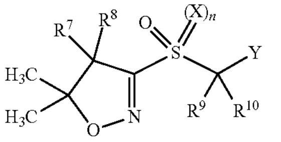

(II)

wherein $R^1$, $R^8$, $R^9$, $R^{10}$, W, Z and n have the following meanings:

$R^1$, $R^8$, $R^9$, $R^{10}$ independently of one another hydrogen, halogen or $C_1$-$C_4$-alkyl;

X oxygen or NH;

Y phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;

preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$; and n zero or one;

among the isoxazoline compounds of the formula II, preference is given to isoxazoline compounds of the formula II, wherein $R^7$, $R^8$, $R^9$, $R^{10}$ independently of one another are H, F, Cl or methyl;

X is oxygen;

n is 0 or 1; and

Y is phenyl, pyrazolyl or 1,2,3-triazolyl, wherein the three last-mentioned radicals are unsubstituted or carry one, two or three substituents $R^{yy}$, especially one of the following radicals

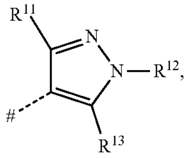

,

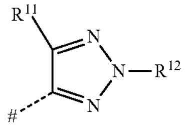

or

-continued

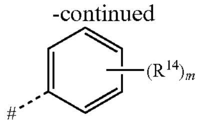

wherein $R^{11}$ is halogen, $C_1$-$C_4$-alkyl or $C_1$-$C_4$-haloalkyl;

$R^{12}$ is $C_1$-$C_4$-alkyl;

$R^{13}$ is halogen, $C_1$-$C_4$-alkoxy or $C_1$-$C_4$-haloalkoxy;

$R^{14}$ is halogen, $C_1$-$C_4$-alkyl, $C_1$-$C_4$-haloalkyl or $C_1$-$C_4$-haloalkoxy;

m is 0, 1, 2 or 3; and # denotes the point of attachment to the group $CR^{13}R^{14}$;

among the isoxazoline compounds of the formula II, particular preference is given to those isoxazoline compounds of the formula II, wherein $R^7$ is hydrogen;

$R^8$ is fluorine;

$R^9$ is hydrogen or fluorine;

$R^{10}$ is hydrogen or fluorine;

X is oxygen;

Y is one of the radicals of the formulae $Y^1$, $Y^2$, $Y^3$ or $Y^4$ $Y^1$

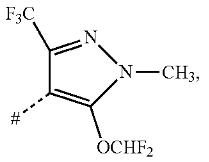

$Y^2$

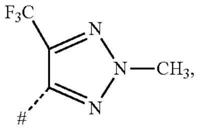

$Y^3$

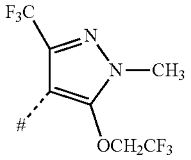

or $Y^4$

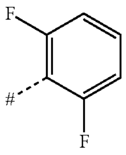

wherein #denotes the point of attachment to the group $CR^9R^{10}$;

n is zero or 1, in particular 1; and among these, especially preferred are the isoxazoline compounds of the formulae II.1, II.2, II.3, II.4, II.5, II.6, II.7, II.8 and II.9

II.1

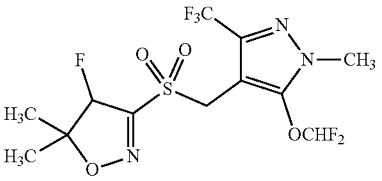

II.2

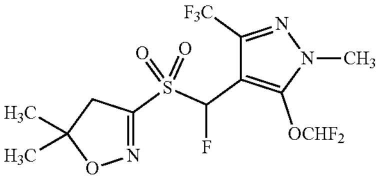

II.3

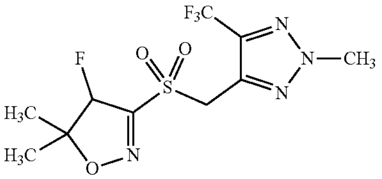

II.4

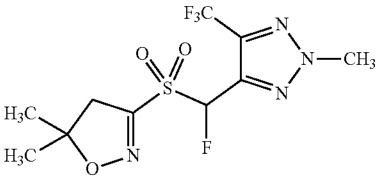

II.5

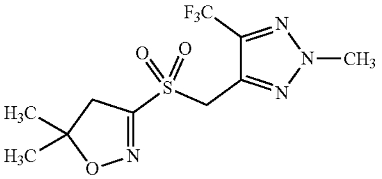

II.6

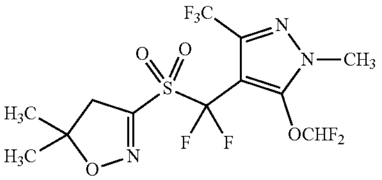

II.7

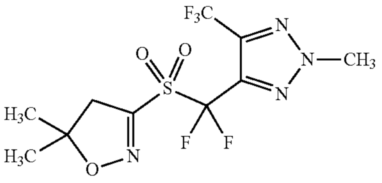

II.8

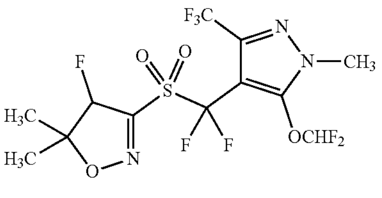

-continued

II.9

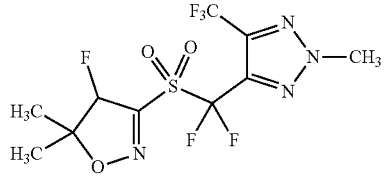

the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides, especially to pyroxasulfone;

b11) from the group of the cellulose biosynthesis inhibitors:

chlorthiamid, dichlobenil, flupoxam, isoxaben, 1-Cyclohexyl-5-pentafluorphenyloxy-14-[1,2,4,6]thiatriazin-3-ylamine and piperazine compounds of formula III,

III

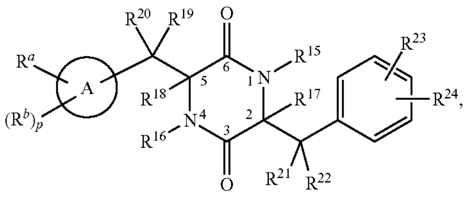

in which

A is phenyl or pyridyl where $R^a$ is attached in the ortho-position to the point of attachment of A to a carbon atom;

$R^a$ is CN, $NO_2$, $C_1$-$C_4$-alkyl, D-$C_3$-$C_6$-cycloalkyl, $C_1$-$C_4$-haloalkyl, $C_1$-$C_4$-alkoxy, $C_1$-$C_4$-haloalkoxy, O-D-$C_3$-$C_6$-cycloalkyl, $S(O)_qR^y$, $C_2$-$C_6$-alkenyl, D-$C_3$-$C_6$-cycloalkenyl, $C_3$-$C_6$-alkenyloxy, $C_2$-$C_6$-alkynyl, $C_3$-$C_6$-alkynyloxy, $NR^AR^B$, tri-1-$O_4$-alkylsilyl, $R^{a1}$, D-P(=O)$(R^{a1})_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups $R^{aa}$ and/or $R^{a1}$, and, if $R^a$ is attached to a carbon atom, additionally halogen;

$R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A$,$R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$,$R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond, $C_1$-$C_4$-alkylene, $C_2$-$C_6$-alkenyl or $C_2$-$C_6$-alkynyl;

$R^{a1}$ is hydrogen, OH, $C_1$-$C_3$-Alkyl, $C_1$-$C_4$-haloalkyl, $C_3$-$C_6$-cycloalkyl, $C_2$-$C_3$-alkenyl, $C_5$-$C_6$-cycloalkenyl, $C_2$-$C_3$-alkynyl, $C_1$-$C_6$-alkoxy, $C_1$-$C_4$-haloalkoxy, $C_3$-$C_3$-alkenyloxy, $C_3$-$C_3$-alkynyloxy, $NR^AR^B$, $C_1$-$C_6$-alkoxyamino, $C_1$-$C_6$-alkylsulfonylamino, $C_1$-$C_6$-alkylaminosulfonylamino, [di-($C_1$-$C_6$)alkylamino]sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N—($C_1$-$C_6$-alkoxy)-N—($C_1$-$C_6$-alkyl)amino, N—($C_2$-$C_6$-alkenyl)-N—($C_1$-$C_6$-alkoxy)amino, N—($C_2$-$C_6$-alkynyl)-N—($C_1$-$C_6$-alkoxy)-amino, $C_1$-$C_6$-alkylsulfonyl, tri-$C_1$-$C_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^{aa}$;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_qR^y$, D-C(=O)—$R^{a1}$ and tri-$C_1$-$C_4$-alkylsilyl;

$R^b$ independently of one another are hydrogen, CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_qR^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0, 1, 2 or 3;

$R^{15}$ is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, C(=O)$R^{25}$, $CONR^AR^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl, $C_3$-$C_4$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, C(=O)$R^{25}$, $CONR^AR^B$;

preferably is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^AR^B$, $S(O)_nR^Y$, $S(O)_nNR^AR^B$, C(=O)$R^{25}$, $CONR^AR^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl and $C_3$-$C_4$-alkynyl;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

$D^1$ is carbonyl or a group D;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl, $C_3$-$C_4$-alkenyl or $C_3$-$C_4$-alkynyl;

$R^{17}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or C(═O)$R^{25}$;

$R^{18}$ is hydrogen, halogen, $C_1$-$C_4$-alkyl or $C_1$-$C_4$-haloalkyl, or $R^{18}$ and $R^{19}$ together are a covalent bond;

$R^{19}$, $R^{20}$, $R^{21}$, $R^{21}$ independently of one another are hydrogen, halogen, OH, CN, $NO_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{23}$, $R^{24}$ independently of one another are hydrogen, halogen, OH, haloalkyl, $NR^AR^B$, $NR^AC(O)R^{26}$, CN, $NO_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{26}$, phenoxy or benzyloxy, where in groups $R^{23}$ and $R^{24}$ the carbon chains and/or the cyclic groups may carry 1, 2, 3 or 4 substituents $R^{aa}$;

$R^{26}$ is $C_1$-$C_4$-alkyl or $NR^AR^B$;

among the isoxazoline compounds of the piperazin compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(═O)—$R^{a1}$;

$R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A$,$R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$,$R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_qR^y$, D-C(═O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_qR^Y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{15}$ is hydrogen, $C_1$-$C_{12}$-alkyl, $C_3$-$C_{12}$-alkenyl, $C_3$-$C_{12}$-alkynyl, $C_1$-$C_4$-alkoxy or C(═O)$R^{25}$, which can be partially or fully substituted by $R^{aa}$-groups; preferably is hydrogen, $C_1$-$C_{12}$-alkyl, $C_3$-$C_{12}$-alkenyl, $C_3$-$C_{12}$-alkynyl, $C_1$-$C_4$-alkoxy or C(═O)$R^{25}$;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy; where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl;

$R^{17}$ is OH, $NH_2$, $C_1$-$C_4$-alkyl, $C_3$-$C_6$-cycloalkyl, $C_1$-$C_4$-haloalkyl or C(═O)$R^{25}$ $R^{18}$ is hydrogen, or $R^{18}$ and $R^{19}$ together are a covalent bond;

$R^{19}$, $R^{20}$, $R^{21}$, $R^{21}$ independently of one another are hydrogen;

$R^{23}$, $R^{24}$ independently of one another are hydrogen, halogen or OH;

b12) from the group of the decoupler herbicides: dinoseb, dinoterb and DNOC and its salts;

b13) from the group of the auxin herbicides: 2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Moreover, it may be useful to apply the benzoxazinones of the formula I in combination with safeners. Safeners are chemical compounds which prevent or reduce damage on useful plants without having a major impact on the herbicidal action of the benzoxazinones of the formula I towards unwanted plants. They can be applied either before sowings (e.g. on seed treatments, shoots or seedlings) or in the pre-emergence application or post-emergence application of the useful plant.

Furthermore, the safeners C, the benzoxazinones I and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4), and N-(2-Methoxybenzoyl)-4-[(methylaminocarbonyl)amino]benzenesulfonamide (CAS 129531-12-0).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MN4660, CAS 71526-07-3) and 2,2,5-trimethyl-3-(dichloroacetyl)-1,3-oxazolidine (R-29148, CAS 52836-31-4), and N-(2-Methoxybenzoyl)-4-[(methylaminocarbonyl)amino]benzenesulfonamide (CAS 129531-12-0).

Particularly preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro-[4.5]decane (MON4660, CAS 71526-07-3) and 2,2,5-trimethyl-3-(dichloroacetyl)-1,3-oxazolidine (R-29148, CAS 52836-31-4), and N-(2-Methoxybenzoyl)-4-[(methylaminocarbonyl)amino]benzenesulfonamide (CAS 129531-12-0).

Particularly preferred safeners C, which, as component C, are constituent of the composition according to the invention are the safeners C as defined above; in particular the safeners 0.1-0.13 listed below in table C:

TABLE C

| Safener C |
|---|
| C.1 benoxacor |
| C.2 cloquintocet |
| C.3 cyprosulfamide |
| C.4 dichlormid |
| C.5 fenchlorazole |
| C.6 fenclorim |
| C.7 furilazole |
| C.8 isoxadifen |
| C.9 mefenpyr |
| C.10 naphtalic acid anhydride |
| C.11 4-(dichloroacetyl)-1-oxa-4-azaspiro[4.5]decane (MON4660, CAS 71526-07-3) |
| C.12 2,2,5-trimethyl-3-(dichloro-acetyl)-1,3-oxazolidine (R-29148, CAS 52836-31-4) |
| C.13 N-(2-Methoxybenzoyl)-4-[(methylaminocarbonyl)amino]benzenesulfonamide (CAS 129531-12-0) |

The active compounds B of groups b1) to b15) and the active compounds C are known herbicides and safeners, see, for example, The Compendium of Pesticide Common Names (alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-31-4] is also referred to as AD-67 and MON 4660. Further herbicidally active compounds are known from WO 96/26202, WO 97/41116, WO 97/41117, WO 97/41118 and WO 01/83459 and also from W. Krämer et al. (ed.) "Modern Crop Protection Compounds", Vol. 1, Wiley VCH, 2007 and the literature cited therein.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

It is recognized that the polynucleotide molecules and polypeptides of the invention encompass polynucleotide molecules and polypeptides comprising a nucleotide or an amino acid sequence that is sufficiently identical to nucleotide sequences set forth in SEQ ID Nos: 1, 3, 5, 7, 9, 11, 13, 15, 17, 19, 21, 23, 25, 27, 29, 31, 33, 35, 37, 39, 41, 43, or 45, or to the amino acid sequences set forth in SEQ ID Nos: 2, 4, 6, 8, 10, 12, 14, 16, 18, 20, 22, 24, 26, 28, 30, 32, 34, 36, 38, 40, 42, 44, or 46. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mut-PPO nucleic acid" refers to a PPO nucleic acid having a sequence that is mutated from a wild-type PPO nucleic acid and that confers increased benzoxazinone-derivative herbicide tolerance to a plant in which it is expressed. Furthermore, the term "mutated protoporphyrinogen oxidase (mut-PPO)" refers to the replacement of an amino acid of the wild-type primary sequences SEQ ID NO: 2, 4, 6, 8, 10, 12, 14, 16, 18, 20, 22, 24, 26, 28, 30, 32, 34, 36, 38, 40, 42, 44, or 46, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the PPO nucleotide sequence comprises the sequence of SEQ ID NO: 1, 25, 37 or 39 or a variant or derivative thereof.

Furthermore, it will be understood by the person skilled in the art that the PPO nucleotide sequences encompassed homologues, paralogues and and orthologues of SEQ ID NO: 1, 25, 37 or 39 as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: SEQ ID NO: 1, 3, 5, 7, 9, 11, 13, 15, 17, 19, 21, 23, 25, 27, 29, 31, 33, 35, 37, 39, 41, 43, or 45. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the PPO polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 2, 4, 6, 8, 10, 12, 14, 16, 18, 20, 22, 24, 26, 28, 30, 32, 34, 36, 38, 40, 42, 44, or 46.

By "variant" polypeptide is intended a polypeptide derived from the protein of SEQ ID NO: 2, 4, 6, 8, 10, 12, 14, 16, 18, 20, 22, 24, 26, 28, 30, 32, 34, 36, 38, 40, 42, 44, or 46 by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 2

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, OH), QuickChange Site Directed mutagenesis (Stratagene, San Diego, CA), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. A non-limiting list of examples of such orthologues are shown in Table 1.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc.

Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have found that by substituting one or more of the key amino acid residues the herbicide tolerance or resistance could be remarkably increased as compared to the activity of the wild type PPO enzymes with SEQ ID NO: 2, 4, 6, 8, 10, 12, 14, 16, 18, 20, 22, 24, 26, 28, 30, 32, 34, 36, 38, 40, 42, 44, or 46. Preferred substitutions of mut-PPO are those that increase the herbicide tolerance of the plant, but leave the biological activity of the oxidase activity substantially unaffected.

Accordingly, in another object of the present invention the key amino acid residues of a PPO enzyme, a variant, derivative, orthologue, paralogue or homologue thereof, is substituted by any other amino acid.

In a preferred embodiment, the key amino acid residues of a PPO enzyme, a variant, derivative, orthologue, paralogue or homologue thereof, is substituted by a conserved amino acid as depicted in Table 2.

It will be understood by the person skilled in the art that amino acids located in a close proximity to the positions of amino acids mentioned below may also be substituted. Thus, in another embodiment the variant of SEQ ID NO: 2, 4, 6, 8, 10, 12, 14, 16, 18, 20, 22, 24, 26, 28, 30, 32, 34, 36, 38, 40, 42, 44, or 46, a variant, derivative, orthologue, paralogue or homologue thereof comprises a mut-PPO, wherein an amino acid ±3, ±2 or ±1 amino acid positions from a key amino acid is substituted by any other amino acid.

Based on techniques well-known in the art, a highly characteristic sequence pattern can be developed, by means of which further of mut-PPO candidates with the desired activity may be searched.

Searching for further mut-PPO candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, 5, 3, ±2 or ±1 amino acid positions without substantially affecting the desired activity.

Furthermore, by applying the method of site directed mutagenesis, the inventors of the present invention have identified specific combinations of mutations, which combination refers to a substitution of the Phenylalanine residue at position 420 in SEQ ID NO:2 or 4, combined with a second substitution of the Leucin at position 397 in SEQ ID NO:2 or 4.

Thus, in a particularly preferred embodiment, the variant or derivative of the mut-PPO of SEQ ID NO: 2 or SEQ ID NO: 4 is selected from the combined amino acid substitutions of the following Table 3a.

TABLE 3a

SEQ ID NO: 2 or SEQ ID NO: 4 (combined amino acid substitutions obtained by site directed mutagenesis.)

| Combination Number | SEQ ID NO: | Key amino acid position combination | Preferred Substitution |
|---|---|---|---|
| 1 | 2 or 4 | Leu397 | Gly |
| | | Phe420 | Met |
| 2 | 2 or 4 | Leu397 | Ala |
| | | Phe420 | Met |
| 3 | 2 or 4 | Leu397 | Ser |
| | | Phe420 | Met |
| 4 | 2 or 4 | Leu397 | Thr |
| | | Phe420 | Met |
| 5 | 2 or 4 | Leu397 | Cys |
| | | Phe420 | Met |
| 6 | 2 or 4 | Leu397 | Val |
| | | Phe420 | Met |
| 7 | 2 or 4 | Leu397 | Ile |
| | | Phe420 | Met |
| 8 | 2 or 4 | Leu397 | Met |
| | | Phe420 | Met |
| 9 | 2 or 4 | Leu397 | Pro |
| | | Phe420 | Met |
| 10 | 2 or 4 | Leu397 | Phe |
| | | Phe420 | Met |
| 11 | 2 or 4 | Leu397 | Tyr |
| | | Phe420 | Met |
| 12 | 2 or 4 | Leu397 | Trp |
| | | Phe420 | Met |
| 13 | 2 or 4 | Leu397 | Asp |

TABLE 3a-continued

| SEQ ID NO: 2 or SEQ ID NO: 4 (combined amino acid substitutions obtained by site directed mutagenesis.) | | | |
|---|---|---|---|
| Combination Number | SEQ ID NO: | Key amino acid position combination | Preferred Substitution |
| | | Phe420 | Met |
| 14 | 2 or 4 | Leu397 | Glu |
| | | Phe420 | Met |
| 15 | 2 or 4 | Leu397 | Asn |
| | | Phe420 | Met |
| 16 | 2 or 4 | Leu397 | Gln |
| | | Phe420 | Met |
| 17 | 2 or 4 | Leu397 | His |
| | | Phe420 | Met |
| 18 | 2 or 4 | Leu397 | Lys |
| | | Phe420 | Met |
| 19 | 2 or 4 | Leu397 | Arg |
| | | Phe420 | Met |
| 20 | 2 or 4 | Leu397 | Gly |
| | | Phe420 | Val |
| 21 | 2 or 4 | Leu397 | Ala |
| | | Phe420 | Val |
| 22 | 2 or 4 | Leu397 | Ser |
| | | Phe420 | Val |
| 23 | 2 or 4 | Leu397 | Thr |
| | | Phe420 | Val |
| 24 | 2 or 4 | Leu397 | Cys |
| | | Phe420 | Val |
| 25 | 2 or 4 | Leu397 | Val |
| | | Phe420 | Val |
| 26 | 2 or 4 | Leu397 | Ile |
| | | Phe420 | Val |
| 27 | 2 or 4 | Leu397 | Met |
| | | Phe420 | Val |
| 28 | 2 or 4 | Leu397 | Pro |
| | | Phe420 | Val |
| 29 | 2 or 4 | Leu397 | Phe |
| | | Phe420 | Val |
| 30 | 2 or 4 | Leu397 | Tyr |
| | | Phe420 | Val |
| 31 | 2 or 4 | Leu397 | Trp |
| | | Phe420 | Val |
| 32 | 2 or 4 | Leu397 | Asp |
| | | Phe420 | Val |
| 33 | 2 or 4 | Leu397 | Glu |
| | | Phe420 | Val |
| 34 | 2 or 4 | Leu397 | Asn |
| | | Phe420 | Val |
| 35 | 2 or 4 | Leu397 | Gln |
| | | Phe420 | Val |
| 36 | 2 or 4 | Leu397 | His |
| | | Phe420 | Val |
| 37 | 2 or 4 | Leu397 | Lys |
| | | Phe420 | Val |
| 38 | 2 or 4 | Leu397 | Arg |
| | | Phe420 | Val |

In a further particularly preferred embodiment, the variant or derivative of the mut-PPO of SEQ ID NO: 2 or SEQ ID NO: 4 is selected from the combined amino acid substitutions of the following Table 3b.

TABLE 3b

| SEQ ID NO: 2 or SEQ ID NO: 4 (combined amino acid substitutions) | | | |
|---|---|---|---|
| Combination Number | SEQ ID NO: | Key amino acid position combination | Preferred Substitution |
| 39 | 2 or 4 | Leu397 | Asp, Glu, Gln, Asn |
| | | Leu400 | Ala, Ile, Val, Met |
| 40 | 2 or 4 | Leu397 | Asp, Glu, Gln, Asn |
| | | Phe457 | Met, Ala, Leu, Ile, Val |

TABLE 3b-continued

| SEQ ID NO: 2 or SEQ ID NO: 4 (combined amino acid substitutions) | | | |
|---|---|---|---|
| Combination Number | SEQ ID NO: | Key amino acid position combination | Preferred Substitution |
| 41 | 2 or 4 | Phe204 | Ala, Leu, Ile, Val |
| | | Leu397 | Asp, Glu, Gln, Asn |
| 42 | 2 or 4 | Thr208 | Ser |
| | | Leu400 | Ala, Ile, Val, Met |
| 43 | 2 or 4 | Leu400 | Ala |
| | | Phe457 | Met, Ala, Leu, Ile, Val |
| 44 | 2 or 4 | Phe204 | Ile |
| | | Leu400 | Ala, Ile, Val, Met |
| 45 | 2 or 4 | The208 | Ser |
| | | Phe457 | Met, Ala, Leu, Ile, Val |
| 46 | 2 or 4 | Phe204 | Ile |
| | | Thr208 | Ser |
| 47 | 2 or 4 | Phe204 | Ile |
| | | Phe457 | Met, Ala, Leu, Ile, Val |
| 48 | 2 or 4 | Leu400 | Ala, Ile, Val, Met |
| | | Phe420 | Val, Met, Ala, Ile, Leu |
| 49 | 2 or 4 | Phe204 | Ile |
| | | Phe420 | Val, Met, Ala, Ile, Leu |
| 50 | 2 or 4 | Phe420 | Val, Met, Ala, Ile, Leu |
| | | Phe457 | Met, Ala, Leu, Ile, Val |
| 51 | 2 or 4 | Arg128 | Ala, Leu, Ile, Val |
| | | Leu397 | Asp, Glu, Gln, Asn |
| 52 | 2 or 4 | Thr208 | Ser |
| | | Leu397 | Asp, Glu, Gln, Asn |
| | | Phe457 | Met, Ala, Leu, Ile, Val |
| 53 | 2 or 4 | Phe204 | Ile |
| | | The208 | Ser |
| | | Leu397 | Asp, Glu, Gln, Asn |
| 54 | 2 or 4 | Phe204 | Ile |
| | | Leu397 | Asp, Glu, Gln, Asn |
| | | Phe457 | Met, Ala, Leu, Ile, Val |
| 55 | 2 or 4 | Thr208 | Ser |
| | | Leu400 | Ala, Ile, Val, Met |
| | | Phe457 | Met, Ala, Leu, Ile, Val |
| 56 | 2 or 4 | Phe204 | Ile |
| | | Thr208 | Ser |
| | | Leu400 | Ala, Ile, Val, Met |
| 57 | 2 or 4 | Phe204 | Ile |
| | | Leu400 | Ala, Ile, Val, Met |
| | | Phe457 | Met, Ala, Leu, Ile, Val |
| 58 | 2 or 4 | Thr208 | Ser |
| | | Leu397 | Asp, Glu, Gln, Asn |
| | | Leu400 | Ala, Ile, Val, Met |
| 59 | 2 or 4 | Leu397 | Asp, Glu, Gln, Asn |
| | | Leu400 | Ala, Ile, Val, Met |
| | | Phe457 | Met, Ala, Leu, Ile, Val |
| 60 | 2 or 4 | Phe204 | Ile |
| | | Leu397 | Asp, Glu, Gln, Asn |
| | | Leu400 | Ala, Ile, Val, Met |
| 61 | 2 or 4 | Phe204 | Ile |
| | | Thr208 | Ser |
| | | Phe457 | Met, Ala, Leu, Ile, Val |
| 62 | 2 or 4 | Leu397 | Asp, Glu, Gln, Asn |
| | | Leu400 | Ala, Ile, Val, Met |
| | | Phe420 | Met, Ala, Leu, Ile, Val |
| 63 | 2 or 4 | Leu397 | Asp, Glu, Gln, Asn |
| | | Phe420 | Met, Ala, Leu, Ile, Val |
| | | Phe457 | Met, Ala, Leu, Ile, Val |
| 64 | 2 or 4 | Phe204 | Ile |
| | | Leu397 | Asp, Glu, Gln, Asn |
| | | Phe420 | Met, Ala, Leu, Ile, Val |
| 65 | 2 or 4 | Phe204 | Ile |
| | | Thr208 | Ser |
| | | Phe420 | Met, Ala, Leu, Ile, Val |
| 66 | 2 or 4 | Thr208 | Ser |
| | | Phe420 | Met, Ala, Leu, Ile, Val |
| | | Phe457 | Met, Ala, Leu, Ile, Val |
| 67 | 2 or 4 | Phe204 | Ile |
| | | Phe420 | Met, Ala, Leu, Ile, Val |
| | | Phe457 | Met, Ala, Leu, Ile, Val |
| 68 | 2 or 4 | Arg128 | Ala, Leu, Ile, Val |
| | | Leu400 | Ala, Ile, Val, Met |
| | | Phe420 | Met, Ala, Leu, Ile, Val |

TABLE 3b-continued

| SEQ ID NO: 2 or SEQ ID NO: 4 (combined amino acid substitutions) | | | |
|---|---|---|---|
| Combination Number | SEQ ID NO: | Key amino acid position combination | Preferred Substitution |
| 69 | 2 or 4 | Arg128 | Ala, Leu, Ile, Val |
| | | Leu397 | Asp, Glu, Gln, Asn |
| | | Phe420 | Met, Ala, Leu, Ile, Val |
| 70 | 2 or 4 | Arg128 | Ala, Leu, Ile, Val |
| | | Phe204 | Ile |
| | | Phe420 | Met, Ala, Leu, Ile, Val |
| 71 | 2 or 4 | Arg128 | Ala, Leu, Ile, Val |
| | | Phe420 | Met, Ala, Leu, Ile, Val |
| | | Phe457 | Met, Ala, Leu, Ile, Val |
| 72 | 2 or 4 | Thr208 | Ser |
| | | Leu400 | Ala, Ile, Val, Met |
| | | Phe420 | Met, Ala, Leu, Ile, Val |
| 73 | 2 or 4 | Leu400 | Ala, Ile, Val, Met |
| | | Phe420 | Met, Ala, Leu, Ile, Val |
| | | Phe457 | Met, Ala, Leu, Ile, Val |
| 74 | 2 or 4 | Phe204 | Ile |
| | | Leu400 | Ala, Ile, Val, Met |
| | | Phe420 | Met, Ala, Leu, Ile, Val |
| 75 | 2 or 4 | Phe204 | Ile |
| | | Thr208 | Se |
| | | Leu400 | Ala, Ile, Val, Met |
| | | Phe457 | Met, Ala, Leu, Ile, Val |
| 76 | 2 or 4 | Phe204 | Ile |
| | | Thr208 | Ser |
| | | Phe420 | Met, Ala, Leu, Ile, Val |
| | | Phe457 | Met, Ala, Leu, Ile, Val |
| 77 | 2 or 4 | Arg128 | Ala, Leu, Ile, Val |
| | | Phe204 | Ile |
| | | Phe420 | Met, Ala, Leu, Ile, Val |
| | | Phe457 | Met, Ala, Leu, Ile, Val |
| 78 | 2 or 4 | Phe204 | Ile |
| | | Leu400 | Ala, Ile, Val, Met |
| | | Phe420 | Met, Ala, Leu, Ile, Val |
| | | Phe457 | Met, Ala, Leu, Ile, Val |
| 79 | 2 or 4 | Phe204 | Ile |
| | | Thr208 | Ser |
| | | Leu397 | Asp, Glu, Gln, Asn |
| | | Leu400 | Ala, Ile, Val, Met |
| 80 | 2 or 4 | Phe204 | Ile |
| | | Thr208 | Ser |
| | | Leu400 | Ala, Ile, Val, Met |
| | | Phe420 | Met, Ala, Leu, Ile, Val |
| | | Phe457 | Met, Ala, Leu, Ile, Val |
| 81 | 2 or 4 | Arg128 | Ala, Leu, Ile, Val |
| | | Phe204 | Ile |
| | | Leu400 | Ala, lle, Val, Met |
| | | Phe420 | Met, Ala, Leu, Ile, Val |
| | | Phe457 | Met, Ala, Leu, Ile, Val |

It is to be understood that any amino acid besides the ones mentioned in the above tables 3 could be used as a substitutent. Assays to test for the functionality of such mutants are readily available in the art, and respectively, described in the Example section of the present invention.

In a preferred embodiment, the amino acid sequence differs from an amino acid sequence of a PPO of SEQ ID NO: 2 or SEQ ID NO: 4 at one or more of the following positions: 128, 204, 208, 397, 400, 420, 457.

Examples of differences at these amino acid positions include, but are not limited to, one or more of the following:

the amino acid at position 128 is other than Arginine;
the amino acid at position 204 is other than Phenylalanine;
the amino acid at position 208 is other than Threonine;
the amino acid at position 397 is other than Leucine,
the amino acid at position 400 is other than Leucine,
the amino acid at position 420 is other than Phenylalanine,
the amino acid at position 457 is other than Phenylalanine.

In some embodiments, the mut-PPO enzyme of SEQ ID NO: 2 or SEQ ID NO: 4 comprises one or more of the following:

the amino acid at position 128 is Leu, Ala, Val, or lie;
the amino acid at position 204 is Ala, Leu, lie, or Val;
the amino acid at position 208 is Ser;
the amino acid at position 397 is Gly, Ala, Ser, Thr, Cys, Val, lie, Met, Pro, Phe, Tyr, Trp, His, Lys, Arg, Asn, Asp, Glu, or Gln;
the amino acid at position 400 is Ala, lie, Val, or Met;
the amino acid at position 420 is Val, Met, Ala, lie, or Leu;
the amino acid at position 457 is Met, Ala, Leu, lie, Val;

In a preferred embodiment, the mut-PPO comprises a sequence of SEQ ID NO: 2 or SEQ ID NO:4, a variant, derivative, orthologue, paralogue or homologue thereof, in which: the amino acid at position 420 is Met, and the the amino acid at position 397 is Gly, Ala, Ser, Thr, Cys, Val, lie, Met, Pro, Phe, Tyr, Trp, His, Lys, Arg, Asn, Asp, Glu, or Gln.

In another preferred embodiment, the mut-PPO comprises a sequence of SEQ ID NO: 2 or SEQ ID NO:4, a variant, derivative, orthologue, paralogue or homologue thereof, in which: the amino acid at position 420 is Val, and the the amino acid at position 397 is Gly, Ala, Ser, Thr, Cys, Val, lie, Met, Pro, Phe, Tyr, Trp, His, Lys, Arg, Asn, Asp, Glu, or Gln.

In another preferred embodiment, the mut-PPO comprises a sequence of SEQ ID NO: 2 or SEQ ID NO:4, a variant, derivative, orthologue, paralogue or homologue thereof, in which: the amino acid at position 397 is Asn, Asp, Glu, or Gln, and the amino acid at position 400 is Ala, lie, Val, or Met.

In another preferred embodiment, the mut-PPO comprises a sequence of SEQ ID NO: 2 or SEQ ID NO:4, a variant, derivative, orthologue, paralogue or homologue thereof, in which: the amino acid at position 397 is Asn, Asp, Glu, or Gln, and the amino acid at position 457 is Met, Ala, Leu, lie, or Val.

In another preferred embodiment, the mut-PPO comprises a sequence of SEQ ID NO: 2 or SEQ ID NO:4, a variant, derivative, orthologue, paralogue or homologue thereof, in which: the amino acid at position 204 is Ala, Leu, lie, or Val, and the amino acid at position 397 is Asn, Asp, Glu, or Gln.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, and the amino acid at position 400 is Ala, lie, Val, or Met.

In another preferred embodiment, the mut-PPO comprises a sequence of SEQ ID NO: 2 or SEQ ID NO:4 a variant, derivative, orthologue, paralogue or homologue thereof, in which: the amino acid at position 400 is Ala, lie, Val, or Met, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, and the amino acid at position 400 is Ala, Ile, Val, or Met.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, and the amino acid at position 208 is Ser.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 400 is Ala, lie, Val, or Met, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, and the amino acid at position 397 is Asn, Asp, Glu, or Gln.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, the amino acid at position 397 is Asn, Asp, Glu, or Gln, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, and the amino acid at position 397 is Asn, Asp, Glu, or Gln.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 397 is Asn, Asp, Glu, or Gln, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, the amino acid at position 400 is Ala, lie, Val, or Met, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, and the amino acid at position 400 is Ala, lie, Val, or Met.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 400 is Ala, lie, Val, or Met, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, the amino acid at position 397 is Asn, Asp, Glu, or Gln, and the amino acid at position 400 is Ala, lie, Val, or Met.

In another preferred embodiment, the mut-PPO comprises a sequence of SEQ ID NO: 2 or SEQ ID NO:4 a variant, derivative, orthologue, paralogue or homologue thereof, in which: the amino acid at position 397 is Asn, Asp, Glu, or Gln, the amino acid at position 400 is Ala, lie, Val, or Met, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 397 is Asn, Asp, Glu, or Gln, and the amino acid at position 400 is Ala, lie, Val, or Met.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 397 is Asn, Asp, Glu, or Gln, the amino acid at position 400 is Ala, lie, Val, or Met, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 397 is Asn, Asp, Glu, or Gln, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 397 is Asn, Asp, Glu, or Gln, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, the amino acid at position 400 is Ala, lie, Val, or Met, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, the amino acid at position 397 is Asn, Asp, Glu, or Gln, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, the amino acid at position 204 is Ala, Leu, lie, or Val, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 208 is Ser, the amino acid at position 400 is Ala, lie, Val, or Met, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 400 is Ala, lie, Val, or Met, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 400 is Ala, lie, Val, or Met, and the amino acid at position 420 is Val, Met, Ala, lie, or Leu.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, the amino acid at position 400 is Ala, lie, Val, or Met, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, the amino acid at position 204 is Ala, Leu, lie, or Val, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 400 is Ala, lie, Val, or Met, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, the amino acid at position 397 is Asn, Asp, Glu, or Gln, and the amino acid at position 400 is Ala, lie, Val, or Met.

In another preferred embodiment, the mut-PPO comprises a sequence of SEQ ID NO: 2 or SEQ ID NO:4 a variant, derivative, orthologue, paralogue or homologue thereof, in which: the amino acid at position 204 is Ala, Leu, lie, or Val, the amino acid at position 208 is Ser, the amino acid at position 400 is Ala, lie, Val, or Met, the amino acid at position 420 is Val, Met, Ala, lie, or Leu, and the amino acid at position 457 is Met, Ala, Leu, lie, or Val.

In another preferred embodiment, the mut-PPO comprises a sequence of SEQ ID NO: 2 or SEQ ID NO:4 a variant, derivative, orthologue, paralogue or homologue thereof, in which: the amino acid at position 128 is Leu, Ala, Val, or lie, the amino acid at position 204 is Ala, Leu, lie, or Val, the amino acid at position 400 is Ala, lie, Val, or Met, the amino acid at position 420 is Val, Met, Ala, lie, or Leu, and the amino acid at position 457 is Met, Ala, Leu, lie, or Val.

It will be within the knowledge of the skilled artisan to identify conserved regions and motifs shared between the homologues, orthologues and paralogues encoded by SEQ ID NO: 1, 3, 5, 7, 9, 11, 13, 15, 17, 19, 21, 23, 25, 27, 29, 31, 33, 35, 37, 39, 41, 43, or 45, such as those depicted in Table 1. Having identified such conserved regions that may represent suitable binding motifs, amino acids corresponding to the amino acids listed in Table 3a and 3b, can be chosen to be substituted by any other amino acid, preferably by conserved amino acids as shown in table 2, and more preferably by the amino acids of tables 3a and 3b.

In addition, the present invention refers to a method for identifying a benzoxazinone-derivative herbicide by using a mut-PPO encoded by a nucleic acid which comprises the nucleotide sequence of SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof.

Said method comprises the steps of:

a) generating a transgenic cell or plant comprising a nucleic acid encoding a mut-PPO, wherein the mut-PPO is expressed;
b) applying a benzoxazinone-derivative herbicide to the transgenic cell or plant of a) and to a control cell or plant of the same variety;
c) determining the growth or the viability of the transgenic cell or plant and the control cell or plant after application of said benzoxazinone-derivative herbicide, and
d) selecting "benzoxazinone-derivative herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mut-PPO which is resistant or tolerant to a benzoxazinone-derivative herbicide, the method comprising:

a) generating a library of mut-PPO-encoding nucleic acids,
b) screening a population of the resulting mut-PPO-encoding nucleic acids by expressing each of said nucleic acids in a cell or plant and treating said cell or plant with a benzoxazinone-derivative herbicide,
c) comparing the benzoxazinone-derivative herbicide-tolerance levels provided by said population of mut-PPO encoding nucleic acids with the benzoxazinone-derivative herbicide-tolerance level provided by a control PPO-encoding nucleic acid,
d) selecting at least one mut-PPO-encoding nucleic acid that provides a significantly increased level of tolerance to a benzoxazinone-derivative herbicide as compared to that provided by the control PPO-encoding nucleic acid.

In a preferred embodiment, the mut-PPO-encoding nucleic acid selected in step d) provides at least 2-fold as much resistance or tolerance of a cell or plant to a benzoxazinone-derivative herbicide as compared to that provided by the control PPO-encoding nucleic acid.

In a further preferred embodiment, the mut-PPO-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a benzoxazinone-derivative herbicide as compared to that provided by the control PPO-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a wild-type or mut-PPO which is resistant or tolerant to a benzoxazinone-derivative herbicide, the method comprising:

a) identifying an effective amount of a benzoxazinone-derivative herbicide in a culture of plant cells or green algae that leads to death of said cells.
b) treating said plant cells or green algae with a mutagenizing agent,
c) contacting said mutagenized cells population with an effective amount of benzoxazinone-derivative herbicide, identified in a),
d) selecting at least one cell surviving these test conditions,
e) PCR-amplification and sequencing of PPO genes from cells selected in d) and comparing such sequences to wild-type PPO gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mut-PPO from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mut-PPO-encoding sequences.

Nucleic acids comprising candidate and control PPO encoding sequences can be expressed in yeast, in a bacterial host strain, in an alga or in a higher plant such as tobacco or *Arabidopsis* and the relative levels of inherent tolerance of the PPO encoding sequences screened according to a visible indicator phenotype of the transformed strain or plant in the presence of different concentrations of the selected benzoxazinone-derivative herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed PPO. For example, in a relatively rapid assay system based upon transformation of a bacterium such as *E. coli*, each mut-PPO encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different PPO sequences. Such strains expressing nucleic acids comprising alternative candidate PPO sequences may be plated out on different concentrations of the selected benzoxazinone-derivative herbicide in, optionally, a tyrosine supplemented medium and the relative levels of inherent tolerance of the expressed PPO enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected benzoxazinone-derivative herbicides. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control PPO. Alternatively, an untransformed dicot plant such as *Arabidopsis* or Tobacco can be used as a control since this, in any case, expresses its own endogenous PPO. The average, and distribution, of herbicide tolerance levels of a range of primary plant transformation events or their progeny to benzoxazinone-derivative described supra are evaluated in the normal manner based upon plant damage, meristematic bleaching symptoms etc. at a range of different concentrations of herbicides. These data can be expressed in terms of, for example, GR50 values derived from dose/response curves having “dose” plotted on the x-axis and “percentage kill”, “herbicidal effect”, “numbers of emerging green plants” etc. plotted on the y-axis where increased GR50 values correspond to increased levels of inherent tolerance of the expressed PPO. Herbicides can suitably be applied pre-emergence or post-emergence.

Another object refers to an isolated nucleic acid encoding a mut-PPO, wherein the nucleic acid is identifiable by a method as defined above.

In another embodiment, the invention refers to a plant cell transformed by a wild-type or a mut-PPO nucleic acid or or a plant cell which has been mutated to obtain a plant expressing a wild-type or a mut-PPO nucleic acid, wherein expression of the nucleic acid in the plant cell results in increased resistance or tolerance to a benzoxazinone-derivative herbicide as compared to a wild type variety of the plant cell.

The term “expression/expressing” or “gene expression” means the transcription of a specific gene or specific genes or specific genetic construct. The term “expression” or “gene expression” in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the benzoxazinone-derivative herbicide derivative herbicide of the present invention, it will be understood that the at least one nucleic acid is “over-expressed” by methods and means known to the person skilled in the art.

The term “increased expression” or “overexpression” as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994) The term “introduction” or “transformation” as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed.

Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein™ et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, KA and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the “floral dip” method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the “floral dip” method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mut-PPO nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, or 46, or a variant or derivative thereof; c) a polynucleotide comprising at least 60 consecutive nucleotides of any of a) or b); and d) a polynucleotide complementary to the polynucleotide of any of a) through c).

Preferably, the expression of the nucleic acid in the plant results in the plant's increased resistance to benzoxazinone-derivative herbicide as compared to a wild type variety of the plant.

In another embodiment, the invention refers to a plant, preferably a transgenic plant, comprising a plant cell according to the present invention, wherein expression of the nucleic acid in the plant results in the plant's increased resistance to benzoxazinone-derivative herbicide as compared to a wild type variety of the plant.

The plants described herein can be either transgenic crop plants or non-transgenic plants.

For the purposes of the invention, “transgenic”, “transgene” or “recombinant” means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mut-PPO nucleic acids, the nucleic acids can be derived from different genomes or from the same genome. Alternatively, in embodiments wherein the plant is non-transgenic and comprises multiple mut-PPO nucleic acids, the nucleic acids are located on different genomes or on the same genome.

In certain embodiments, the present invention involves herbicide-resistant plants that are produced by mutation breeding. Such plants comprise a polynucleotide encoding a mut-PPO and are tolerant to one or more "benzoxazinone-derivative herbicides". Such methods can involve, for example, exposing the plants or seeds to a mutagen, particularly a chemical mutagen such as, for example, ethyl methanesulfonate (EMS) and selecting for plants that have enhanced tolerance to at least one or more benzoxazinone-derivative herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mut-PPO nucleic acid or over-expressed wild-type PPO nucleic acid, and has increased tolerance to a benzoxazinone-derivative herbicide as compared to a wild-type variety of the plant. It is possible for the plants of the present invention to have multiple wild-type or mut-PPO nucleic acids from different genomes since these plants can contain more than one genome. For example, a plant contains two genomes, usually referred to as the A and B genomes. Because PPO is a required metabolic enzyme, it is assumed that each genome has at least one gene coding for the PPO enzyme (i.e. at least one PPO gene). As used herein, the term "PPO gene locus" refers to the position of an PPO gene on a genome, and the terms "PPO gene" and "PPO nucleic acid" refer to a nucleic acid encoding the PPO enzyme. The PPO nucleic acid on each genome differs in its nucleotide sequence from an PPO nucleic acid on another genome. One of skill in the art can determine the genome of origin of each PPO nucleic acid through genetic crossing and/or either sequencing methods or exonuclease digestion methods known to those of skill in the art.

The present invention includes plants comprising one, two, three, or more mut-PPO alleles, wherein the plant has increased tolerance to a benzoxazinone-derivative herbicide as compared to a wild-type variety of the plant. The mut-PPO alleles can comprise a nucleotide sequence selected from the group consisting of a polynucleotide as defined in SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof, a polynucleotide encoding a polypeptide as defined in SEQ ID NO: 2, 4, 6, 8, 10, 12, 14, 16, 18, 20, 22, 24, 26, 28, 30, 32, 34, 36, 38, 40, 42, 44, or 46, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a PPO gene of the plant or seed.

The herbicide-resistant plants of the invention that comprise polynucleotides encoding mut-PPO polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mut-PPO polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

It is to be understood that the plant of the present invention can comprise a wild type PPO nucleic acid in addition to a mut-PPO nucleic acid. It is contemplated that the benzoxazinone-derivative herbicide tolerant lines may contain a mutation in only one of multiple PPO isoenzymes. Therefore, the present invention includes a plant comprising one or more mut-PPO nucleic acids in addition to one or more wild type PPO nucleic acids.

In another embodiment, the invention refers to a seed produced by a transgenic plant comprising a plant cell of the present invention, wherein the seed is true breeding for an increased resistance to a benzoxazinone-derivative herbicide as compared to a wild type variety of the seed.

In another embodiment, the invention refers to a method of producing a transgenic plant cell with an increased resistance to a benzoxazinone-derivative herbicide as compared to a wild type variety of the plant cell comprising, transforming the plant cell with an expression cassette comprising a mut-PPO nucleic acid.

In another embodiment, the invention refers to a method of producing a transgenic plant comprising, (a) transforming a plant cell with an expression cassette comprising a mut-PPO nucleic acid, and (b) generating a plant with an increased resistance to benzoxazinone-derivative herbicide from the plant cell.

Consequently, mut-PPO nucleic acids of the invention are provided in expression cassettes for expression in the plant of interest. The cassette will include regulatory sequences operably linked to a mut-PPO nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the mut-PPO nucleic acid sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a mut-PPO nucleic acid sequence of the invention, and a transcriptional and translational termination region (i.e., termination region) functional in plants. The promoter may be native or analogous, or foreign or heterologous, to the plant host and/or to the mut-PPO nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mut-PPO nucleic acid sequence of the invention, it is intended that the promoter is not the native or naturally occurring promoter for the operably linked mut-PPO nucleic acid sequence of the invention. As used herein, a chimeric gene comprises a coding sequence operably linked to a transcription initiation region that is heterologous to the coding sequence.

While it may be preferable to express the mut-PPO nucleic acids of the invention using heterologous promoters, the native promoter sequences may be used. Such constructs would change expression levels of the mut-PPO protein in the plant or plant cell. Thus, the phenotype of the plant or plant cell is altered.

The termination region may be native with the transcriptional initiation region, may be native with the operably linked mut-PPO sequence of interest, may be native with the plant host, or may be derived from another source (i.e., foreign or heterologous to the promoter, the mut-PPO nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize Adhl, intronl gene (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mut-PPO gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al.

(1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced mut-PPO expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka e/[alpha]/. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the mut-PPO nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the mut-PPO proteins of the invention include a native chloroplast transit peptide, any chloroplast transit peptide known in the art can be fused to the amino acid sequence of a mature mut-PPO protein of the invention by operably linking a choloroplast-targeting sequence to the 5'-end of a nucleotide sequence encoding a mature mut-PPO protein of the invention. Chloroplast targeting sequences are known in the art and include the chloroplast small subunit of ribulose-I,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the mut-PPO nucleic acid comprises a polynucleotide sequence selected from the group consisting of: a) a polynucleotide as shown in SEQ ID NO: 1, 3, 5, 7, 9, 11, 13, 15, 17, 19, 21, 23, 25, 27, 29, 31, 33, 35, 37, 39, 41, 43, or 45, or a variant or derivative thereof; b) a polynucleotide encoding a polypeptide as shown in SEQ ID NO: 2, 4, 6, 8, 10, 12, 14, 16, 18, 20, 22, 24, 26, 28, 30, 32, 34, 36, 38, 40, 42, 44, or 46, or a variant or derivative thereof; c) a polynucleotide comprising at least 60 consecutive nucleotides of any of a) or c); and d) a polynucleotide complementary to the polynucleotide of any of a) through c)

Preferably, the expression cassette further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595;

Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a mut-PPO nucleic acid as described above, wherein expression of the vector in a host cell results in increased tolerance to a benzoxazinone-derivative herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mut-PPO polypeptides, fusion polypeptides, etc.).

In a preferred embodiment of the present invention, the mut-PPO polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). A mut-PPO polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N Y, 1989) and other laboratory manuals such as Methods in Molecular Biology, 1995, Vol. 44, *Agrobacterium* protocols, ed: Gartland and Davey, Humana Press, Totowa, New Jersey. As increased tolerance to benzoxazinone-derivative herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mut-PPO polynucleotide into a plant is achieved by *Agrobacterium* mediated gene transfer. One transformation method known to those of skill in the art is the dipping of a flowering plant into an Agrobacteria solution, wherein the Agrobacteria contains the mut-PPO nucleic acid, followed by breeding of the transformed gametes. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced mut-PPO polynucleotide may be maintained in the plant cell stably if it is incorporated into a non-chromosomal autonomous replicon or integrated into the plant chromosomes. Alternatively, the introduced mut-PPO polynucleotide may be present on an extra-chromosomal non-replicating vector and be transiently expressed or transiently active. In one embodiment, a homologous recombinant microorganism can be created wherein the mut-PPO polynucleotide is integrated into a chromosome, a vector is prepared which contains at least a portion of an PPO gene into which a deletion, addition, or substitution has been introduced to thereby alter, e.g., functionally disrupt, the endogenous PPO gene and to create a mut-PPO gene. To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene therapy American Scientist 87(3):240-247). Other homologous recombination procedures in *Triticum* species are also well known in the art and are contemplated for use herein.

In the homologous recombination vector, the mut-PPO gene can be flanked at its 5' and 3' ends by an additional nucleic acid molecule of the PPO gene to allow for homologous recombination to occur between the exogenous mut-PPO gene carried by the vector and an endogenous PPO gene, in a microorganism or plant. The additional flanking PPO nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the mut-PPO gene normally differs from the PPO gene at very few amino acids, a flanking sequence is not always necessary. The homologous recombination vector is introduced into a microorganism or plant cell (e.g., via polyethylene glycol mediated DNA), and cells in which the introduced mut-PPO gene has homologously recombined with the endogenous PPO gene are selected using art-known techniques.

In another embodiment, recombinant microorganisms can be produced that contain selected systems that allow for regulated expression of the introduced gene. For example, inclusion of a mut-PPO gene on a vector placing it under control of the lac operon permits expression of the mut-PPO gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mut-PPO polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a mut-PPO polynucleotide. Accordingly, the invention further provides methods for producing mut-PPO polypeptides using the host cells of the invention. In one embodiment, the method comprises culturing the host cell of invention (into which a recombinant expression vector encoding a mut-PPO polypeptide has been introduced, or into which genome has been introduced a gene encoding a wild-type or mut-PPO polypeptide) in a suitable medium until mut-PPO polypeptide is produced. In another embodiment, the method further comprises isolating mut-PPO polypeptides from the medium or the host cell. Another aspect of the invention pertains to isolated mut-PPO polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mut-PPO polypeptide in which the polypeptide is separated from some of the cellular components of the cells in which it is naturally or recombinantly produced. In one embodiment, the language "substantially free of cellular material" includes preparations of a mut-PPO polypeptide having less than about 30% (by dry weight) of non-mut-PPO material (also referred to herein as a "contaminating polypeptide"), more preferably less than about 20% of non-mut-PPO material, still more preferably less than about 10% of non-mut-PPO material, and most preferably less than about 5% non-mut-PPO material.

When the mut-PPO polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mut-PPO polypeptide in which the polypeptide is separated from chemical precursors or other chemicals that are involved in the synthesis of the polypeptide. In one embodiment, the language "substantially free of chemical precursors or other chemicals" includes preparations of a mut-PPO polypeptide having less than about 30% (by dry weight) of chemical precursors or non-mut-PPO chemicals, more preferably less than about 20% chemical precursors or non-mut-PPO chemicals, still more preferably less than about 10% chemical precursors or non-mut-PPO chemicals, and most preferably less than about 5% chemical precursors or non-mut-PPO chemicals. In preferred embodiments, isolated polypeptides, or biologically active portions thereof, lack contaminating polypeptides from the same organism from which the mut-PPO polypeptide is derived.

Typically, such polypeptides are produced by recombinant expression of, for example, a mut-PPO polypeptide in plants other than, or in microorganisms such as *C. glutamicum*, ciliates, algae, or fungi.

As described above, the present invention teaches compositions and methods for increasing the benzoxazinone-derivative tolerance of a crop plant or seed as compared to a wild-type variety of the plant or seed. In a preferred embodiment, the benzoxazinone-derivative tolerance of a crop plant or seed is increased such that the plant or seed can withstand a benzoxazinone-derivative herbicide application of preferably approximately 1-1000 g ai $ha^{-1}$, more preferably 20-160 g ai $ha^{-1}$, and most preferably 40-80 g ai $ha^{-1}$. As used herein, to "withstand" a benzoxazinone-derivative herbicide application means that the plant is either not killed or not injured by such application.

Furthermore, the present invention provides methods that involve the use of at least one benzoxazinone-derivative herbicide as described in detail supra.

In these methods, the benzoxazinone-derivative herbicide can be applied by any method known in the art including, but not limited to, seed treatment, soil treatment, and foliar treatment. Prior to application, the benzoxazinone-derivative herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to benzoxazinone-derivative herbicide, a wide variety of formulations can be employed for protecting plants from weeds, so as to enhance plant growth and reduce competition for nutrients. A benzoxazinone-derivative herbicide can be used by itself for pre-emergence, post-emergence, pre-planting, and at-planting control of weeds in areas surrounding the crop plants described herein, or a benzoxazinone-derivative herbicide formulation can be used that contains other additives. The benzoxazinone-derivative herbicide can also be used as a seed treatment. Additives found in a benzoxazinone-derivative herbicide formulation include other herbicides, detergents, adjuvants, spreading agents, sticking agents, stabilizing agents, or the like. The benzoxazinone-derivative herbicide formulation can be a wet or dry preparation and can include, but is not limited to, flowable powders, emulsifiable concentrates, and liquid concentrates. The benzoxazinone-derivative herbicide and herbicide formulations can be applied in accordance with conventional methods, for example, by spraying, irrigation, dusting, or the like.

Suitable formulations are describe in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Site-Directed Mutagenesis of *Amaranthus* PPO

Cloning of *Amaranthus* PPO

The *Amaranthus tuberculatus* coding sequence for PPO-susceptible and -resistant isoforms, and all mutant combinations and multiple mutations, (SEQ ID No: 1, 3, 5, 7) were synthesized and cloned by Geneart (Geneart AG, Regensburg, Germany).

Plasmids were isolated from *E. coli* TOP10 by performing a plasmid minpreparation and confirmed by DNA sequencing.

Expression and Purification of Recombinant Wildtype and Mutant PPO (Taken from: Franck E. Dayan, Pankaj R. Daga, Stephen O. Duke, Ryan M. Lee, Patrick J. Tranel, Robert J. Doerksen. Biochemical and structural consequences of a glycine deletion in the α-8 helix of protoporphyrinogen oxidase. Biochimica et Biophysica Acta 1804 (2010), 1548-56) Clones in pRSET vector were transformed into BL21 (DE3)-pLysS strain of *E. coli*. Cells were grown in 250 mL of LB with 100 μgmL-1 of carbenicillin, shaking overnight at 37° C. Cultures were diluted in 1 L of LB with antibiotic and grown at 37° C. shaking for 2 h, induced with 1 mM IPTG and grown at 25° C. shaking for 5 more hours. The cells were harvested by centrifugation at 1600×g, washed with 0.09% NaCl, and stored at −80° C.

Cells were lysed using a French press at 140 MPa in 50 mM sodium phosphate pH 7.5, 1 M NaCl, 5 mM imidazole, 5% glycerol, and 1 μg mL-1 leupeptin. Following lysis, 0.5 U of benzonase (Novagen, EMD Chemicals, Inc., Gibbstown, NJ) and PMSF (final concentration of 1 mM) were added. Cell debris was removed by centrifugation at 3000×g. His-tagged PPO proteins were purified on a nickel activated Hitrap Chelating HP column (GE Healthcare Bio-Sciences Corp., Piscataway, NJ) equilibrated with 20 mM sodium phosphate pH 8.0, 50 mM NaCl, 5 mM imidazole, 5 mM MgCl2, 0.1 mM EDTA, and 17% glycerol.

PPO eluted with 250 mM imidazole. The active protein was desalted on a PD-10 column (GE Healthcare Bio-Sciences Corp., Piscataway, NJ) equilibrated with a 20 mM sodium phosphate buffer, pH 7.5, 5 mM MgCl2, 1 mM EDTA and 17% glycerol. Each liter of culture provided approximately 10 mg of pure PPO, which was stored at −20° C. until being used in assays.

PPO Activity Assay

PPO Enzyme Assay (non-recombinant). PPO protein (EC 1.3.3.4) was extracted from coleoptiles or shoots (150 g fresh weight) of dark-grown corn, black nightshade, morning glory, and velvetleaf seedlings as described previously (Grossmann et al. 2010). Before harvesting, the seedlings were allowed to green for 2 hours in the light in order to achieve the highest specific enzyme activities in the thylakoid fractions at low chlorophyll concentrations. At high chlorophyll concentrations significant quenching of fluorescence occurs, which limits the amount of green thylakoids that can be used in the test. Plant materials were homogenized in the cold with a Braun blender using a fresh-weight-to-volume ratio of 1:4. Homogenization buffer consisted of tris(hydroxymethyl)aminomethane (Tris)-HCl (50 mM; pH 7.3), sucrose (0.5 M), magnesium chloride (1 mM), ethylenediaminetetraacetic acid (EDTA) (1 mM) and bovine serum albumin (2 g $L^{-1}$). After filtration through four layers of Miracloth, crude plastid preparations were obtained after centrifugation at 10 000×g for 5 min and resuspension in homogenization buffer before centrifugation at 150×g for 2 min to remove crude cell debris. The supernatant was centrifuged at 4000×g for 15 min and the pellet fraction was resuspended in 1 ml of a buffer containing Tris-HCl (50 mM; pH 7.3), EDTA (2 mM), leupeptin (2 μM), pepstatin (2 μM) and glycerol (200 ml $L^{-1}$) and stored at −80° C. until use. Protein was determined in the enzyme extract with bovine serum albumin as a standard. PPO activity was assayed fluorometrically by monitoring the rate of Proto formation from chemically reduced protoporphyrinogen IX under initial velocity conditions. The assay mixture consisted of Tris-HCl (100 mM; pH 7.3), EDTA (1 mM), dithiothreitol (5 mM), Tween 80 (0.085%), protoporphyrinogen IX (2 μM), and 40 μg extracted protein in a total volume of 200 μl. The reaction was initiated by addition of substrate protoporphyrinogen IX at 22° C. saflufenacil, benzoxazinone-derivative herbicide, flumioxazin, butafenacil, acifluorfen, lactofen, bifenox, diuron, sulfentrazone were prepared in dimethyl sulfoxide (DMSO) solution (0.1 mM concentration of DMSO in the assay) and added to the assay mixture in concentrations of 0.005 μM to 5 μM before incubation. Fluorescence was monitored directly from the assay mixture using a POLARstar Optima/Galaxy (BMG) with excitation at 405 nm and emission monitored at 630 nm. Non-enzymatic activity in the presence of heat-inactivated extract was negligible. Inhibition of enzyme activity induced by the herbicide was expressed as percentage inhibition relative to untreated controls. Molar concentrations of compound required for 50% enzyme inhibition ($IC_{50}$ values) were calculated by fitting the values to the dose-response equation using non-linear regression analysis.

PPO Enzyme Assay (recombinant). Proto was purchased from Sigma-Aldrich (Milwaukee, WI). Protogen was prepared according to Jacobs and Jacobs (N.J. Jacobs, J. M. Jacobs, Assay for enzymatic protoporphyrinogen oxidation, a late step in heme synthesis, Enzyme 28 (1982) 206-219). Assays were conducted in 100 mM sodium phosphate pH 7.4 with 0.1 mM EDTA, 0.1% Tween 20, 5 μM FAD, and 500 mM imidazole. Dose-response curves with the PPO inhibitors saflufenacil, benzoxazinone-derivative herbicide, flumioxazin, butafenacil, acifluorfen, lactofen, bifenox, diuron, sulfentrazone, and MC-15608 were obtained in the presence of 150 μM Protogen. The excitation and emission bandwidths were set at 1.5 and 30 nm, respectively. All assays were made in duplicates or triplicates and measured using a POLARstar Optima/Galaxy (BMG) with excitation at 405 nm and emission monitored at 630 nm. Molar concentrations of compound required for 50% enzyme inhibition ($IC_{50}$ values) were calculated by fitting the values to the dose-response equation using non-linear regression analysis.

Example 2. Engineering PPO-Derivative Herbicide Tolerant Plants Having Wildtype or Mutated PPO Sequences PPO-derivative herbicide tolerant soybean (*Glycine max*) or corn (*Zea mays*) plants are produced by a method as described by Olhoft et al. (US patent 2009/0049567). For transformation of soybean or *Arabidopsis thaliana*, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOI) in between ubiquitin promoter (PcUbi) and nopaline synthase terminator (NOS) sequence. For corn transformation, Wildtype or Mutated PPO sequences are cloned with standard cloning techniques as described in Sambrook et al. (Molecular cloning (2001) Cold Spring Harbor Laboratory Press) in a binary vector containing resistance marker gene cassette (AHAS) and mutated PPO sequence (marked as GOI) in between corn ubiquitin promoter (ZmUbi) and nopaline synthase terminator (NOS) sequence. Binary plasmids are introduced to *Agrobacterium tumefaciens* for plant transformation. Plasmid constructs are introduced into soybean's axillary meristem cells at the primary node of seedling explants via *Agrobacterium*-mediated transformation. After inoculation and co-cultivation with Agrobacteria, the explants are transferred to shoot introduction media without selection for one week. The explants were subsequently transferred to a shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongated or the explant died. Transgenic plantlets are rooted, subjected to TaqMan analysis for the presence of the transgene, transferred to soil and grown to maturity in greenhouse. Transformation of corn plants are done by a method described by McElver and Singh (WO 2008/124495). Plant transformation vector constructs containing mutated PPO sequences are introduced into maize immature embryos via *Agrobacterium*-mediated transformation.

Transformed cells were selected in selection media supplemented with 0.5-1.5 μM imazethapyr for 3-4 weeks. Transgenic plantlets were regenerated on plant regeneration media and rooted afterwards. Transgenic plantlets are subjected to TaqMan analysis for the presence of the transgene before being transplanted to potting mixture and grown to maturity in greenhouse. *Arabidopsis thaliana* are transformed with wildtype or mutated PPO sequences by floral dip method as described by McElver and Singh (WO 2008/124495). Transgenic *Arabidopsis* plants were subjected to TaqMan analysis for analysis of the number of integration loci. Transformation of *Oryza sativa* (rice) are done by protoplast transformation as described by Peng et al. (U.S. Pat. No. 6,653,529) TO or T1 transgenic plant of soybean, corn, and rice containing mutated PPO sequences are tested for improved tolerance to PPO-derived herbicides in greenhouse studies and mini-plot studies with the following PPO-inhibiting herbicides: saflufenacil, benzoxazinone-derivative herbicide, flumioxazin, butafenacil, acifluorfen, lactofen, bifenox, diuron, sulfentrazone.

Transgenic *Arabidopsis thaliana* plants were assayed for improved tolerance to saflufenacil, benzoxazine-derivative herbicide, flumioxazin, butafenacil, acifluorfen, lactofen, bifenox, diuron, sulfentrazone in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia *Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*$m^{-2}$*$s^{-1}$ with 14:10 h light:dark photoperiod. Growth inhibition is evaluated seven to ten days after seeding in comparison to wild type plants. Additionally, transgenic T1 *Arabidopsis* plants were tested for improved tolerance to PPO-inhibiting herbicides in greenhouse studies with the following PPO-inhibiting herbicides: saflufenacil, benzoxazinone.derivative herbicide, flumioxazin, butafenacil, acifluorfen, lactofen, bifenox, diuron, sulfentrazone.

Example 3. Tissue Culture Conditions

An in vitro tissue culture mutagenesis assay has been developed to isolate and characterize plant tissue (e.g., maize, rice tissue) that is tolerant to protoporphyrinogen oxidase inhibiting herbicides, (saflufenacil, benzoxazinone-derivative herbicide, flumioxazin, butafenacil, acifluorfen, lactofen, bifenox, diuron, sulfentrazone). The assay utilizes the somaclonal variation that is found in in vitro tissue culture. Spontaneous mutations derived from somaclonal variation can be enhanced by chemical mutagenesis and subsequent selection in a stepwise manner, on increasing concentrations of herbicide.

The present invention provides tissue culture conditions for encouraging growth of friable, embryogenic maize or rice callus that is regenerable. Calli were initiated from 4 different maize or rice cultivars encompassing *Zea mays* and *Japonica* (Taipei 309, Nipponbare, Koshihikari) and Indica (Indica 1) varieties, respectively. Seeds were surface sterilized in 70% ethanol for approximately 1 min followed by 20% commercial Clorox bleach for 20 minutes. Seeds were rinsed with sterile water and plated on callus induction media. Various callus induction media were tested. The ingredient lists for the media tested are presented in Table 4.

butafenacil, acifluorfen, lactofen, bifenox, diuron, sulfentrazone in selection media, the tissues were selected in a step-wise fashion by increasing the concentration of the PPO inhibitor with each transfer until cells are recovered that grew vigorously in the presence of toxic doses. The resulting calli were further subcultured every 3-4 weeks to R001M with selective agent. Over 26,000 calli were subjected to selection for 4-5 subcultures until the selective pressure was above toxic levels as determined by kill curves and observations of continued culture.

Alternatively, liquid cultures initiated from calli in MS711R with slow shaking and weekly subcultures. Once liquid cultures were established, selection agent was added directly to the flask at each subculture. Following 2-4 rounds of liquid selection, cultures were transferred to filters on solid R001M media for further growth.

TABLE 4

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 μg/L | |
| 2,4-D | Sigma | 2.0 mg/L | | | | | 1.0 mg/L |
| $MgCl_2 \cdot 6H_2O$ | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001 M callus induction media was selected after testing numerous variations. Cultures were kept in the dark at 30° C. Embryogenic callus was subcultured to fresh media after 10-14 days.

Example 4. Selection of Herbicide-Tolerant Calli

Once tissue culture conditions were determined, further establishment of selection conditions were established through the analysis of tissue survival in kill curves with saflufenacil, benzoxazinone-derivative herbicide, flumioxazin, butafenacil, acifluorfen, lactofen, bifenox, diuron, sulfentrazone. Careful consideration of accumulation of the herbicide in the tissue, as well as its persistence and stability in the cells and the culture media was performed. Through these experiments, a sub-lethal dose has been established for the initial selection of mutated material.

After the establishment of the starting dose of saflufenacil, benzoxazinone-derivative herbicide, flumioxazin, Example 5. Regeneration of Plants Tolerant tissue was regenerated and characterized molecularly for PPO gene sequence mutations and/or biochemically for altered PPO activity in the presence of the selective agent. In addition, genes involved directly and/or indirectly in tetrapyrrole biosynthesis and/or metabolism pathways were also sequenced to characterize mutations. Finally, enzymes that change the fate (e.g. metabolism, translocation, transportation) were also sequence to characterized mutations.

Following herbicide selection, calli were regenerated using a media regime of R025M for 10-14 days, R026M for ca. 2 weeks, R327M until well formed shoots were developed, and R008S until shoots were well rooted for transfer to the greenhouse. Regeneration was carried out in the light. No selection agent was included during regeneration.

Once strong roots were established, MO regenerants were transplant to the greenhouse in square or round pots. Trans-plants were maintained under a clear plastic cup until they were adapted to greenhouse conditions. The greenhouse was set to a day/night cycle of 27° C./21° C. (80° F./70° F.) with 600 W high pressure sodium lights supplementing light to maintain a 14 hour day length. Plants were watered according to need, depending in the weather and fertilized daily.

Example 6. Sequence Analysis

Leaf tissue was collected from clonal plants separated for transplanting and analyzed as individuals. Genomic DNA was extracted using a Wizard® 96 Magnetic DNA Plant System kit (Promega, U.S. Pat. Nos. 6,027,945 & 6,368, 800) as directed by the manufacturer. Isolated DNA was PCR amplified using the appropriate forward and reverse primer.

PCR amplification was performed using Hotstar Taq DNA Polymerase (Qiagen) using touchdown thermocycling program as follows: 96° C. for 15 min, followed by 35 cycles (96° C., 30 sec; 58° C.–0.2° C. per cycle, 30 sec; 72° C., 3 min and 30 sec), 10 min at 72° C.

PCR products were verified for concentration and fragment size via agarose gel electrophoresis. Dephosphorylated PCR products were analyzed by direct sequence using the PCR primers (DNA Landmarks, or Entelechon). Chromatogram trace files (.scf) were analyzed for mutation relative to the wild-type gene using Vector NTI Advance 10™ (Invitrogen). Based on sequence information, mutations were identified in several individuals. Sequence analysis was performed on the representative chromatograms and corresponding AlignX alignment with default settings and edited to call secondary peaks.

Example 7. Demonstration of Herbicide-Tolerance

Selected mutants and escapes were transferred to small pots. Wild-type cultivars were germinated from seed to serve as controls.

After ca. 3 weeks post-transplant, MO regenerants were sprayed using a track sprayer with saflufenacil, benzoxazinone-derivative herbicide, flumioxazin, butafenacil, acifluorfen, lactofen, bifenox, diuron, sulfentrazone supplemented with 0.1% methylated seed oil. After the plants had adapted to greenhouse conditions, a subset were sprayed with additional saflufenacil or benzoxazinone-derivative herbicide. Once sprayed, plants were kept on drought conditions for 24 hours before being watered and fertilized again. Sprayed plants were photographed and rated for herbicide injury at 1 and 3 weeks after treatment. No injury was observed on plants containing the heterozygous mutation while control plants and tissue culture escapes (regenerated plants negative for the sequenced mutations) were heavily damaged after treatment.

Example 8. Herbicide Selection Using Tissue Culture

Media was selected for use and kill curves developed as specified above. For selection, different techniques were utilized. Either a step wise selection was applied, or an immediate lethal level of herbicide was applied. In either case, all of the calli were transferred for each new round of selection. Selection was 4-5 cycles of culture with 3-5 weeks for each cycle. Cali were placed onto nylon membranes to facilitate transfer (200 micron pore sheets, Biodesign, Saco, Maine). Membranes were cut to fit 100×20 mm Petri dishes and were autoclaved prior to use 25-35 calli (average weight/calli being 22 mg) were utilized in every plate. In addition, one set of calli were subjected to selection in liquid culture media with weekly subcultures followed by further selection on semi-solid media.

Mutant lines were selected using saflufenacil, benzoxazinone-derivative herbicide, flumioxazin, butafenacil, acifluorfen, lactofen, bifenox, diuron, sulfentrazone. Efficiencies of obtaining mutants was high either based on a percentage of calli that gave rise to a regenerable, mutant line or the number of lines as determined by the gram of tissue utilized.

Example 9 Screening of Mutagenized Algae Cells to Identify Herbicide Tolerant Clones and Identification of Causative Mutations in PPO Genes To generate mutations in PPO genes conferring "PPO-inhibiting herbicides" resistance, screening with chemical or UV mutagenized cell populations can be used. Especially unicellular organisms like *Chlamydomonas reinhardtii* are useful for identifying dominant mutations conferring herbicide resistance (Kataoka M, et al.; 1990; J. of Pest. Sci. 15: 449-451; Oshio H, et al.; 1993; Zeitschrift für Naturforschung 48: 339-344).

Algae cells of *Chlamydomonas reinhardtii* strains CC-503 and CC-1691 (Duke University, Durham, USA) were propagated in TAP medium (Gorman and Levine; 1965; PNAS 54: 1665-1669) by constant shaking at 100 rpm, 22° C. and 30 μmol Phot*$m^{-2}$*$s^{-2}$ light illumination. Compound screening was performed at 450 μmol Phot*$m^{-2}$*$s^{-2}$ illumination.

Sensitive strains of *Chlamydomonas reinhardtii* were mutagenized with 0.14 M ethylmethanesulfonate (EMS) for 1 h as described by Loppes (1969, Mol Gen Genet 104: 172-177). Tolerant strains are identified by screening of mutagenized cells on solid TAP medium plates containing "PPO-inhibiting herbicide" like saflufenacil or benzoxazinone-derivative herbicide at wildype-lethal concentrations depending on compound activity in CC-503 or CC-1691 strain.

Standard techniques were used for isolation of RNA and cDNA synthesis as described by Sambrock et al. (Molecular cloning (2001) Cold Spring Harbor Laboratory Press). Amplification of PPO genes from wild-type and resistant *Chlamydomonas reinhardii* from genomic DNA or copy DNA as template were performed by standard PCR techniques with DNA oligonucleotides as listed in Table 5. The resulting DNA molecules were cloned in standard sequencing vector (pJET1) and sequenced by standard sequencing techniques. Mutations were identified by comparing wild-type and mutant PPO sequences by sequence alignment tool Align X (Vector NTI Advance Software Version 10.3, Invitrogen, Carlsbad, CA, USA).

TABLE 5

PCR primer for amplification of CrPPO

| Primer name | Primer sequence (5'-3') |
|---|---|
| Cr_PPO1_Fw | ATGATGTTGACCCAGACTCCTGGGAC |
| Cr PPO1_Rv | TTAGGCCTTGACTGCGGCCTTGGAC |

The invention claimed is:

1. A plant comprising a nucleic acid encoding a herbicide tolerant mutant protoporphyrinogen oxidase, (PPO) polypeptide comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine, wherein the plant is selected from the group consisting of *Brassica napus, Zea mays, Oryza sativa, Beta vulgaris*, and *Gossypium hirsutum.*

2. The plant of claim 1, wherein the amino acid corresponding to position Leu397 of SEQ ID NO:2 is substituted with aspartate and the amino acid corresponding to position Phe420 of SEQ ID NO:2 is substituted with valine.

3. The plant of claim 1, wherein the amino acid corresponding to position Leu397 of SEQ ID NO:2 is substituted with glutamate and the amino acid corresponding to position Phe420 of SEQ ID NO:2 is substituted with methionine.

4. The plant of claim 1, wherein the amino acid corresponding to position Leu397 of SEQ ID NO:2 is substituted with glutamine and the amino acid corresponding to position Phe420 of SEQ ID NO:2 is substituted with valine.

5. The plant of claim 1, wherein the amino acid corresponding to position Leu397 of SEQ ID NO:2 is substituted with aspartate and the amino acid corresponding to position Phe420 of SEQ ID NO:2 is substituted with methionine.

6. The plant of claim 1, wherein the amino acid corresponding to position Leu397 of SEQ ID NO:2 is substituted with glutamate and the amino acid corresponding to position Phe420 of SEQ ID NO:2 is substituted with valine.

7. The plant of claim 1, wherein the amino acid corresponding to position Leu397 of SEQ ID NO:2 is substituted with glutamine and the amino acid corresponding to position Phe420 of SEQ ID NO:2 is substituted with methionine.

8. The plant of claim 2, wherein the plant is non-transgenic.

9. The plant of claim 3, wherein the plant is non-transgenic.

10. The plant of claim 4, wherein the plant is non-transgenic.

11. The plant of claim 5, wherein the plant is non-transgenic.

12. The plant of claim 6, wherein the plant is non-transgenic.

13. The plant of claim 7, wherein the plant is non-transgenic.

14. A seed comprising a nucleic acid encoding a herbicide tolerant mutant PPO polypeptide comprising an amino acid substitution at a position corresponding to position Leu397 of SEQ ID NO:2 and an amino acid substitution at a position corresponding to position Phe420 of SEQ ID NO:2, wherein the amino acid corresponding to position Leu397 of SEQ ID NO:2 is substituted with aspartate, glutamate, or glutamine, and wherein the amino acid corresponding to position Phe420 of SEQ ID NO:2 is substituted with valine or methionine, wherein the seed is from a plant selected from the group consisting of *Brassica napus, Zea mays, Oryza sativa, Beta vulgaris*, and *Gossypium hirsutum*.

15. The seed of claim 14, wherein the amino acid corresponding to position Leu397 of SEQ ID NO:2 is substituted with aspartate and the amino acid corresponding to position Phe420 of SEQ ID NO:2 is substituted with valine.

16. The seed of claim 14, wherein the amino acid corresponding to position Leu397 of SEQ ID NO:2 is substituted with glutamate and the amino acid corresponding to position Phe420 of SEQ ID NO:2 is substituted with methionine.

17. The seed of claim 14, wherein the amino acid corresponding to position Leu397 of SEQ ID NO:2 is substituted with glutamine and the amino acid corresponding to position Phe420 of SEQ ID NO:2 is substituted with valine.

18. The seed of claim 14, wherein the amino acid corresponding to position Leu397 of SEQ ID NO:2 is substituted with aspartate and the amino acid corresponding to position Phe420 of SEQ ID NO:2 is substituted with methionine.

19. The seed of claim 14, wherein the amino acid corresponding to position Leu397 of SEQ ID NO:2 is substituted with glutamate and the amino acid corresponding to position Phe420 of SEQ ID NO:2 is substituted with valine.

20. The seed of claim 14, wherein the amino acid corresponding to position Leu397 of SEQ ID NO:2 is substituted with glutamine and the amino acid corresponding to position Phe420 of SEQ ID NO:2 is substituted with methionine.

* * * * *